(12) United States Patent
Mitsudera

(10) Patent No.: US 8,513,162 B2
(45) Date of Patent: Aug. 20, 2013

(54) HALOGEN-CONTAINING ORGANOSULFUR COMPOUND AND USE THEREOF

(75) Inventor: Hiromasa Mitsudera, Westmount (CA)

(73) Assignee: Sumitomo Chemical Company, Limited, Tokyo (JP)

( * ) Notice: Subject to any disclaimer, the term of this patent is extended or adjusted under 35 U.S.C. 154(b) by 56 days.

(21) Appl. No.: 13/141,643

(22) PCT Filed: Dec. 24, 2009

(86) PCT No.: PCT/JP2009/071867
§ 371 (c)(1), (2), (4) Date: Jun. 22, 2011

(87) PCT Pub. No.: WO2010/074327
PCT Pub. Date: Jul. 1, 2010

(65) Prior Publication Data
US 2011/0257226 A1 Oct. 20, 2011

(30) Foreign Application Priority Data
Dec. 24, 2008 (JP) ................................. 2008-327876

(51) Int. Cl.
| | | |
|---|---|---|
| A01N 43/08 | (2006.01) | |
| A01N 43/10 | (2006.01) | |
| A01N 43/16 | (2006.01) | |
| A01N 43/18 | (2006.01) | |
| A01N 43/28 | (2006.01) | |
| A01N 43/40 | (2006.01) | |
| C07D 211/34 | (2006.01) | |
| C07D 335/02 | (2006.01) | |
| C07D 333/24 | (2006.01) | |
| C07D 333/48 | (2006.01) | |

(52) U.S. Cl.
USPC ........... 504/248; 504/249; 504/288; 504/289; 504/292; 504/294; 504/295; 546/245; 546/246; 549/13; 549/28; 549/75; 549/87; 549/426; 549/427; 549/475; 549/491; 549/497

(58) Field of Classification Search
USPC .............. 546/248, 246, 245; 549/13, 28, 549/75, 67, 491, 497, 426, 427, 475, 87; 504/248, 249, 288, 289, 292, 294, 295
See application file for complete search history.

(56) References Cited

FOREIGN PATENT DOCUMENTS

| | | |
|---|---|---|
| AU | 728843 B2 | 3/1998 |
| JP | 2005-179321 A | 7/2005 |
| JP | 2007-55964 A | 3/2007 |
| JP | 2007-161617 A | 6/2007 |
| JP | 2007-186494 A | 7/2007 |
| WO | WO 92/07570 A1 | 5/1992 |
| WO | WO 98/07740 A1 | 2/1998 |
| WO | WO 01/12622 A1 | 2/2001 |
| WO | WO 2009/005110 A2 | 1/2009 |

OTHER PUBLICATIONS

International Preliminary Report on Patentability and Written Opinion of the International Searching Authority dated Jul. 7, 2011 for Application No. PCT/JP2009/071867 (PCT/IB/326, PCT/IB/373 and PCT/ISA/237).
International Search Report, dated May 25, 2010 in PCT/JP2009/071867.
Notification of Reasons for Refusai for corresponding Japanese Patent Application No. 2009-290231, mailed Nov. 6, 2012.
Communication pursuant to Article 94(3) EPC for corresponding European Patent Application No. 09801823.7, dated Nov. 8, 2012.
First Office Action for corresponding Chinese Patent Application No. 200980157520.0, dated Feb. 8, 2013.

*Primary Examiner* — Jason M Nolan
(74) *Attorney, Agent, or Firm* — Birch, Stewart, Kolasch & Birch, LLP

(57) ABSTRACT

There is provided a halogen-containing organosulfur compound having a controlling effect on arthropod pests represented by the formula (I): wherein m represents 0, 1 or 2; n represents 0, 1 or 2; A represents an optionally substituted 3- to 8-membered saturated heterocyclic group; Q represents a fluorine atom or a C1-C5 haloalkyl group having at least one fluorine atom; $R^1$, $R^{1a}$ and $R^3$ independently represent an optionally halogenated C1-C4 chain hydrocarbon group, etc.; $R^2$, $R^{2a}$ and $R^4$ independently represent an optionally halogenated C1-C4 chain hydrocarbon group, etc.

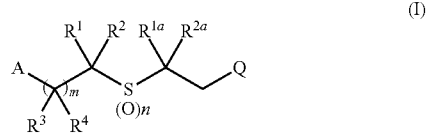

(I)

8 Claims, No Drawings

HALOGEN-CONTAINING ORGANOSULFUR COMPOUND AND USE THEREOF

TECHNICAL FIELD

The present invention relates to a halogen-containing organosulfur compound and use thereof.

BACKGROUND ART

Hitherto, various pesticidal compositions for controlling arthropod pests have been developed and put into practical use. For example, JP-A 2007-186494, JP-A 2007-161617 and JP-A 2007-055964 disclose halogen-containing organosulfur compounds.

SUMMARY OF INVENTION

Technical Problem

An object of the present invention is to provide a novel compound having excellent control effect on arthropod pests, and the use of the compound for control of arthropod pests.

Solution to Problem

The present inventors have intensively studied to find out a compound having an excellent controlling effect on arthropod pests. As a result, they have found that a halogen-containing organosulfur compound represented by the following formula (I) has an excellent controlling activity against arthropod pests such as insects and mites, and thus the present invention has been completed.

The present invention provides:
[1] A halogen-containing organosulfur compound represented by the following formula (I):

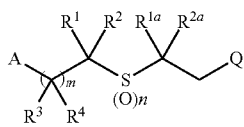

wherein
m represents 0, 1 or 2,
n represents 0, 1 or 2,
A represents a 3- to 8-membered saturated heterocyclic group optionally substituted with a group selected from the group E1,
Q represents a fluorine atom, or a C1-C5 haloalkyl group containing at least one fluorine atom,
$R^1$, $R^{1a}$ and $R^3$ independently represent an optionally halogenated C1-C4 chain hydrocarbon group, a halogen atom, or a hydrogen atom,
$R^2$, $R^{2a}$ and $R^4$ independently represent an optionally halogenated C1-C4 chain hydrocarbon group, —C(=G)$R^5$, a cyano group, a halogen atom, or a hydrogen atom,
G represents an oxygen atom or a sulfur atom,
$R^5$ represents an optionally halogenated C1-C4 alkyl group, a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, or a hydrogen atom,
the group E1 consists of –$OR^6$, —$SR^6$, —S(=O)$R^6$, —S(=O)$_2R^6$, —C(=O)$R^7$, —OC(=O)$R^8$, a C1-C6 chain hydrocarbon group optionally substituted with a group selected from the group L, an optionally halogenated C3-C6 cycloalkyl group, a cyano group, a hydroxyl group, and a halogen atom,
$R^6$ represents a C1-C6 chain hydrocarbon group optionally substituted with a group selected from the group L, or an optionally halogenated C3-C6 cycloalkyl group,
$R^7$ represents a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl) amino group, a C2-C5 cyclic amino group, an optionally halogenated C1-C4 alkyl group, or a hydrogen atom,
$R^8$ represents an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl group, or a hydrogen atom,
the group L consists of a hydroxyl group, an optionally halogenated C1-C4 alkoxy group, an optionally halogenated C3-C6 alkenyloxy group, an optionally halogenated C3-C6 alkynyloxy group, —C(=O)$R^7$, —OC(=O)$R^8$, —N($R^9$)$R^{10}$, a C2-C5 cyclic amino group, and a halogen atom, and
$R^9$ and $R^{10}$ independently represent an optionally halogenated C1-C4 alkyl group, an optionally halogenated C3-C6 alkenyl group, an optionally halogenated C3-C6 alkynyl group, an optionally halogenated C3-C6 cycloalkyl group, an optionally halogenated phenyl group, or a hydrogen atom;
[2] The halogen-containing organosulfur compound according to [1], wherein $R^3$ and $R^4$ are hydrogen atoms;
[3] The halogen-containing organosulfur compound according to [1], wherein m is 0;
[4] The halogen-containing organosulfur compound according to [1], wherein $R^1$ is a halogen atom or a hydrogen atom, and $R^2$ is —C(=G)$R^5$ or a cyano group;
[5] The halogen-containing organosulfur compound according to [1], wherein $R^{1a}$ is a halogen atom or a hydrogen atom, and $R^{2a}$ is —C(G)$R^5$ or a cyano group;
[6] An arthropod pest-controlling composition comprising the halogen-containing organosulfur compound according to any one of [1] to [5] as an active ingredient; and
[7] A method for controlling an arthropod pest, which comprises applying an effective amount of the halogen-containing organosulfur compound according to any one of [1] to [5] to the arthropod pest or a habitat of the arthropod pest.

Effects of Invention

The compound of the present invention has an excellent controlling effect on arthropod pests.

MODE FOR CARRYING OUT THE INVENTION

As used herein, for example, the "fluoroalkyl group" means an alkyl group substituted with one or more fluorine atoms. The expression "C1-C6" or the like, as used herein, means the total number of carbon atoms constituting each substituent group.

As used herein, the "halogen atom" means a fluorine atom, a chlorine atom, a bromine atom, or an iodine atom.

A saturated heterocyclic group contains one or two heteroatoms selected from an oxygen atom, a nitrogen atom and a sulfur atom.

The present invention includes each active isomer and an active mixture of the isomers at any ratio thereof, in cases where the present compound has stereoisomers originated from an asymmetric carbon atom which is connected with $R^1$ and $R^2$, from an asymmetric carbon atom which is connected with $R^{1a}$ and $R^{2a}$, from an asymmetric carbon atom which is connected with $R^3$ and $R^4$ or from an asymmetric carbon atom on a 3- to 8-membered saturated heterocyclic group optionally substituted with a group selected from the group E1, or in case where the present compound has geometrical isomers originated from an alkenyl group.

As used herein, examples of the 3- to 8-membered saturated heterocyclic group include a 3-membered saturated heterocyclic group such as an oxiranyl group, a thiiranyl group, and an aziridinyl group;
a 4-membered saturated heterocyclic group such as an oxetanyl group, a thietanyl group, and an azetidinyl group;
5-membered saturated heterocyclic groups such as an oxolanyl group (tetrahydrofuranyl group), a thiolanyl group (tetrahydrothiophenyl group), a pyrrolidinyl group, a dioxolanyl group, and a dithiolanyl group;
a 6-membered saturated heterocyclic group such as an oxanyl group (tetrahydropyranyl group), a thianyl group (tetrahydrothiopyranyl group), a piperidinyl group, a 1,3-dioxanyl group, a 1,4-dioxanyl group, a 1,3-dithianyl group, a 1,4-dithianyl group, a morpholinyl group, and a piperazinyl group; and
a 7-membered saturated heterocyclic group such as an oxepanyl group, a thiepanyl group, and an azepanyl group. Specific examples thereof include saturated heterocyclic groups represented by the following formulae:

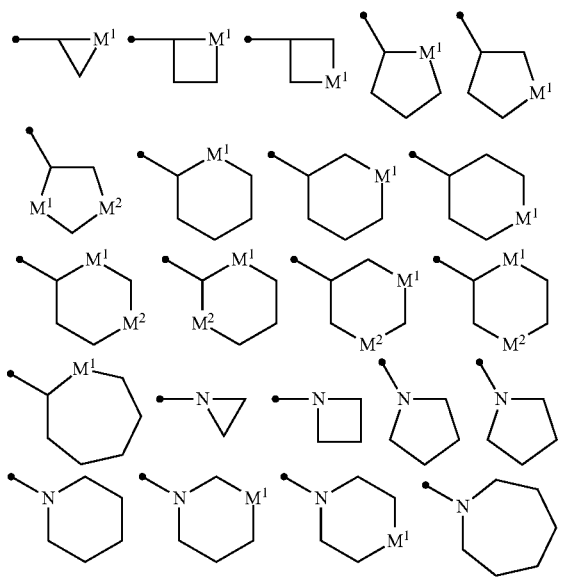

wherein $M^1$ and $M^2$ independently represent an oxygen atom, a sulfur atom, or NH.

In the group E1, examples of the "C1-C6 chain hydrocarbon group optionally substituted with a group selected from the group L" include a C1-C6 alkyl group such as a methyl group, an ethyl group, a propyl group, and a butyl group;
a C1-C6 alkyl group substituted with a group selected from the group L, such as a fluoromethyl group, a difluoromethyl group, a trifluoromethyl group, a 2-propynyloxymethyl group, a 2-butynyloxymethyl group, and a hydroxymethyl group;
a C2-C6 alkenyl group such as a vinyl group, a 1-propenyl group, and a 2-propenyl group;
a C2-C6 alkenyl group substituted with a group selected from the group L, such as a 2,2-difluorovinyl group and a 2,2-difluoro-1-propenyl group;
a C2-C6 alkynyl group such as an ethynyl group, a 1-propynyl group, a 2-propynyl group, a 1-butynyl group, a 2-butynyl group, a 3-butynyl group, a 1-pentynyl group, a 2-pentynyl group, and a 3-pentynyl group; and
a C2-C6 alkynyl group substituted with a group selected from the group L, such as a 3-methoxy-1-propynyl group, a 3-methoxy-1-butynyl group, a 4-methoxy-1-butynyl group, a 4-methoxy-2-butynyl group, a 3-methoxy-1-pentynyl group, a 4-methoxy-1-pentynyl group, a 5-methoxy-1-pentynyl group, a 4-methoxy-2-pentynyl group, a 5-methoxy-2-pentynyl group, a 5-methoxy-3-pentynyl group, a 3-hydroxy-1-propynyl group, a 3-hydroxy-1-butynyl group, a 4-hydroxy-1-butynyl group, a 4-hydroxy-2-butynyl group, a 3-hydroxy-1-pentynyl group, a 4-hydroxy-1-pentynyl group, a 5-hydroxy-1-pentynyl group, a 4-hydroxy-2-pentynyl group, a 5-hydroxy-2-pentynyl group, a 5-hydroxy-3-pentynyl group, a 3-methylamino-1-propynyl group, a 3-methylamino-1-butynyl group, a 4-methylamino-1-butynyl group, a 4-methylamino-2-butynyl group, a 3-methylamino-1-pentynyl group, a 4-methylamino-1-pentynyl group, a 5-methylamino-1-pentynyl group, a 4-methylamino-2-pentynyl group, a 5-methylamino-2-pentynyl group, a 5-methylamino-3-pentynyl group, a 3-dimethylamino-1-propynyl group, a 3-dimethylamino-1-butynyl group, a 4-dimethylamino-1-butynyl group, a 4-dimethylamino-2-butynyl group, a 3-dimethylamino-1-pentynyl group, a 4-dimethylamino-1-pentynyl group, a 5-dimethylamino-1-pentynyl group, a 4-dimethylamino-2-pentynyl group, a 5-dimethylamino-2-pentynyl group, a 5-dimethylamino-3-pentynyl group, a 3-phenylamino-1-propynyl group, a 3-phenylamino-1-butynyl group, a 4-phenylamino-1-butynyl group, a 4-phenylamino-2-butynyl group, a 3-phenylamino-1-pentynyl group, a 4-phenylamino-1-pentynyl group, a 5-phenylamino-1-pentynyl group, a 4-phenylamino-2-pentynyl group, a 5-phenylamino-2-pentynyl group, a 5-phenylamino-3-pentynyl group, a 3-methylphenylamino-1-propynyl group, a 3-methylphenylamino-1-butynyl group, a 4-methylphenylamino-1-butynyl group, a 4-methylphenylamino-2-butynyl group, a 3-methylphenylamino-1-pentynyl group, a 4-methylphenylamino-1-pentynyl group, a 5-methylphenylamino-1-pentynyl group, a 4-methylphenylamino-2-pentynyl group, a 5-methylphenylamino-2-pentynyl group, a 5-methylphenylamino-3-pentynyl group, a 3-(1-pyrrolidinyl)-1-propynyl group, a 3-(1-pyrrolidinyl)-1-butynyl group, a 4-(1-pyrrolidinyl)-1-butynyl group, a 4-(1-pyrrolidinyl)-2-butynyl group, a 3-(1-pyrrolidinyl)-1-pentynyl group, a 4-(1-pyrrolidinyl)-1-pentynyl group, a 5-(1-pyrrolidinyl)-1-pentynyl group, a 4-(1-pyrrolidinyl)-2-pentynyl group, a 5-(1-pyrrolidinyl)-2-pentynyl group, a 5-(1-pyrrolidinyl)-3-pentynyl group, a 3-(1-piperidinyl)-1-propynyl group, a 3-(1-piperidinyl)-1-butynyl group, a 4-(1-piperidinyl)-1-butynyl group, a 4-(1-piperidinyl)-2-butynyl group, a 3-(1-piperidinyl)-1-pentynyl group, a 4-(1-piperidinyl)-1-pentynyl group, a 5-(1-piperidinyl)-1-pentynyl group, a 4-(1-piperidinyl)-2-pentynyl group, a 5-(1-piperidinyl)-2-pentynyl group, a 5-(1-piperidinyl)-3-pentynyl group, a 3-(1-morpholinyl)-1-propynyl group, a 3-(1-morpholinyl)-1-butynyl group, a 4-(1-morpholinyl)-1-butynyl group, a 4-(1-morpholinyl)-2-butynyl group, a 3-(1-morpholinyl)-1-pentynyl group, a 4-(1-morpholinyl)-1-pentynyl group, a 5-(1-morpholinyl)-1-pentynyl group, a 4-(1-morpholinyl)-2-pentynyl group, a 5-(1-morpholinyl)-2-pentynyl group, a 5-(1-morpholinyl)-3-pentynyl group, a 3-methoxycarbonyl-1-propynyl group, a 3-methoxycarbonyl-1-butynyl group, a 4-methoxycarbonyl-1-butynyl group, a 4-methoxycarbonyl-2-butynyl group, a 3-methoxycarbonyl-1-pentynyl group, a 4-methoxycarbonyl-1-pentynyl group, a 5-methoxycarbonyl-1-pentynyl group, a 4-methoxycarbonyl-2-pentynyl group, a 5-methoxycarbonyl-2-pentynyl group, a 5-methoxycarbonyl-3-pentynyl group, a 3-dimethylaminocarbonyl-1-propynyl group, a 3-dimethylaminocarbonyl-1-butynyl group, a 4-dimethylaminocarbonyl-1-butynyl group, a 4-dimethylaminocarbonyl-2-butynyl group, a 3-dimethylaminocarbonyl-1-pentynyl group, a 4-dimethylaminocarbonyl-1-pentynyl group, a 5-dimethylaminocarbonyl-1-pentynyl group, a 4-dimethylaminocarbonyl-2-pentynyl group, a 5-dimethylaminocarbonyl-2-pentynyl group, a 5-dimethylaminocarbonyl-3-pentynyl group, a 3-(1-pyrrolidinyl)carbonyl-1-propynyl group, a 3-(1-pyrrolidinyl)carbonyl-1-butynyl group, a 4-(1-pyrrolidinyl)carbonyl-1-butynyl group, a 4-(1-pyrrolidinyl)carbonyl-2-butynyl group, a 3-(1-pyrrolidinyl)carbonyl-1-pentynyl group, a 4-(1-pyrrolidinyl)carbonyl-1-pentynyl group, a 5-(1-pyrrolidinyl)carbonyl-1-pentynyl group, a 4-(1-pyrrolidinyl)carbonyl-2-pentynyl group, a 5-(1-pyrrolidinyl)carbonyl-2-pentynyl group, a 5-(1-pyrrolidinyl)carbonyl-3-pentynyl group, a 3-(1-piperidinyl)carbonyl-1-propynyl group, a 3-(1-piperidinyl)carbonyl-1-butynyl group, a 4-(1-piperidinyl)carbonyl-1-butynyl group, a 4-(1-piperidinyl)carbonyl-2-butynyl group, a 3-(1-piperidinyl)carbonyl-1-pentynyl group, a 4-(1-piperidinyl)carbonyl-1-pentynyl group, a 5-(1-piperidinyl)carbonyl-1-pentynyl group, a 4-(1-piperidinyl)carbonyl-2-pentynyl group, a 5-(1-piperidinyl)carbonyl-2-pentynyl group, a 5-(1-piperidinyl)carbonyl-3-pentynyl group, a 3-(1-morpholinyl)carbonyl-1-propynyl group, a 3-(1-morpholinyl)carbonyl-1-butynyl group, a 4-(1-morpholinyl)carbonyl-1-butynyl group, a 4-(1-morpholinyl)carbonyl-2-butynyl group, a 3-(1-morpholinyl)carbonyl-1-pentynyl group, a 4-(1-morpholinyl)carbonyl-1-pentynyl group, a 5-(1-morpholinyl)carbonyl-1-pentynyl group, a 4-(1-morpholinyl)carbonyl-2-pentynyl group, a 5-(1-morpholinyl)carbonyl-2-pentynyl group, a 5-(1-morpholinyl)carbonyl-3-pentynyl group, a 3-carboxy-1-propynyl group, a 3-carboxy-1-butynyl group, a 4-carboxy-1-butynyl group, a 4-carboxy-2-butynyl group, a 3-carboxy-1-pentynyl group, a 4-carboxy-1-pentynyl group, a 5-carboxy-1-pentynyl group, a 4-carboxy-2-pentynyl group, a 5-carboxy-2-pentynyl group, a 5-carboxy-3-pentynyl group, a 3-acetoxy-1-propynyl group, a 3-acetoxy-1-butynyl group, a 4-acetoxy-1-butynyl group, a 4-acetoxy-2-butynyl group, a 3-acetoxy-1-pentynyl group, a 4-acetoxy-1-pentynyl group, a 5-acetoxy-1-pentynyl group, a 4-acetoxy-2-pentynyl group, a 5-acetoxy-2-pentynyl group, a 5-acetoxy-3-pentynyl group, a 3-methoxycarbonyloxy-1-propynyl group, a 3-methoxycarbonyloxy-1-butynyl group, a 4-methoxycarbonyloxy-1-butynyl group, a 4-methoxycarbonyloxy-2-butynyl group, a 3-methoxycarbonyloxy-1-pentynyl group, a 4-methoxycarbonyloxy-1-pentynyl group, a 5-methoxycarbonyloxy-1-pentynyl group, a 4-methoxycarbonyloxy-2-pentynyl group, a 5-methoxycarbonyloxy-2-pentynyl group, a 5-methoxycarbonyloxy-3-pentynyl group, 2-bromoethynyl group, 2-iodoethynyl group, a 3-fluoro-1-propynyl group, a 3,3-difluoro-1-propynyl group, a 3,3,3-trifluoro-1-propynyl group, a 3-fluoro-1-propynyl group, a 3,3-difluoro-1-propynyl group, a 3,3,3-trifluoro-1-propynyl group, 1-fluoro-2-propynyl group, 1,1-difluoro-2-propynyl group, a 3-fluoro-1-butynyl group, a 4-fluoro-1-butynyl group, a 3-fluoro-1-pentynyl group, a 4-fluoro-1-pentynyl group, and a 5-fluoro-1-pentynyl group.

Examples of the "optionally halogenated C3-C6 cycloalkyl group" as used herein include a cyclopropyl group, a 1-methylcyclopropyl group, a 2,2-dichlorocyclopropyl group, a 2,2-dichloro-1-methylcyclopropyl group, a 2,2-difluorocyclopropyl group, a 2,2-difluoro-1-methylcyclopropyl group, a cyclobutyl group, a cyclopentyl group, and a cyclohexyl group.

Examples of a group represented by "—OR$^6$" include a C1-C4 alkoxy group such as a 2-propoxy group and a 2-butoxy group; a C1-C4 haloalkoxy group such as a 1,1,1-trifluoro-2-propoxy group and a 1,1,1-trifluoro-2-butoxy group; a C3-C6 alkenyloxy group; a C3-C6 haloalkenyloxy group; a C3-C6 alkenyloxy group; and a C3-C6 haloalkynyloxy group.

Examples of a group represented by "—SR$^6$" include a C1-C4 alkylthio group and a C1-C4 haloalkylthio group.

Examples of a group represented by "—S(=O)R$^6$" include a C1-C4 alkylsulfinyl group and a C1-C4 haloalkylsulfinyl group.

Examples of a group represented by "—S(=O)$_2$R$^6$" include a C1-C4 alkylsulfonyl group and a C1-C4 haloalkylsulfonyl group.

Examples of R$^7$ in "—C(=O)R$^7$" include a C1-C4 alkyl group; a C1-C4 haloalkyl group; a C1-C4 alkoxy group; a C1-C4 haloalkoxy group; a C3-C6 alkenyloxy group; a C3-C6 haloalkenyloxy group; a C3-C6 alkynyloxy group; a C3-C6 haloalkynyloxy group; an amino group; a C1-C4 alkylamino group; a C1-C4 haloalkylamino group; a di(C1-C4 alkyl)amino group; a di(C1-C4 haloalkyl)amino group; a C2-C5 cyclic amino group; a hydroxyl group; and a hydrogen atom.

Examples of R$^8$ in "—OC(=O)R$^8$" include a C1-C4 alkyl group; a C1-C4 haloalkyl group; a C1-C4 alkoxy group; a C1-C4 haloalkoxy group; a C3-C6 alkenyloxy group; a C3-C6 haloalkenyloxy group; a C3-C6 alkynyloxy group; a C3-C6 haloalkynyloxy group; an amino group; a C1-C4 alkylamino group; a C1-C4 haloalkylamino group; a di(C1-C4 alkyl)amino group; a di(C1-C4 haloalkyl)amino group; a C2-C5 cyclic amino group; and a hydrogen atom.

Examples of the "optionally halogenated C1-C4 chain hydrocarbon group" as used herein include an optionally halogenated C1-C4 alkyl group, an optionally halogenated C2-C4 alkenyl group, and an optionally halogenated C2-C4 alkynyl group.

Examples of the "optionally halogenated C1-C4 alkyl group" as used herein include a methyl group, an ethyl group, a propyl group, a 1-methylethyl group (hereinafter may be referred to as an i-propyl group), a chloromethyl group, a fluoromethyl group, a difluoromethyl group, a trifluoromethyl group, a 2,2,2-trifluoroethyl group, a 1,1,2,2-tetrafluoroethyl group, a 1,1,2,2,2-pentafluoroethyl group, and a 1,1-dimethylethyl group (hereinafter may be referred to as a t-butyl group).

Examples of the "optionally halogenated C2-C4 alkenyl group" as used herein include a vinyl group, a 2,2-difluorovinyl group, a 1,2,2-trifluorovinyl group, a 1-propenyl group, a 2-propenyl group, a 3,3-difluoro-2-propenyl group, a 1-methyl-2-propenyl group, a 2-methyl-2-propenyl group, a 1-butenyl group, and a 2-butenyl group.

Examples of the "optionally halogenated C2-C4 alkynyl group" as used herein include an ethynyl group, a 1-propynyl group, a 3,3,3-trifluoro-1-propynyl group, a 2-propynyl group, a 1-methyl-2-propynyl group, a 1-butynyl group, a 2-butynyl group, and a 3-butynyl group.

Examples of the "optionally halogenated C1-C4 alkoxy group" as used herein include a methoxy group, an ethoxy group, a propoxy group, a trifluoromethoxy group, a bromodifluoromethoxy group, a difluoromethoxy group, a chlorodifluoromethoxy group, a pentafluoroethoxy group, a 2,2,2-trifluoroethoxy group, and a 1,1,2,2-tetrafluoroethoxy group.

Examples of the "optionally halogenated C3-C6 alkenyloxy group" as used herein include a 1-propenyloxy group, a 2-propenyloxy group, a 1-methyl-2-propenyloxy group; a 1,1-dimethyl-2-propenyloxy group, and a 2,2-difluoro-2-propenyloxy group.

Examples of the "optionally halogenated C3-C6 alkynyloxy group" as used herein include a 2-propynyloxy group, a 1-methyl-2-propynyloxy group, a 1,1-dimethyl-2-propynyloxy group, a 2-butynyloxy group, a 1-methyl-2-butynyloxy group, a 1,1-dimethyl-2-butynyloxy group, and a 3,3,3-trifluoro-1-propynyloxy group.

Examples of the "optionally halogenated C1-C4 alkylamino group" as used herein include an N-methylamino group, an N-ethylamino group, an N-propylamino group, an N-(1-methylethyl)amino group, and an N-(2,2,2-trifluoroethyl)amino group.

Examples of the "optionally halogenated di(C1-C4 alkyl) amino group" as used herein include an N,N-dimethylamino group, an N-ethyl-N-methylamino group, an N,N-diethylamino group, an N-methyl-N-propylamino group, an N-ethyl-N-propylamino group, an N,N-dipropylamino group, an N-methyl-N-(1-methylethyl)amino group, an N-ethyl-N-(1-methylethyl)amino group, an N,N-di(1-methylethyl)amino group, N-methyl-N-(2,2,2-trifluoroethyl)amino group, and an N-ethyl-N-(2,2,2-trifluoroethyl)amino group.

Examples of the "C2-C5 cyclic amino group" as used herein include a 1-aziridino group, a 1-azetidinyl group, a 1-pyrrolidinyl group, a piperidino group, and a morpholino group.

Examples of the "C1-C6 chain hydrocarbon group optionally substituted with a group selected from the group L" as used herein include a C1-C6 alkyl group, a C1-C6 alkyl group substituted with a group selected from the group L, a C2-C6 alkenyl group, a C2-C6 alkenyl group substituted with a group selected from the group L, a C2-C6 alkynyl group, and a C2-C6 alkynyl group substituted with a group selected from the group L.

Examples of the C1-C6 alkyl group and the C1-C6 alkyl group substituted with a group selected from the group L include an optionally halogenated C1-C6 alkyl group, such as a methyl group, an ethyl group, a propyl group, a 1-methylethyl group, a 2,2-dimethylpropyl group, a chloromethyl group, a fluoromethyl group, a difluoromethyl group, a trifluoromethyl group, a 2,2,2-trifluoroethyl group, a 1,1,2,2-tetrafluoroethyl group, a 1,1,2,2,2-pentafluoroethyl group, and a 1,1-dimethylethyl group; an optionally halogenated (C1-C4 alkoxy)C1-C4 alkyl group, such as a methoxymethyl group, an ethoxymethyl group, a 1-methoxyethyl group, a 1-ethoxyethyl group, and a trifluoromethoxymethyl group; an optionally halogenated (C3-C6 alkenyloxy)C1-C4 alkyl group, such as a (1-propenyloxy)methyl group, a (2-propenyloxy)methyl group, a (1-methyl-2-propenyloxy)methyl group, a (1,1-dimethyl-2-propenyloxy)methyl group, a (2,2-difluoro-2-propenyloxy)methyl group, a 1-(1-propenyloxy)ethyl group, a 1-(2-propenyloxy)ethyl group, a 1-(1-methyl-2-propenyloxy)ethyl group, a 1-(1,1-dimethyl-2-propenyloxy)ethyl group, a 1-(2,2-difluoro-2-propenyloxy)ethyl group, a 2-(1-propenyloxy)ethyl group, a 2-(2-propenyloxy)ethyl group, a 2-(1-methyl-2-propenyloxy) ethyl group, a 2-(1,1-dimethyl-2-propenyloxy)ethyl group, and a 2-(2,2-difluoro-2-propenyloxy)ethyl group;

an optionally halogenated (C3-C6 alkynyloxy)C1-C4 alkyl group, such as a (2-propynyloxy)methyl group, a (1-methyl-2-propynyloxy)methyl group, a (1,1-dimethyl-2-propynyloxy)methyl group, a (2-butynyloxy)methyl group, a (1-methyl-2-butynyloxy)methyl group, a (1,1-dimethyl-2-butynyloxy)methyl group, a (3,3,3-trifluoro-1-propynyloxy) methyl group, a 1-(2-propynyloxy)ethyl group, a 1-(1-methyl-2-propynyloxy)ethyl group, a 1-(1,1-dimethyl-2-propynyloxy)ethyl group, a 1-(2-butynyloxy)ethyl group, a 1-(1-methyl-2-butynyloxy)ethyl group, a 1-(1,1-dimethyl-2-butynyloxy)ethyl group, a 1-(3,3,3-trifluoro-1-propynyloxy) ethyl group, a 2-(2-propynyloxy)ethyl group, a 2-(1-methyl-2-propynyloxy)ethyl group, a 2-(1,1-dimethyl-2-propynyloxy)ethyl group, a 2-(2-butynyloxy)ethyl group, a 2-(1-methyl-2-butynyloxy)ethyl group, a 2-(1,1-dimethyl-2-butynyloxy)ethyl group, and a 2-(3,3,3-trifluoro-1-propynyloxy)ethyl group; and an optionally halogenated (hydroxy) C1-C4 alkyl group, such as a hydroxymethyl group, a 1-hydroxyethyl group, a 1-hydroxy-1-methylethyl group, a 2-hydroxyethyl group, and a 2-hydroxy-1-methylethyl group.

Examples of the C2-C6 alkenyl group and the C2-C6 alkenyl group substituted with a group selected from the group L include an optionally halogenated C2-C6 alkenyl group, such as a vinyl group, a 2,2-difluorovinyl group, a 1,2,2-trifluorovinyl group, a 1-propenyl group, a 2-propenyl group, a 3,3-difluoro-2-propenyl group, and a 1-methyl-2-propenyl group.

Examples of the C2-C6 alkynyl group and the C2-C6 alkynyl group substituted with a group selected from the group L include a 1-ethynyl group, and an ethynyl group substituted with a group selected from the group L, such as a 2-bromoethynyl group, a 2-iodoethynyl group, and a 2-(methoxycarbonyl)ethynyl group;

a 1-propynyl group, and a 1-propynyl group substituted with a group selected from the group L, such as a 3-fluoro-1-propynyl group, a 3,3-difluoro-1-propynyl group, a 3-(dimethylamino)-1-propynyl group, a 3,3,3-trifluoro-1-propynyl group, a 3-methoxy-1-propynyl group, and a 3-(methoxycarbonyl)-1-propynyl group;

a 2-propynyl group, and a 2-propynyl group substituted with a group selected from the group L, such as a 1-fluoro-2-propynyl group and a 1,1-difluoro-2-propynyl group;

a 1-butynyl group, and a 1-butynyl group substituted with a group selected from the group L, such as a 4-fluoro-1-butynyl group, a 4-methoxy-1-butynyl group, a 4-(dimethylamino)-1-butynyl group, and a 4-(methoxycarbonyl)-1-butynyl group;

a 2-butynyl group, and 2-butynyl group substituted with a group selected from the group L, such as a 4-fluoro-2-butynyl group, a 4-methoxy-2-butynyl group, a 4-(dimethylamino)-2-butynyl group, and a 4-(methoxycarbonyl)-2-butynyl group;

a 3-butynyl group, and a 3-butynyl group substituted with a group selected from the group L, such as a 1,1-difluoro-3-butynyl group;

a 1-pentynyl group, and a 1-pentynyl group substituted with a group selected from the group L, such as a 5-fluoro-1-pentynyl group, a 5-methoxy-1-pentynyl group, a 5-(dimethylamino)-1-pentynyl group, and a 5-(methoxycarbonyl)-1-pentynyl group; and a 2-pentynyl group, and a 2-pentynyl group substituted with a group selected from the group L, such as a 5-fluoro-2-pentynyl group, a 5-methoxy-2-pentynyl group, a 5-(dimethylamino)-2-pentynyl group, and a 5-(methoxycarbonyl)-2-pentynyl group.

Examples of a group represented by "—N($R^9$)$R^{10}$" include an N-methylamino group, an N-ethylamino group, an N-propylamino group, an N-(1-methylethyl)amino group, an N-(2,2,2-trifluoroethyl)amino group, an N-(2-propenyl)amino group, an N-(2-propynyl)amino group, an N-(2-butynyl)amino group, an N-(3-butynyl group)amino group, an N-(2-pentynyl group)amino group, an N,N-dimethylamino group, an N-ethyl-N-methylamino group, an N,N-diethylamino group, an N-methyl-N-propylamino group, an N-ethyl-N-propylamino group, an N,N-dipropylamino group, an N-methyl-N-(1-methylethyl)amino group, an N-ethyl-N-(1-methylethyl)amino group, an N,N-di(1-methylethyl)amino group, N-methyl-N-(2,2,2-trifluoroethyl)amino group, an N-(2-propenyl)amino group, an N-methyl-N-(2-propynyl)amino group, a N-(2-butynyl)-N-methylamino group, a N-(3-butynyl group)-N-methylamino group, an N-methyl-N-(2-pentynyl group)amino group and an N-ethyl-N-(2,2,2-trifluoroethyl)amino group.

Examples of the "optionally halogenated C3-C6 alkenyl group" as used herein include a 2-propenyl group, a 3,3-dichloro-2-propenyl group, 3,3-difluoro-2-propenyl group, a 1-methyl-2-propenyl group, a 2-methyl-2-propenyl group, a 1-butenyl group, and a 2-butenyl group.

Examples of the "optionally halogenated C3-C6 alkynyl group" as used herein include a 2-propynyl group, and a halogenated 2-propynyl group, such as a 1-fluoro-2-propynyl group and a 1,1-difluoro-2-propynyl group;
a 2-butynyl group, and a halogenated 2-butynyl group, such as a 4-fluoro-2-butynyl group;
a 3-butynyl group, and a halogenated group, such as a 1,1-difluoro-3-butynyl group;
a 2-pentynyl group, and a halogenated 2-pentynyl group, such as a 5-fluoro-2-pentynyl group.

Examples of the "optionally halogenated phenyl group" as used herein include a phenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, 3,4-dichlorophenyl group, a 3,5-dichlorophenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2-bromophenyl group, a 3-bromophenyl group, a 4-bromophenyl group, a 2,3-dibromophenyl group, a 2,4-dibromophenyl group, a 2,5-dibromophenyl group, a 2,6-dibromophenyl group, a 3,4-dibromophenyl group, and a 3,5-dibromophenyl group.

Examples of the "C1-C5 haloalkyl group containing at least one fluorine atom" include a C1-C5 alkyl group substituted with only a fluorine atom(s), such as a fluoromethyl group, a difluoromethyl group, a trifluoromethyl group, a 1,1,2,2,2-pentafluoroethyl group, a 2,2,2-trifluoroethyl group, a 1,1-difluoroethyl group, a 1,1,2,2,3,3,3-heptafluoropropyl group, a 1,1-difluoropropyl group, a 2,2-difluoropropyl group, a 3,3,3-trifluoropropyl group, a 1,1,2,2,3,3,4,4,4-nonafluorobutyl group, a 1,1-difluorobutyl group, a 2,2-difluorobutyl group, a 1,1,2,2,3,3,4,4,5,5,5-undecafluoropentyl group, a 1,1-difluoropentyl group, or a 2,2-difluoropentyl group; a C1-C5 alkyl group substituted with a fluorine atom(s) and a chlorine atom(s), such as a chlorodifluoromethyl group, a 1,2-dichloro-1,2,2-trifluoroethyl group, a 1,1-dichloro-2,2,2-trifluoroethyl group, a 1-chloro-1,3,3,3-tetrafluoropropyl group, a 2,3-dichloro-2,3,3-trifluoropropyl group, or a 2,2-dichloro-3,3,3-trifluoropropyl group; and a C1-C5 alkyl group substituted with a fluorine atom(s) and a bromine atom(s), such as a 2,2-dibromo-3,3,3-trifluoropropyl group, a 2-bromo-3,3,3-trifluoropropyl group, a 2,3-dibromo-3,3-difluoropropyl group, a 3-bromo-3,3-difluoropropyl group, a 1-bromo-1,3,3,3-tetrafluoropropyl group, a 1-bromo-2,2,3,3,3-pentafluoropropyl group, a 1,3-dibromo-2,2,3,3-tetrafluoropropyl group, a 3-bromo-2,3,3-trifluoropropyl group, a 3-bromo-2,2,3,3-tetrafluoropropyl group, a 2,3-dibromo-2,3,3-trifluoropropyl group, or a 3-bromo-3,3-difluoropropyl group.

Examples of the compound of the present invention include:
a compound of the formula (I), wherein A is an oxolanyl group, a thiolanyl group, an oxanyl group, a thianyl group, a dioxolanyl group, a dithiolanyl group, a 1,3-dioxanyl group, a 1,4-dioxanyl group, a 1,3-dithianyl group, or a 1,4-dithianyl group;
a compound of the formula (I), wherein A is an oxolanyl group optionally substituted with a group selected from the group E1;
a compound of the formula (I), wherein A is a thiolanyl group optionally substituted with a group selected from the group E1;
a compound of the formula (I), wherein A is an oxanyl group optionally substituted with a group selected from the group E1;
a compound of the formula (I), wherein A is a thianyl group optionally substituted with a group selected from the group E1;
a compound of the formula (I), wherein A is a dioxolanyl group optionally substituted with a group selected from the group E1;
a compound of the formula (I), wherein A is a dithiolanyl group optionally substituted with a group selected from the group E1;
a compound of the formula (I), wherein A is a 1,3-dioxanyl group optionally substituted with a group selected from the group E1;
a compound of the formula (I), wherein A is a 1,4-dioxanyl group optionally substituted with a group selected from the group E1;
a compound of the formula (I), wherein A is a 1,3-dithianyl group optionally substituted with a group selected from the group E1;
a compound of the formula (I), wherein A is a 1,4-dithianyl group optionally substituted with a group selected from the group E1;
a compound of the formula (I), wherein m is 0;
a compound of the formula (I), wherein m is 1;
a compound of the formula (I), wherein $R^1$ is a halogen atom or a hydrogen atom;
a compound of the formula (I), wherein $R^2$ is —C(=G)$R^5$ (in which G and $R^5$ each are as defined above) or a cyano group;
a compound of the formula (I), wherein $R^2$ is a cyano group;
a compound of the formula (I), wherein $R^1$ is a halogen atom or a hydrogen atom, and $R^2$ is —C(=G)$R^5$ (in which G and $R^5$ each is as defined above) or a cyano group;
a compound of the formula (I), wherein $R^1$ is a halogen atom or a hydrogen atom, and $R^2$ is —C(=G)$R^5$ (in which G and $R^5$ each are as defined above);
a compound of the formula (I), wherein $R^1$ is a halogen atom or a hydrogen atom, and $R^2$ is a cyano group;
a compound of the formula (I), wherein $R^1$ is an optionally halogenated C1-C4 chain hydrocarbon group, and $R^2$ is —C(=G)$R^5$ (in which G and $R^5$ each are as defined above) or a cyano group;

a compound of the formula (I), wherein $R^1$ is an optionally halogenated C1-C4 chain hydrocarbon group, and $R^2$ is a cyano group;
a compound of the formula (I), wherein $R^1$ is a methyl group, and $R^2$ is —C(=G)$R^5$ (in which G and $R^5$ each are as defined above) or a cyano group;
a compound of the formula (I), wherein $R^1$ is a methyl group, and $R^2$ is a cyano group;
a compound of the formula (I), wherein $R^1$ is a chlorine atom, and $R^2$ is —C(G)$R^5$ (in which G and $R^5$ each are as defined above) or a cyano group;
a compound of the formula (I), wherein $R^1$ is a chlorine atom, and $R^2$ is a cyano group;
a compound of the formula (I), wherein $R^1$ is an optionally halogenated C1-C4 chain hydrocarbon group, and $R^2$ is —C(=G)$R^5$ (in which G and $R^5$ each are as defined above) or a cyano group;
a compound of the formula (I), wherein $R^5$ is an optionally halogenated C1-C4 chain hydrocarbon group;
a compound of the formula (I), wherein $R^{1a}$ is a halogen atom or a hydrogen atom;
a compound of the formula (I), wherein $R^{2a}$ is —C(=G)$R^5$ (in which G and $R^5$ each are as defined above) or a cyano group;
a compound of the formula (1), wherein $R^{2a}$ is a cyano group;
a compound of the formula (I), wherein $R^{1a}$ is a halogen atom or hydrogen atom, and $R^{2a}$ is —C(=G)$R^5$ (in which G and $R^5$ each are as defined above) or a cyano group;
a compound of the formula (I), wherein $R^{1a}$ is a halogen atom or a hydrogen atom, and $R^{2a}$ is —C(=G)$R^5$ (in which G and $R^5$ each are as defined above);
a compound of the formula (I), wherein $R^{1a}$ is a halogen atom or a hydrogen atom, and $R^{2a}$ is a cyano group;
a compound of the formula (I), wherein $R^{1a}$ is an optionally halogenated C1-C4 chain hydrocarbon group, and $R^{2a}$ is —C(=G)$R^5$ (in which G and $R^5$ each are as defined above) or a cyano group;
a compound of the formula (I), wherein $R^{1a}$ is an optionally halogenated C1-C4 chain hydrocarbon group, and $R^{2a}$ is a cyano group;
a compound of the formula (I), wherein $R^{1a}$ is a methyl group, and $R^{2a}$ is —C(=G)$R^5$ (in which G and $R^5$ each are as defined above) or a cyano group;
a compound of the formula (I), wherein $R^{1a}$ is a methyl group, and $R^{2a}$ is a cyano group;
a compound of the formula (I), wherein $R^{1a}$ is a chlorine atom, and $R^{2a}$ is —C(=G)$R^5$ (in which G and $R^5$ each are as defined above) or a cyano group;
a compound of the formula (I), wherein $R^{1a}$ is a chlorine atom, and $R^{2a}$ is a cyano group;
a compound of the formula (I), wherein $R^{1a}$ is an optionally halogenated C1-C4 chain hydrocarbon group, and $R^{2a}$ is —C(=G)$R^5$ (in which G and $R^5$ each are as defined above) or a cyano group;
a compound of the formula (I), wherein $R^{2a}$ is —C(=G)$R^5$ (in which G is as defined above, and $R^5$ is an optionally halogenated C1-C4 chain hydrocarbon group);
a compound of the formula (I), wherein m is 0, n is 0, $R^1$, $R^2$, $R^{1a}$ and $R^{2a}$ independently represent a C1-C4 alkyl group, a halogen atom or a hydrogen atom, A is a C2-C4 alkynyl group, or a 5- or 6-membered saturated heterocyclic group optionally substituted with a (C1-C3 alkoxy)carbonyl group, and Q is a C2-C4 fluoroalkyl group; and
a compound of the formula (I), wherein m is 0, n is 0, $R^1$, $R^2$, $R^{1a}$ and $R^{2a}$ independently represent a C1-C4 alkyl group, a halogen atom or a hydrogen atom, A is an oxolanyl group, a thiolanyl group, an oxanyl group, a thianyl group, a dioxola-nyl group, a 1,3-dioxanyl group, a 1,4-dioxanyl group, or a 1,4-dithianyl group, and Q is a C2-C4 fluoroalkyl group.

Then, a process for producing the compound of the present compound is explained.

Hereinafter, a compound represented by the formula ($\alpha$) ($\alpha$=arbitrary symbol) may be referred to as a "compound ($\alpha$)".

Production Process 1

Among compounds of the present invention, a compound represented by a formula (I-a) can be produced, for example, by a process shown below:

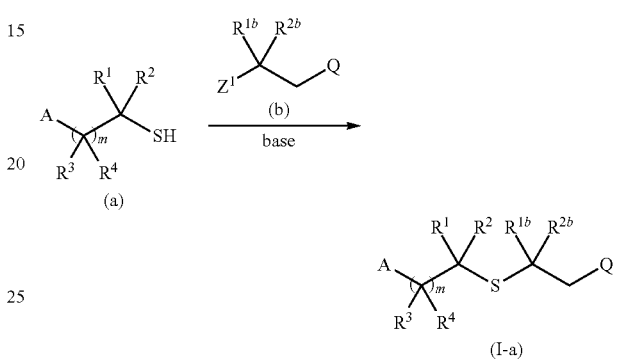

wherein $R^{1b}$ represents an optionally halogenated C1-C4 chain hydrocarbon group, or a hydrogen atom, $R^{2b}$ represents a C1-C4 chain hydrocarbon group, —C(=G)$R^5$, a cyano group, or a hydrogen atom, $Z^1$ represents a leaving group such as a chlorine atom, a bromine atom, an iodine atom, a methanesulfonyl group, or a p-toluenesulfonyl group, and A, Q, $R^1$, $R^2$, $R^3$, $R^4$, $R^5$, G and m are as defined above.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

The reaction is usually carried out in the presence of a base.

Examples of the base include inorganic bases such as sodium hydride, sodium hydroxide, potassium hydroxide, and potassium carbonate; alkali metal alkoxides such as sodium methoxide and potassium tert-butoxide; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (a).

The amount of the compound (b) is usually from 1 to 10 mol per on 1 mol of the compound (a).

The reaction temperature is usually within a range from −50 to 100° C., and the reaction time is usually within a range from 1 to 24 hours.

After completion of the reaction, the compound (I-a) can be isolated, for example, by pouring the reaction mixture into water and extracting the mixture with an organic solvent, followed by concentration. The isolated compound (I-a) can be further purified by chromatography, recrystallization or the like.

The compound (I-a) can also be produced in accordance with a known production process.

Production Process 2

Among compounds of the present invention, a compound represented by a formula (I-b) can be produced by a process shown below:

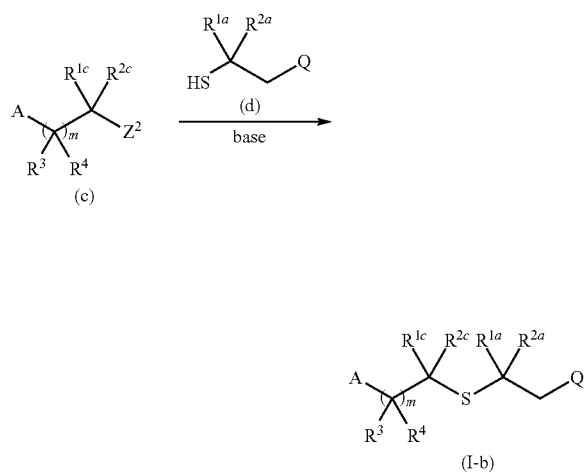

(I-b)

wherein $R^{1c}$ represents a C1-C4 chain hydrocarbon group or a hydrogen atom, $R^{2c}$ represents a C1-C4 chain hydrocarbon group, —C(=G)$R^5$, a cyano group, or a hydrogen atom, $Z^2$ represents a leaving group such as a chlorine atom, a bromine atom, an iodine atom, a methanesulfonyl group, or a p-toluenesulfonyl group, and A, Q, $R^{1a}$, $R^{2a}$, $R^3$, $R^4$, $R^5$, G and m are as defined above.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

The reaction is usually carried out in the presence of a base.

Examples of the base include inorganic bases such as sodium hydride, sodium hydroxide, potassium hydroxide, and potassium carbonate; alkali metal alkoxides such as sodium methoxide and potassium tert-butoxide; and organic bases such as triethylamine, 1,4-diazabicyclo[2.2.2]octane, and 1,8-diazabicyclo[5.4.0]-7-undecene.

The amount of the base to be used is usually from 1 to 10 mol per on 1 mol of the compound (d).

The amount of the compound (c) is usually from 1 to 10 mol per 1 mol of the compound (d).

The reaction temperature is usually within a range from −50 to 100° C., and, the reaction time is usually within a range from 1 to 24 hours.

After completion of the reaction, the compound (I-b) can be isolated, for example, by pouring the reaction mixture into water and extracting the mixture with an organic solvent, followed by concentration. The isolated compound (I-b) can be further purified by chromatography, recrystallization or the like.

Production Process 3

Among compounds of the present invention, a compound represented by the formula (I-g) can be produced from the compound (c) by a process shown below:

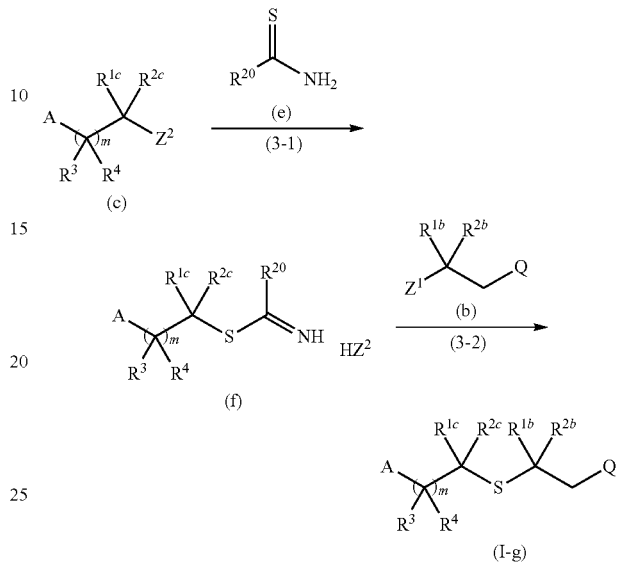

(I-g)

wherein $R^{20}$ represents a methyl group or an amino group, and A, Q, $R^{1b}$, $R^{1c}$, $R^{2b}$, $R^{2c}$, $R^3$, $R^4$, m, $Z^1$ and $Z^2$ are as defined above.

Step (3-1)

The compound (f) can be produced by reacting the compound (c) with the compound (e).

The reaction is usually carried out in the presence of a solvent.

Examples of the solvent include halogenated hydrocarbons such as dichloromethane and chloroform; alcohols such as methanol and ethanol; and their mixtures.

The amount of the compound (e) is usually from 1 to 3 mol per 1 mol of the compound (c).

The reaction temperature is usually within a range from 20 to 200° C., and the reaction time is usually within a range from 0.5 to 240 hours.

After completion of the reaction, the compound (f) can be isolated, for example, by concentration of the reaction mixture. The isolated compound (f) can be used in the step (3-2) without purification, or can be further purified by recrystallization or the like, if necessary.

Step (3-2)

The compound (I-g) can be produced by reacting the compound (f) with the compound (b) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydroxide and potassium hydroxide; and alkali metal alkoxides such as sodium methoxide and potassium tert-butoxide.

The amount of the base to be used is usually from 1 to 50 mol per 1 mol of the compound (f).

The amount of the compound (b) usually from 1 to 10 mol per 1 mol of the compound (f).

The reaction can be carried out using a phase transfer catalyst such as tetra n-butylammonium bromide, if necessary. The amount of the phase transfer catalyst is usually from 0.05 to 1.0 mol per 1 mol of the compound (f).

The reaction temperature is usually within a range from −50 to 100° C., and the reaction time is usually within a range from 1 to 24 hours.

After completion of the reaction, the compound (I-g) can be isolated, for example, by pouring the reaction mixture into water and extracting the mixture with an organic solvent, followed by concentration. The isolated compound (I-g) can be further purified by chromatography, recrystallization or the like.

Production Process 4

Among compounds of the present invention, a compound represented by the formula (I-g) can be also produced by a process shown below:

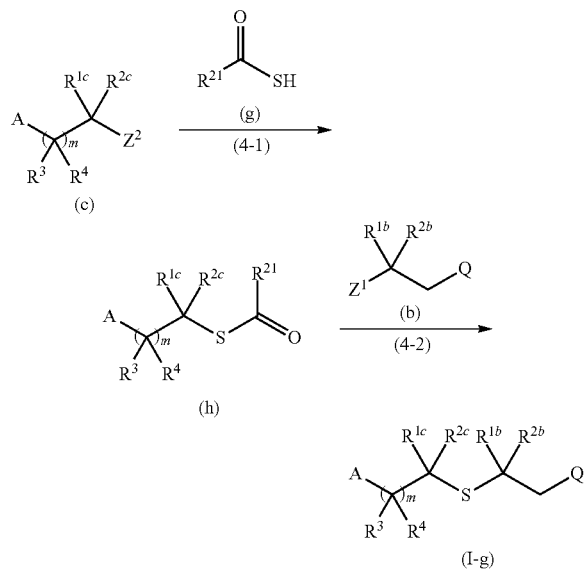

wherein $R^{21}$ represents a methyl group or a phenyl group, and A, Q, $R^{1b}$, $R^{1c}$, $R^{2b}$, $R^{2c}$, $R^3$, $R^4$, m, $Z^1$ and $Z^2$ are as defined above.

Step (4-1)

The compound (h) can be produced by reacting the compound (c) with the compound (g) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydride and potassium carbonate; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (c).

The amount of the compound (g) usually from 1 to 5 mol per 1 mol of the compound (c).

The reaction temperature is usually within a range from −20 to 80° C., and the reaction time is usually within a range from 1 to 24 hours.

After completion of the reaction, the compound (h) can be isolated, for example, by pouring the reaction mixture into acidic water (e.g., dilute hydrochloric acid) and extracting the mixture with an organic solvent, followed by concentration. The isolated compound (h) can be further purified by chromatography, recrystallization or the like.

Step (4-2)

The compound (I-g) can be produced by reacting the compound (b) with the compound (h) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydroxide and potassium hydroxide; and alkali metal alkoxides such as sodium methoxide, sodium ethoxide and potassium tert-butoxide.

The amount of the base to be used is usually from 1 to 10 mol per 1 mol of the compound (h).

The amount of the compound (b) is usually from 1 to 10 mol per 1 mol of the compound (h).

The reaction temperature is within a range from −50 to 100° C., and the reaction time is usually within a range from 1 to 24 hours.

After completion of the reaction, the compound (I-g) can be isolated, for example, by pouring the reaction mixture into water and extracting the mixture with an organic solvent, followed by concentration. The isolated compound (I-g) can be further purified by chromatography, recrystallization or the like.

Production Process 5

Among compounds of the present invention, a compound represented by the formula (I-g) can be also produced, for example, by a process shown below:

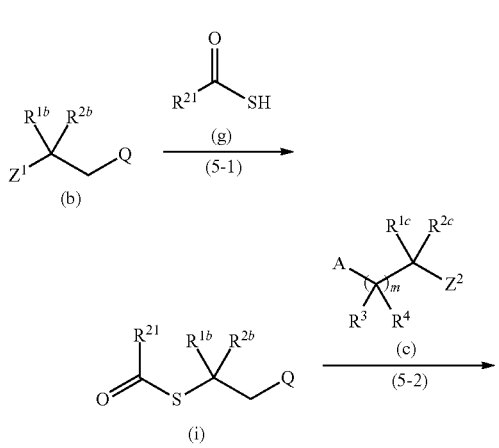

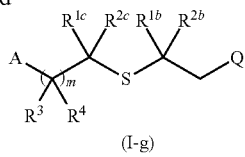

(I-g)

wherein A, Q, $R^{1c}$, $R^{1b}$, $R^{2c}$, $R^{2b}$, $R^3$, $R^4$, $R^{21}$, m, $Z^1$ and $Z^2$ are as defined above.

Step (5-1)

The compound (i) can be produced by reacting the compound (b) with the compound (g) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydride and potassium carbonate; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (b).

The amount of the compound (g) usually from 1 to 5 mol per 1 mol of the compound (b).

The reaction temperature is usually within a range from −20 to 80° C., and the reaction time is usually within a range from 1 to 24 hours.

After completion of the reaction, the compound (i) can be isolated, for example, by pouring the reaction mixture into acidic water (e.g., dilute hydrochloric acid) and extracting the mixture with an organic solvent, followed by concentration. The isolated compound (i) can be further purified by chromatography, recrystallization or the like.

Step (5-2)

The compound (I-g) can be produced by reacting the compound (c) with the compound (i) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydroxide and potassium hydroxide; and alkali metal alkoxides such as sodium methoxide, sodium ethoxide and potassium tert-butoxide.

The amount of the base to be used is usually from 1 to 10 mol per 1 mol of the compound (i).

The amount of the compound (c) is usually from 1 to 10 mol per 1 mol of the compound (i).

The reaction temperature is within a range from −50 to 100° C., the reaction time is usually within a range from 1 to 24 hours.

After completion of the reaction, the compound (I-g) can be isolated, for example, by pouring the reaction mixture into water and extracting the mixture with an organic solvent, followed by concentration. The isolated compound (I-g) can be further purified by chromatography, recrystallization or the like.

Production Process 6

Among compounds of the present invention, a compound represented by a formula (I-c) can be produced by a process shown below:

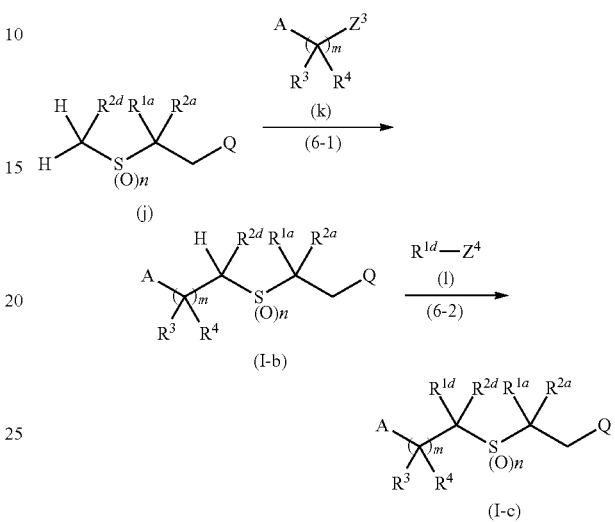

wherein $R^{1d}$ represents an optionally halogenated C1-C4 chain hydrocarbon group, $R^{2d}$ represents —C(=O)$R^5$ or a cyano group, $Z^3$ and $Z^4$ independently represent a leaving group such as a chlorine atom, a bromine atom, an iodine atom, a methanesulfonyl group, or a p-toluenesulfonyl group, and A, Q, $R^{1a}$, $R^{2a}$, $R^3$, $R^4$, $R^5$, n and m are as defined above.

Step (6-1)

The compound represented by the formula (I-b) can be produced by reacting the compound (k) with the compound (j) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydride, sodium hydroxide, potassium hydroxide, and potassium carbonate; alkali metal alkoxides such as sodium methoxide and potassium tert-butoxide; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (j).

The compound (k) is usually from 1 to 10 mol per 1 mol of the compound (j).

The reaction temperature is usually within a range from −50 to 100° C., and the reaction time is usually within a range from 1 to 24 hours.

After completion of the reaction, the compound (I-b) can be isolated, for example, by pouring the reaction mixture into water and extracting the mixture with an organic solvent, followed by concentration. The isolated compound (I-b) can be further purified by chromatography, recrystallization or the like.

Step (6-2)

The compound (I-c) can be produced by reacting the compound (l) with the compound (I-b) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydride, sodium hydroxide, potassium hydroxide, and potassium carbonate; alkali metal alkoxides such as sodium methoxide and potassium tert-butoxide; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (I-b).

The amount of the compound (l) is usually from 1 to 10 mol per 1 mol of the compound (I-b).

The reaction temperature is usually within a range from −50 to 100° C., and, the reaction time is usually within a range from 1 to 24 hours.

After completion of the reaction, the compound (I-c) can be isolated, for example, by pouring the reaction mixture into water and extracting the mixture with an organic solvent, followed by concentration. The isolated compound (I-c) can be further purified by chromatography, recrystallization or the like.

Production Process 7

Among compounds of the present invention represented, the compound (I-c) can also be produced from the compound (j) by a process shown below:

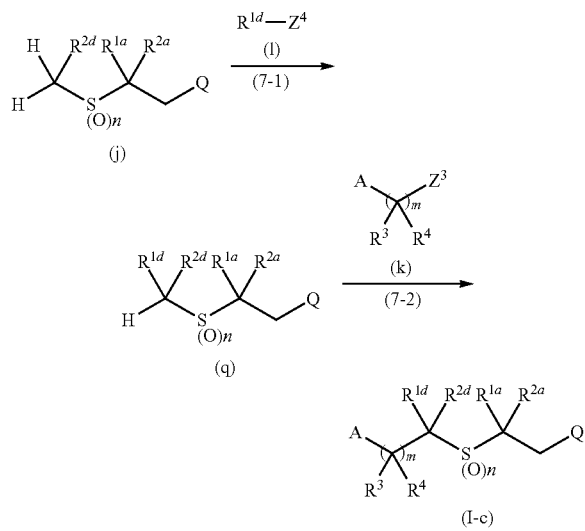

wherein A, Q, $R^1$, $R^{1a}$, $R^{1d}$, $R^{2a}$, $R^{2d}$, $R^3$, $R^4$, n, m, $Z^3$ and $Z^4$ are as defined above.

Step (7-1)

The compound (q) can be produced by reacting the compound (l) with the compound (j) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydride, sodium hydroxide, potassium hydroxide, and potassium carbonate; alkali metal alkoxides such as sodium methoxide and potassium tert-butoxide; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (j).

The amount of the compound (l) is usually from 1 to 10 mol per 1 mol of the compound (j).

The reaction temperature is usually within a range from −50 to 100° C., and, the reaction time is usually within a range from 1 to 24 hours.

After completion of the reaction, the compound (q) can be isolated, for example, by pouring the reaction mixture into water and extracting the mixture with an organic solvent, followed by concentration. The isolated compound (q) can be further purified by chromatography, recrystallization or the like, if necessary.

Step (7-2)

The compound represented by the formula (I-c) can be produced by reacting the compound (k) with the compound (q) in the presence of a base.

The reaction is usually carried out in the presence of a solvent.

Examples of the solvent include ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and their mixtures.

Examples of the base include inorganic bases such as sodium hydride, sodium hydroxide, potassium hydroxide, and potassium carbonate; alkali metal alkoxides such as sodium methoxide and potassium tert-butoxide; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (q).

The amount of the compound (k) is usually from 1 to 10 mol per 1 mol of the compound (q).

The reaction temperature is usually within a range from −50 to 100° C., and the reaction time is usually within a range from 1 to 24 hours.

After completion of the reaction, the compound (I-c) can be isolated, for example, by pouring the reaction mixture into water and extracting the mixture with an organic solvent, followed by concentration. The isolated compound (I-c) can be further purified by chromatography, recrystallization or the like, if necessary.

Production Process 8

Among compounds of the present invention, a compound represented by the formula (I-d) can be produced by a process shown below:

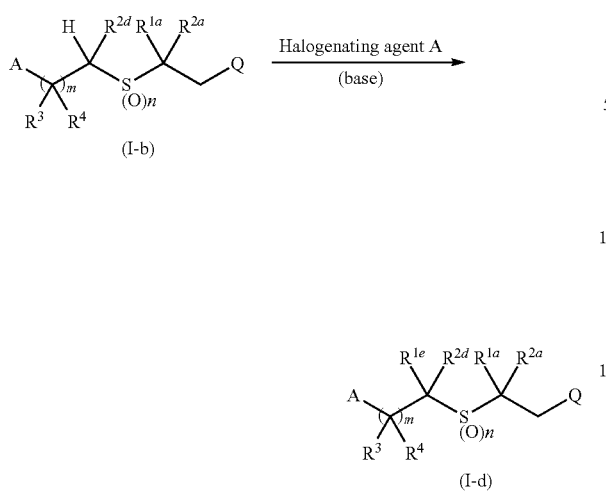

wherein $R^{1e}$ represents a halogen atom, and A, Q, $R^{1a}$, $R^2$, $R^{2a}$, $R^{2d}$, $R^3$, $R^4$, n and m are as defined above.

The reaction between the compound (I-b) and the halogenating agent A is usually carried out in the presence of a solvent.

Examples of the solvent include acid amides such as N,N-dimethylformamide; ethers such as diethyl ether and tetrahydrofuran; organosulphurs such as dimethyl sulfoxide and sulfolane; halogenated hydrocarbons such as chloroform, carbon tetrachloride, 1,2-dichloroethane, dichloromethane, and dichlorobenzene; aliphatic nitriles such as acetonitrile and propionitrile; aromatic hydrocarbons such as toluene and xylene; water; and their mixtures.

The reaction may be carried out in the presence of a base.

Examples of the base include inorganic bases such as sodium hydride, sodium hydroxide, potassium hydroxide, and potassium carbonate; alkali metal alkoxides such as sodium methoxide and potassium tert-butoxide; alkali metal amides such as lithium diisopropylamide; and organic bases such as triethylamine, 1,4-diazabicyclo[2.2.2]octane, and 1,8-diazabicyclo[5.4.0]-7-undecene.

The amount of the base to be used is usually from 1 to 10 mol per 1 mol of the compound (I-b).

Examples of the halogenating agent A include halogenated hydrocarbons such as carbon tetrachloride and hexachloroethane; halogens such as fluorine, chlorine, bromine, and iodine; N-halogenated succinimides such as N-chlorosuccinimide, N-bromosuccinimide, and N-iodosuccinimide; N-fluoropyridinium salts such as 1-fluoro-2,4,6-trimethylpyridinium trifluoromethanesulfonate and 1,1'-difluoro-2,2'-bipyridinium bistetrafluoroborate; and inorganic salts such as copper(II) chloride and copper(II) bromide.

The amount of the halogenating agent A is usually from 1 to 10 mol per 1 mol of the compound (I-b).

The reaction temperature is usually within a range from −100 to 100° C., and the reaction time is usually within a range from 1 to 24 hours.

After completion of the reaction, the compound (I-d) can be isolated, for example, by pouring the reaction mixture into water and extracting the mixture with an organic solvent, followed by concentration. The isolated compound (I-d) can be further purified by chromatography, recrystallization or the like, if necessary.

Production Process 9

Among compounds of the present invention, the compound (I-d) can be also produced by a process shown below:

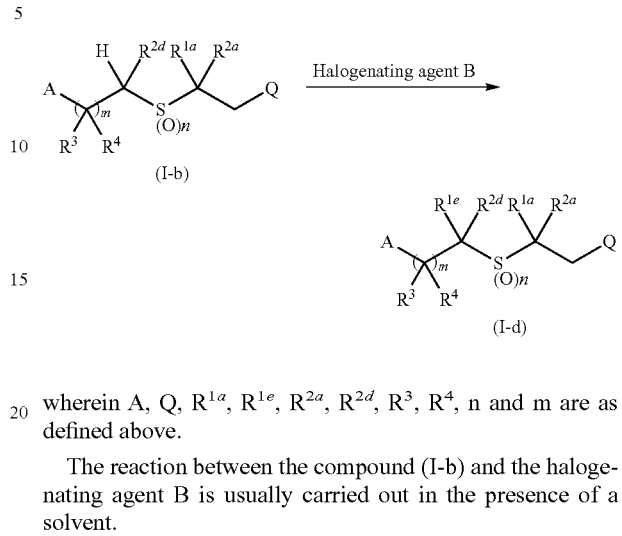

wherein A, Q, $R^{1a}$, $R^{1e}$, $R^{2a}$, $R^{2d}$, $R^3$, $R^4$, n and m are as defined above.

The reaction between the compound (I-b) and the halogenating agent B is usually carried out in the presence of a solvent.

Examples of the solvent include halogenated hydrocarbons such as chloroform, carbon tetrachloride, 1,2-dichloroethane, dichloromethane, and dichlorobenzene; aliphatic nitriles such as acetonitrile and propionitrile; aromatic hydrocarbons such as toluene and xylene; aliphatic carboxylic acids such as acetic acid; carbon disulfide; water; and their mixtures.

Examples of the halogenating agent B include halogens such as fluorine, chlorine, bromine, and iodine; hydrogen halides such as hydrogen fluoride, hydrogen chloride, hydrogen bromide, and hydrogen iodide; halogenated sulfur compounds such as thionyl chloride, thionyl bromide, and sulfuryl chloride; and halogenated phosphorus compounds such as phosphorus trichloride, phosphorus tribromide, phosphorus pentachloride, and phosphorus oxychloride.

The amount of the halogenating agent B is usually from 1 to 10 mol per 1 mol of the compound (I-b).

The reaction temperature is usually within a range from −100 to 200° C., and the reaction time is usually within a range from 1 to 24 hours.

After completion of the reaction, the compound (I-d) can be isolated, for example, by pouring the reaction mixture into water and extracting the mixture with an organic solvent, followed by concentration. The isolated compound (I-d) can be further purified by chromatography, recrystallization or the like, if necessary.

Production Process 10

Among compounds of the present invention, a compound (I-i) can be produced by a process shown below:

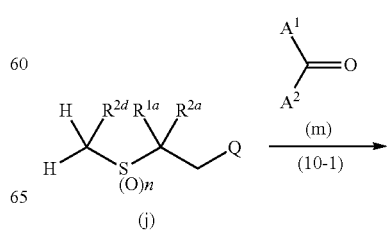

-continued $$\underset{A^2}{\overset{A^1}{>}}=\underset{S(O)_n}{\overset{R^{2d}}{\underset{|}{C}}}\underset{}{\overset{R^{1a}}{\underset{|}{C}}}\underset{}{\overset{R^{2a}}{\underset{|}{C}}}-Q \xrightarrow{\text{Hydride reducing agent}} $$

(I-h)

(10-2)

$$\underset{A^2}{\overset{A^1}{>}}\underset{H}{\overset{H}{<}}-\underset{S(O)_n}{\overset{R^{2d}}{\underset{|}{C}}}\underset{}{\overset{R^{1a}}{\underset{|}{C}}}\underset{}{\overset{R^{2a}}{\underset{|}{C}}}-Q$$

(I-i)

wherein $A^1$ and $A^2$ are taken together with the carbon atom to which they are attached to form a 3- to 8-membered saturated heterocyclic group, and Q, $R^{1a}$, $R^{2a}$, $R^{2d}$, $R^3$, $R^4$, $R^5$, n and m are as defined above.

Step (10-1)

The compound (I-h) can be produced by reacting the compound (j) with the compound (m).

The reaction is usually carried out in the presence of a solvent.

Examples of the solvent include alcohols such as methanol, ethanol and 2-propanol; ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; carboxylic acid such as formic acid and acetic acid; water; and their mixtures.

If necessary, the reaction is carried out in the presence of an acid or a base.

Examples of the base include inorganic bases such as potassium carbonate; and organic bases such as sodium acetate, potassium acetate, pyrrolidine, pyperidine, triethylamine, 1,4-diazabicyclo[2.2.2]octane, and 1,8-diazabicyclo [5.4.0]-7-undecene.

The amount of the base to be used is usually from 0.001 to 10 mol per 1 mol of the compound (j).

Examples of the acid include carboxylic acid such as formic acid, acetic acid and trifluoro acetic acid; sulfonic acid such as methanesulfonic acid, trifluoromethanesulfonic acid and p-toluenesulfonic acid; amino acid such as alanine, glycine and proline.

The amount of the acid to be used is usually from 0.001 to 10 mol per 1 mol of the compound (j).

The amount of the compound (m) is usually from 1 to 10 mol per 1 mol of the compound (j).

The reaction temperature is usually within a range from −50 to 200° C., and the reaction time is usually within a range from 1 to 24 hours.

After completion of the reaction, the compound (I-h) can be isolated, for example, by concentration; by pouring the reaction mixture into water and extracting the mixture with an organic solvent, followed by concentration. The isolated compound (I-h) can be further purified by chromatography, recrystallization or the like, if necessary.

Step (10-2)

The compound (I-i) can be usually produced by reacting the compound (I-h) with a hydride reducing agent in the presence of a solvent.

Examples of the solvent include alcohols such as methanol, ethanol and 2-propanol; ethers such as diethyl ether, tetrahydrofuran, and dimethoxyethane; acid amides such as N,N-dimethylformamide; organosulphurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; and their mixtures.

Examples of the hydride reducing agent include sodium borohydride, sodium cyanoborohydride, sodium tri(sec-butyl)borohydride, lithium borohydride, and sodium aluminum hydride.

The amount of the hydride reducing agent is usually within a range from 1 to 1.5 mol of hydride per 1 mol of the compound (I-h).

After completion of the reaction, the compound (I-i) can be isolated, for example, by pouring the reaction mixture into water and extracting the mixture with an organic solvent, followed by concentration. The isolated compound (I-i) can be further purified by chromatography, recrystallization or the like, if necessary.

Reference Production Process 1

Among compounds of the present invention, a compound (I-f) can be converted into a compound (I-e) by a reacting with an oxidizing agent as shown below:

(I-f) → (I-e)

wherein A, Q, $R^1$, $R^{1a}$, $R^2$, $R^{2a}$, $R^3$, $R^4$ and m are as defined above, and p represents 1 or 2.

The reaction is usually carried out in the presence of a solvent.

Examples of the solvent include alcohols such as methanol and ethanol; halogenated hydrocarbons such as dichloromethane and chloroform; aromatic hydrocarbons such as toluene and xylene; aliphatic carboxylic acids such as acetic acid and trifluoroacetic acid; water; and their mixtures.

Examples of the oxidizing agent include organic peroxides such as peracetic acid, trifluoroperacetic acid, and m-chloroperbenzoic acids; halogens such as chlorine and bromine; halogen-containing imides such as N-chlorosuccinimide; halides such as perchloric acid (or a salt thereof) and periodic acid (or a salt thereof); permaganates such as potassium permanganate; chromates such as potassium chromate; peroxysulfates such as potassium peroxysulfate; and hydrogen peroxide.

The amount of the oxidizing agent to be used in the reaction is usually from 1 to 10 mol per 1 mol of the compound (I-f).

The reaction temperature is usually within a range from −50 to 200° C., and the reaction time is usually within a range from 1 to 72 hours.

After completion of the reaction, the compound (I-e) can be isolated, for example, by pouring the reaction mixture into water and extracting the mixture with an organic solvent, followed by concentration. The isolated compound (I-e) can be further purified by chromatography, recrystallization or the like, if necessary.

Examples of arthropod pests on which the compound of the present invention exhibits a controlling effect include harmful insects and harmful mites, and more specifically, the following arthropods.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinus*), and white peach scale (*Pseudaulacaspis pentagona*); lace bugs (Tingidae); cimices such as *Cimex lectularius*; psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Ostrinia furnacalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes honmai*), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes moth (*Tinea translucens*), and webbing clothes moth (*Tineola bisselliella*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:

Culices (Calicidae) such as common mosquito (*Culex pipiens pallens*), *Culex tritaeniorhynchus*, and Southern house mosquito (*Culex quinquefasciatus*); *Aedes* spp. such as yellow fever mosquito (*Aedes aegypti*), and Asian tiger mosquito (*Aedes albopictus*); *Anopheles* spp. such as *Anopheles sinensis*; Chironomidae; Houseflies (Muscidae) such as housefly (*Musca domestica*), and false stable fly (*Muscina stabulans*); blow flies (Calliphoridae); flesh flies (Sarcophagidae); little house flies (Fanniidae); anthomyiid flies (Anthomyiidae) such as seedcorn maggot (*Delia platura*), and onion maggot (*Delia antiqua*); leafminer flies (Agromyzidae) such as rice leafminer (*Agromyza oryzae*), rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloroidae) such as rice stem maggot (*Chlorops oryzae*); fruit flies (Tephritidae) such as melon fly (*Dacus cucurbitae*), and Meditteranean fruit fly (*Ceratitis capitata*); drosophila flies (Drosophilidae); humpbacked flies (Phoridae) such as *Megaselia spiracularis*; Psychodidae such as *Clogmia albipunctata*; Simuliidae; Tabanidae such as horsefly (*Tabanus trigonus*); stable flies (Stomoxys), etc.;

Coleoptera:

Corn root worms (*Diabrotica* spp.) such as Western corn root worm (*Diabrotica virgifera virgifera*), and Southern corn root worm (*Diabrotica undecimpunctata howardi*); scarabs (Scarabaeidae) such as cupreous chafer (*Anomala cuprea*), soybean beetle (*Anomala rufocuprea*), and Japanese beetle (*Popillia japonica*); weevils (Curculionidae) such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); Epilachna such as twenty-eight-spotted ladybird (*Epilachna vigintioctopunctata*); bark beetles (Scolytidae) such as powder post beetle (*Lyctus brunneus*), and pine shoot beetle (*Tomicus piniperda*); false powderpost beetles (Bostrichidae); spider beetles (Ptinidae); longhorn beetles (Cerambycidae) such as white-spotted longicorn beetle (*Anoplophora malasiaca*); click beetles (*Agriotes* spp.); *Paederus fuscipes*, etc.;

Orthoptera:

Asiatic locust (*Locusta migratoria*), African mole cricket (*Gryllotalpa africana*), rice grasshopper (*Oxya yezoensis*), rice grasshopper (*Oxya japonica*), Grylloidea, etc.;

Siphonaptera:

Cat flea (*Ctenocephalides felis*), dog flea (*Ctenocephalides canis*), human flea (*Pulex irritans*), oriental rat flea (*Xenopsylla cheopis*), etc.;

Anoplura:

Human body louse (*Pediculus humanus corporis*), crab louse (*Phthirus pubis*), short-nosed cattle louse (*Haematopinus eurysternus*), sheep louse (*Damalinia ovis*), hog louse (*Haematopinus suis*), etc.;

Hymenoptera:

Ants (Formicidae) such as *Monomorium pharaonis*, *Formica fusca japonica*, black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Betylidae); sawflies (Tenthredinidae) such as Cabbage sawfly (*Athalia rosae*), and *Athalia japonica*, etc.;

Blattodea:

Cockroaches (Blattariae) such as German cockroach (*Blattella germanica*), smokybrown cockroach (*Periplaneta fuliginosa*), American cockroach (*Periplaneta americana*), *Periplaneta brunnea*, and oriental cockroach (*Blatta orientalis*); and Termites (Termitidae) such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, Japanese dampwood termite (*Hodotermopsis japonica*), *Coptotermes guangzhoensis*, *Reticulitermes* miyatakei, *Reticulitermes flavipes amamianus*, *Reticulitermes* sp., *Nasutitermes takasagoensis*, *Pericapritermes nitobei*, *Sinocapritermes mushae*, etc.;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta* citri, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus* phoenicis; Tuckerellidae; ticks (Ixodidae) such as *Haemaphysalis longicornis*, *Haemaphysalis flava*, *Dermacentor taiwanicus*, American dog tick (*Dermacentor variabilis*), *Ixodes ovatus*, *Ixodes persulcatus*, black legged tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus*, *Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.;

Chilopoda: *Thereuonema hilgendorfi*, *Scolopendra subspinipes*, etc.;

Diplopoda: garden millipede (*Oxidus gracilis*), *Nedyopus tambanus*, etc.;

Isopoda: common pill bug (*Armadillidium vulgare*), etc.

Although the arthropod pest-controlling composition of the present invention may be the compound of the present invention itself, the arthropod pest-controlling composition of the present invention is usually in the form of a formulation such as an emulsifiable concentrate, an oil solution, a shampoo formulation, a flowable formulation, a dust, a wettable powder, a granule, a paste formulation, a microcapsule formulation, a foam formulation, an aerosol formulation, a carbon dioxide gas formulation, a tablet, or a resin formulation. The formulation of the arthropod pest-controlling composition of the present invention can be usually produced by mixing the compound of the present invention with a solid carrier, a liquid carrier and/or a gaseous carrier, and if necessary, with a surfactant or other pharmaceutical additives. The arthropod pest-controlling composition of the present invention may be processed into a poison bait, a mosquito coil, an electric mosquito mat, a smoking pesticide, a fumigant or a sheet, and then be used.

The arthropod pest-controlling composition of the present invention usually contains 0.1 to 95% by weight of the compound of the present invention.

Examples of the solid carrier include finely-divided powder and granules of clay (e.g., kaolin clay, diatomaceous earth, bentonite, agalmatolite clay (Fubasami clay), or acid clay), synthetic hydrated silicon oxide, talc, ceramics, other inorganic minerals (e.g., sericite, quartz, sulfur, activated carbon, calcium carbonate, or hydrated silica), and chemical fertilizers (e.g., ammonium sulfate, ammonium phosphate, ammonium nitrate, ammonium chloride, or urea).

Examples of the liquid carrier include aromatic or aliphatic hydrocarbons (e.g., xylene, toluene, alkylnaphthalene, phenylxylylethane, kerosene, light oil, hexane, or cyclohexane), halogenated hydrocarbons (e.g., chlorobenzene, dichloromethane, dichloroethane, or trichloroethane), alcohols (e.g., methanol, ethanol, isopropyl alcohol, butanol, hexanol, or ethylene glycol), ethers (e.g., diethylether, ethylene glycol dimethyl ether, diethylene glycol monomethyl ether, diethylene glycol monoethyl ether, propylene glycol monomethyl ether, tetrahydrofuran, or dioxane), esters (e.g., ethyl acetate, or butyl acetate), ketones (e.g., acetone, methyl ethyl ketone, methyl isobutyl ketone, or cyclohexanone), nitriles (e.g., acetonitrile, or isobutyronitrile), sulfoxides (e.g., dimethyl sulfoxide), acid amides (e.g., N,N-dimethylformamide, or N,N-dimethylacetamide), vegetable oils (e.g., soybean oil, or cottonseed oil), and vegetable essential oils (e.g., orange oil, hyssop oil, or lemon oil), water.

Examples of the gaseous carrier include butane gas, chlorofluorocarbon, liquefied petroleum gas (LPG), dimethyl ether, and carbon dioxide gas.

Examples of the surfactant include alkyl sulfate salts, alkyl sulfonate salts, alkylaryl sulfonate salts, alkyl aryl ethers and their polyoxyethylated derivatives, polyethylene glycol ethers, polyhydric alcohol esters, and sugar alcohol derivatives.

Examples of other pharmaceutical additives include a binder, a dispersant, and a stabilizer. Specific examples thereof include casein, gelatin, polysaccharides (e.g., starch, gum arabic, cellulose derivatives, or alginic acid), lignin derivatives, bentonite, saccharides, synthetic water-soluble polymers (e.g., polyvinyl alcohol, polyvinylpyrrolidone, or polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids, and fatty acid esters.

Examples of a base material for a resin formulation include vinyl chloride polymers, and polyurethane. To the base material, if necessary, a plasticizer such as phthalate (e.g., dimethyl phthalate, or dioctyl phthalate), adipate, or stearic acid may be added. The resin formulation is obtained by kneading the compound of the present invention into the base material using a conventional kneading apparatus, followed by molding such as injection molding, extrusion molding, or press molding. The resulting resin formulation may be formed into the shape of a plate, a film, a tape, a net, a string or the like via a further step of molding, cutting, or the like, if necessary.

These resin formulations may be used, for example, in the form of an animal collar, an animal ear tag, a sheet formulation, a lead, or a horticultural post.

Examples of a base material of a poison bait include cereal powder, vegetable oil, sugar, and crystalline cellulose. To the base material, if necessary, an antioxidant such as dibutylhydroxytoluene or nordihydroguaiaretic acid, a preservative such as dehydroacetic acid, an agent for preventing children or pets from eating the poison bait by mistake such as hot pepper powder, a pest-attractive perfume such as cheese perfume, onion perfume or peanut oil or the like may be added.

The arthropod pest-controlling composition of the present invention can be applied, for example, to arthropod pests directly and/or habitats of arthropod pests (e.g., plant bodies, animal bodies, or soil).

When the arthropod pest-controlling composition of the present invention is used for controlling pests in agriculture and forestry, the application amount is usually 1 to 10,000 g/ha, preferably 10 to 500 g/ha of the compound of the present invention. When the arthropod pest-controlling composition of the present invention is in the form of an emulsifiable concentrate, a wettable powder, a flowable formulation or a microcapsule formulation, it is usually used after dilution with water so as to contain 1 to 1,000 ppm of the compound of the present invention. When the arthropod pest-controlling composition of the present invention is in the form of a dust or a granule, it is usually used as it is. The arthropod pest-controlling composition of the present invention may be sprayed directly to plants to be protected from arthropod pests. Soil can be treated with the arthropod pest-controlling composition of the present invention to control arthropod pests living in the soil. Seedbeds before planting or planting holes or plant feet in planting can be also treated with the arthropod pest-controlling composition of the present invention. A sheet formulation of the arthropod pest-controlling composition of the present invention may be applied by winding it around plants, disposing it in the vicinity of plants, laying it on the soil surface at the plant feet, or the like.

The arthropod pest-controlling composition of the present invention can be used in crop lands such as cultivated lands, paddy fields, lawns and orchards. The arthropod pest-controlling composition of the present invention may control harmful arthropods in a crop land without causing drug damage to crop plants cultivated in the crop land.

Examples of such crop plants include

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, *macadamia* nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The above-described crop plants include crop plants having resistance to herbicides such as HPPD inhibitors (e.g. isoxaflutole), ALS inhibitors (e.g. imazethapyr and thifensulfuron-methyl), EPSP synthesizing enzyme inhibitors, glutamine synthesizing enzyme inhibitors, acetyl CoA carboxylase inhibitors, and bromoxynil, which resistance is imparted by a classical breeding method or a genetic engineering technique.

Examples of the crop plant having herbicide resistance imparted by a classical breeding method include Clearfield (registered mark) canola resistant to an imidazolinone herbicide such as imazethapyr, and STS soybean resistant to a sulfonylurea ALS inhibitor herbicide such as thifensulfuron-methyl. Examples of the crop plant having resistance to an acetyl CoA carboxylase inhibitor such as a trione oxime herbicide or an aryloxy phenoxypropionic acid herbicide include SR corn. The crop plants having resistance to acetyl CoA carboxylase inhibitors are found in, for example, Proc. Natl. Acad. Sci. USA 1990, 87, p. 7175-7179. In addition, a mutant acetyl CoA carboxylase resistant to an acetyl CoA carboxylase inhibitor is known, for example, in Weed Science 53: p. 728-746, 2005. When a gene encoding the mutant acetyl CoA carboxylase is introduced into a crop plant by a genetic engineering technique or when a mutation related to impartation of resistance is introduced into a gene encoding acetyl CoA carboxylase of a crop plant, a crop plant having the resistance to an acetyl CoA carboxylase inhibitor can be produced. Nucleic acids for introduction of a base substitution mutation can be introduced into the cell of a crop plant by chimeraplasty (see, Gura T. 1999, Repairing the Genome's Spelling Mistakes, Science 285: 316-318) to induce a site-directed amino acid mutation in the gene targeting an acetyl CoA carboxylase inhibitor or herbicide of the crop plant, and thereby a crop plant resistant to an acetyl CoA carboxylase inhibitor or herbicide can be produced.

Examples of the crop plant having herbicide resistance imparted by a genetic engineering technique include corn cultivars having resistance to glyphosate or glufosinate. Some of such corn cultivars are sold under the trade name of RoundupReady (registered mark), LibertyLink (registered mark), and the like.

The above-described crop plants include crop plants having an ability to produce an insecticidal toxin, for example a selective toxin originated from *Bacillus*, which ability is imparted by a genetic engineering technique.

Examples of insecticidal toxins produced in such genetically engineered plants include insecticidal proteins derived from *Bacillus cereus* and *Bacillus popilliae*; insecticidal proteins such as δ-endotoxins derived from *Bacillus thuringiensis* (e.g. Cry1Ab, Cry1Ac, Cry1F, Cry1Fa2, Cry2Ab, Cry3A, Cry3Bb1 and Cry9C), VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The toxins produced in such genetically engineered plants also include hybrid toxins, partly deficient toxins and modified toxins of insecticidal proteins such as δ-endotoxin proteins (e.g., Cry1Ab, Cry1Ac, Cry1F, Cry1Fa2, Cry2Ab, Cry3A, Cry3Bb1 and Cry9C), VIP1, VIP2, VIP3, and VIP3A. The hybrid toxin is made by combining different domains of the insecticidal proteins by a genetic engineering technique. An example of the partly deficient toxin includes Cry1Ab in which a part of amino acids is deleted. An example of the modified toxin includes a toxin in which one or more of amino acids of a naturally occurring toxin are substituted.

Examples of the insecticidal toxin and the genetically engineered crop plant having the ability to produce the insecticidal toxin are described, for example, in EP-A-0 374 753, WO 93/07278, WO 95/34656, EP-A-0 427 529, EP-A-451878, or WO 03/052073.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered mark) (a corn cultivar expressing Cry1Ab toxin), YieldGard Rootworm (registered mark) (a corn cultivar expressing Cry3Bb1 toxin), YieldGard Plus (registered mark) (a corn cultivar expressing Cry1Ab and Cry3Bb1 toxins), Heculex I (registered mark) (a corn cultivar expressing Cry1Fa2 toxin and phosphinothricin N-acetyltransferase (PAT) for imparting resistance to gluphosinate), NuCOTN33B (registered mark) (a cotton cultivar expressing Cry1Ac toxin), Bollgard I (registered mark) (a cotton cultivar expressing Cry1Ac toxin), Bollgard II (registered mark) (a cotton cultivar expressing Cry1Ac and Cry2Ab toxins), VIPCOT (registered mark) (a cotton cultivar expressing VIP toxin), NewLeaf (registered mark) (a potato cultivar expressing Cry3A toxin), NatureGard Agrisure GT Advantage (registered mark) (GA21 glyphosate-resistance character), Agrisure CB Advantage (registered mark) (Bt11 corn borer (CB) character), and Protecta (registered mark).

The above-described crop plants include those having an ability to produce an anti-pathogen substance which ability is imparted by a genetic engineering technique.

Examples of the anti-pathogen substance include PR proteins (PRPs, described in EP-A-0 392 225); ion channel inhibitors such as sodium channel inhibitors, and calcium channel inhibitors (e.g. KP1, KP4, or KP6 toxins produced by viruses); stilbene synthase; bibenzyl synthase; chitinase; glucanase; and substances produced by microorganisms such as peptide antibiotics, heterocycle-containing antibiotics, and protein factors involved in plant disease-resistance (described in WO 03/000906). Such anti-pathogen substances and genetically engineered plants which produce the anti-pathogen substances are described in EP-A-0 392 225, WO 05/33818, or EP-A-0 353 191.

When the arthropod pest-controlling composition of the present invention is used for control of epidemic, the application amount is usually 0.001 to 10 mg/m$^3$ of the compound of the present invention for application to space, and 0.001 to 100 mg/m$^2$ of the compound of the present invention for application to a plane. When the arthropod pest-controlling composition of the present invention is in the form of an emulsifiable concentrate, a wettable powder or a flowable formulation, it is usually applied after dilution with water so as to contain usually 0.001 to 10,000 ppm of the compound of the present invention. When the arthropod pest-controlling composition of the present invention is in the form of an oil solution, an aerosol formulation, a smoking pesticide or a poison bait, it is usually applied as it is.

When the arthropod pest-controlling composition of the present invention is used for controlling external parasites of livestock such as a cow, a horse, a pig, a sheep, a goat and a chicken, or small animals such as a dog, a cat, a rat and a mouse, it can be applied to the animals by a known method in the veterinary field. Specifically, when systemic control is intended, the arthropod pest-controlling composition of the present invention is administered, for example, as a tablet, a mixture with feed, a suppository or an injection (e.g., intramuscularly, subcutaneously, intravenously, or intraperitoneally). When non-systemic control is intended, the arthropod pest-controlling composition of the present invention is applied to an animal by spraying, pour-on treatment or a spot-on treatment with the arthropod pest-controlling composition in the form of an oil solution or an aqueous liquid, by washing the animal with the arthropod pest-controlling composition in the form of a shampoo formulation, or by attaching a collar or a ear tag made of the arthropod pest-controlling composition in the form of a resin formulation to the animal. When the arthropod pest-controlling composition of the present invention is administered to an animal, the dose is usually in the range of 0.1 to 1,000 mg of the compound of the present invention per 1 kg body weight of the animal.

The arthropod pest-controlling composition of the present invention can be used in admixture or combination with other insecticides, nematocides, acaricides, fungicides, herbicides, plant growth regulators, synergists, fertilizers, soil conditioners, or animal feed.

Examples of the active ingredient of the insecticides include:

(1) organic phosphorous compounds:

acephate, aluminium phosphide, butathiofos, cadusafos, chlorethoxyfos, chlorfenvinphos, chlorpyrifos, chlorpyrifos-methyl, cyanophos:CYAP, diazinon, DCIP(dichlorodiisopropyl ether), dichlofenthion:ECP, dichlorvos:DDVP, dimethoate, dimethylvinphos, disulfoton, EPN, ethion, ethoprophos, etrimfos, fenthion:MPP, fenitrothion:MEP, fosthiazate, formothion, hydrogen phosphide, isofenphos, isoxathion, malathion, mesulfenfos, methidathion:DMTP, monocrotophos, naled:BRP, oxydeprofos:ESP, parathion, phosalone, phosmet:PMP, pirimiphos-methyl, pyridafenthion, quinalphos, phenthoate:PAP, profenofos, propaphos, prothiofos, pyraclorfos, salithion, sulprofos, tebupirimfos, temephos, tetrachlorvinphos, terbufos, thiometon, trichlorphon:DEP, vamidothion, phorate, cadusafos, and the like;

(2) carbamate compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb:MIPC, metolcarb, methomyl, methiocarb, NAC, oxamyl, pirimicarb, propoxur:PHC, XMC, thiodicarb, xylylcarb, aldicarb, and the like;

(3) synthetic pyrethroid compounds:

acrinathrin, allethrin, beta-cyfluthrin, bifenthrin, cyclopro-thrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl tetramethylcyclopropanecarboxylate, and the like;

(4) nereistoxin compounds:

cartap, bensultap, thiocyclam, monosultap, bisultap, and the like;

(5) neonicotinoid compounds:

imidacloprid, nitenpyram, acetamiprid, thiamethoxam, thiacloprid, dinotefuran, clothianidin, and the like;

(6) benzoylurea compounds:

chlorfluazuron, bistrifluoron, diafenthiuron, diflubenzuron, fluazuron, flucycloxuron), flufenoxuron, hexaflumuron, lufenuron, novaluron, noviflumuron, teflubenzuron, triflumuron, triazuron, and the like;

(7) phenylpyrazole compounds:

acetoprole, ethiprole, fipronil, vaniliprole, pyriprole, pyrafluprole, and the like;

(8) Bt toxin insecticides:

live spores or crystal toxins originated from *Bacillus thuringiensis* and a mixture thereof;

(9) hydrazine compounds:

chromafenozide, halofenozide, methoxyfenozide, tebufenozide, and the like;

(10) organic chlorine compounds:

aldrin, dieldrin, dienochlor, endosulfan, methoxychlor, and the like;

(11) natural insecticides:

machine oil, nicotine-sulfate;

(12) other insecticides:

avermectin-B, bromopropylate, buprofezin, chlorphenapyr, cyromazine, D-D(1,3-Dichloropropene), emamectin-benzoate, fenazaguin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, Potassium oleate, protrifenbute, spiromesifen, Sulfur, metaflumizone, spirotetramat, pyrifluquinazone, spinetoram, chlorantraniliprole, tralopyril, any compounds represented by the following formula (A):

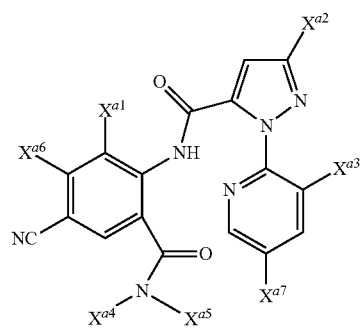

(A)

wherein $X^{a1}$ represents a methyl group, a chlorine atom, a bromine atom, or a fluorine atom, $X^{a2}$ represents a fluorine atom, a chlorine atom, a bromine atom, a C1-C4 haloalkyl group, or a C1-C4 haloalkoxy group, $X^{a3}$ represents a fluorine atom, a chlorine atom, or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkylalkyl group, or a hydrogen atom, $X^{a5}$ represents a hydrogen atom or a methyl group, $X^{a6}$ represents a hydrogen atom, a fluorine atom, or a chlorine atom, and $X^{a7}$ represents a hydrogen atom, a fluorine atom, or a chlorine atom; a compound represented by the following formula (B):

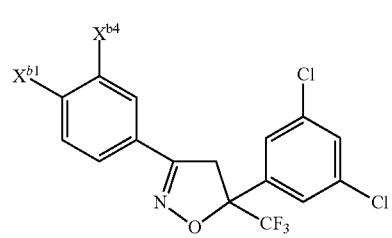

(B)

wherein $X^{b1}$ represents a $X^{b2}$—NH—C(=O) group, a $X^{b2}$—C(=O)—NH—CH$_2$ group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted C1-C4 haloalkyl group such as a 2,2,2-trifluoroethyl group, or an optionally substituted C3-C6 cycloalkyl group such as a cyclopropyl group, $X^{b3}$ represents an optionally substituted C1-C4 alkyl group such as a methyl group, and $X^{b4}$ represents a hydrogen atom, a chlorine atom, a cyano group, or a methyl group; and a compound represented by the following formula (C):

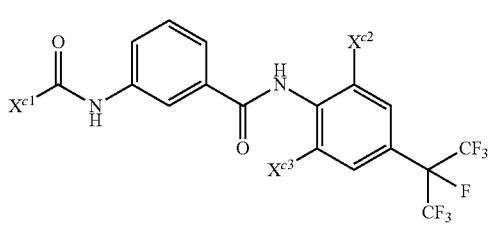

(C)

wherein $X^{c1}$ represents an optionally substituted C1-C4 alkyl group such as a 3,3,3-trifluoropropyl group, an optionsubstituted C1-C4 alkoxy group such as a 2,2,2-trichloroethoxy group, an optionally substituted phenyl group such as a 4-cyanophenyl group, or an optionally substituted pyridyl group such as a 2-chloro-3-pyridyl group, $X^{c2}$ represents a methyl group or a trifluoromethylthio group, and $X^{c3}$ represents a methyl group or a halogen atom.

Examples of the active ingredient of the acaricides include acequinocyl, amitraz, benzoximate, bifenazate, bromopropylate, chinomethionat, chlorobenzilate, CPCBS (chlorfenson), clofentezine, cyflumetofen, Kelthane (dicofol), etoxazole, fenbutatin oxide, fenothiocarb, fenpyroximate, fluacrypyrim, fluproxyfen, hexythiazox, propargite:BPPS, polynactins, pyridaben, Pyrimidifen, tebufenpyrad, tetradifon, spirodiclofen, spiromesifen, spirotetramat, amidoflumet, and cyenopyrafen.

Examples of the active ingredient of the nematocides include DCIP, fosthiazate, levamisol, methylsothiocyanate, morantel tartarate, and imicyafos.

Examples of the active ingredient of the fungicides include strobilurin compounds such as azoxystrobin; organophosphate compounds such as tolclofos-methyl; azole compounds such as triflumizole, pefurazoate and difenoconazole; fthalide, flutolanil, validamycin, probenazole, diclomezine, pencycuron, dazomet, kasugamycin, IBP, pyroquilon, oxolinic acid, tricyclazole, ferimzone, mepronil, EDDP, isoprothiolane, carpropamid, diclocymet, furametpyr, fludioxonil, procymidone and diethofencarb.

There is no limitation on the herbicides, plant growth regulators, synergists, fertilizers, soil conditioners or animal feed, and conventionally known herbicides, plant growth regulators, synergists, fertilizers, soil conditioners or animal feed can be used.

EXAMPLES

Hereinafter, the present invention is described in more detail by way of Production Examples, Formulation Examples and Test Examples. However, the present invention is not limited to these Examples.

As used herein, abbreviations have the following meanings.
Me: methyl group, Et: ethyl group, En: benzyl group, Ph: phenyl group, Ts: p-toluenesulfonyl group, and Ac: acetyl group.

First, Production Examples of the compound of the present invention are shown.

Reference Production Example 1

[Step 1-1]
To a suspension of 7.35 g of potassium thioacetate in 30 ml of N-methyl-2-pyrrolidone was added dropwise 11.39 g of bromotrifluoropropane under a nitrogen atmosphere at 0° C. over 15 minutes, followed by stirring at room temperature for 1 hour. The reaction mixture was heated to 80° C. and distilled under reduced pressure to obtain 9.99 g of 3,3,3-trifluoropropyl thioacetate represented by the following formula.

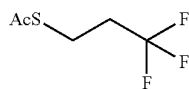

$^1$H-NMR (CDCl$_3$, TMS, δ (ppm)): 2.35-2.43 (2H, m), 2.36 (3H, s), 3.01-3.06 (2H, m)

[Step 1-2]
A solution of 9.99 g of 3,3,3-trifluoropropyl thioacetate in 60 ml of tetrahydrofuran was cooled to 0° C. To the solution was added dropwise 11.2 g of a 28% solution of sodium methoxide in methanol over 15 minutes, followed by stirring at room temperature for 1 hour. To the mixture, 4.38 g of chloroacetonitrile was added at 0° C., followed by stirring at room temperature for 3 hours. The reaction mixture was cooled in an ice bath, and a saturated aqueous sodium chloride solution was added thereto. The mixture was extracted twice with 100 ml of t-butyl methyl ether. Organic layers were combined, washed with a saturated aqueous sodium chloride solution, dried over sodium sulfate, and filtered. The solvent was distilled off under reduced pressure. The residue was subjected to silica gel column chromatography to obtain 7.56 g of (3,3,3-trifluoropropylthio)acetonitrile represented by the following formula.

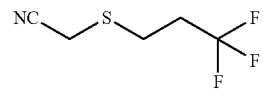

$^1$H-NMR (CDCl$_3$, TMS, δ (ppm)): 2.44-2.55 (2H, m), 2.92-2.98 (2H, m), 3.36 (2H, s)

[Step 1-3]
To a suspension of 4.97 g of (3,3,3-trifluoropropylthio)acetonitrile and 0.07 g of sodium tungstate dihydrate in 7 mL of water was added 2.3 ml of a 31% solution of hydrogen peroxide in water while the suspension was stirred. After the mixture was heated to 65° C., 2.3 ml of a 31% solution of hydrogen peroxide in water was added thereto. After the mixture was stirred at 70° C. for 1 hour and then cooled to room temperature, 5 ml of an aqueous 10% sodium sulfite solution was added and the mixture was extracted three times with 30 ml of ethyl acetate. Organic layers were combined, washed with a saturated aqueous sodium chloride solution, dried over sodium sulfate, and filtered. The solvent was distilled off under reduced pressure. The residue was crystallized from a mixture of chloroform:hexane=1:2 to obtain 5.44 g of (3,3,3-trifluoropropylsulfonyl)acetonitrile represented by the following formula.

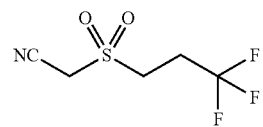 [SMILES: N#CCS(=O)(=O)CCC(F)(F)F]

$^1$H-NMR (CDCl$_3$, TMS, δ (ppm)): 2.73-2.85 (2H, m), 3.50-3.56 (2H, m), 4.07 (2H, s).

Production Example 1

Under reflux conditions, 2.01 g of (3,3,3-trifluoropropylsulfonyl)acetonitrile obtained in Reference Production Example 1, 80 ml of toluene, 0.17 g of L-proline and 1.80 g of 1-ethoxycarbonyl-4-oxopiperidine were heated and stirred for 1 hour. After 40 ml of toluene was distilled off from the reaction mixture, the reaction mixture was cooled to room temperature. To the reaction mixture, 1 ml of N,N-dimethylformamide was added. After the mixture was cooled to 0° C., 0.40 g of sodium borohydride was added. After stirring at room temperature for 1 hour, the mixture was cooled to 0° C. and 20 ml of water was added thereto. To the solution was added dropwise 15 ml of 0.5 N hydrochloric acid while the solution was stirred. Then, the solution was neutralized with sodium hydrogen carbonate. The mixture was extracted three times with 50 ml of ethyl acetate. The organic layer was washed with 20 ml of a saturated sodium hydrogen carbonate solution and 20 ml of a saturated aqueous sodium chloride solution, dried over sodium sulfate, and filtered. The solvent was distilled off under reduced pressure. The residue was subjected to silica gel column chromatography to obtain 4.40 g of 2-[N-(ethoxycarbonyl)piperidin-4-yl]-2-(3,3,3-trifluoropropylsulfonyl)acetonitrile (hereinafter referred to as the present compound (1)) represented by the following formula.

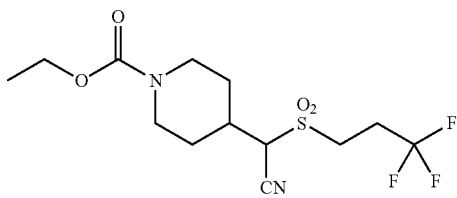

(1)

$^1$H-NMR (CDCl$_3$, TMS, δ (ppm)): 1.27 (3H, t), 1.51-1.68 (2H, m), 1.79-1.87 (1H, m), 2.10-2.19 (1H, m), 2.53-2.65 (1H, m), 2.69-2.91 (4H, m), 3.39-3.48 (1H, m), 3.52-3.61 (1H, m), 3.87 (1H, d), 4.14 (2H, q), 4.19-4.41 (2H, m)

Production Example 2

A mixture of 6.04 g of (3,3,3-trifluoropropylsulfonyl)acetonitrile, 200 ml of toluene, 0.35 g of L-proline and 5.98 g of 1-tert-butoxycarbonyl-4-oxopiperidine was heated and stirred under reflux conditions for 3 hours. After 150 ml of toluene was distilled off from the reaction mixture, the mixture was cooled to room temperature. To the reaction mixture was added 50 ml of tetrahydrofuran. The mixture was cooled to 0° C. and 0.56 g of sodium borohydride was added thereto. After the mixture was stirred at room temperature for 6 hours and then cooled to 0° C., 50 ml of water was added thereto. To the solution was added dropwise 60 ml of 1N hydrochloric acid while the solution was stirred. The mixture was neutralized with sodium hydrogen carbonate, followed by extraction three times with 50 ml of ethyl acetate. The organic layer was washed with 50 ml of a saturated sodium hydrogen carbonate solution and 50 ml of a saturated aqueous sodium chloride solution, dried over sodium sulfate, and filtered. The solvent was distilled off under reduced pressure. The residue was subjected to silica gel column chromatography to obtain 6.43 g of 2-[N-(tert-butoxycarbonyl)piperidin-4-yl]-2-(3,3,3-trifluoropropylsulfonyl)acetonitrile (hereinafter referred to as the present compound (2)) represented by the following formula.

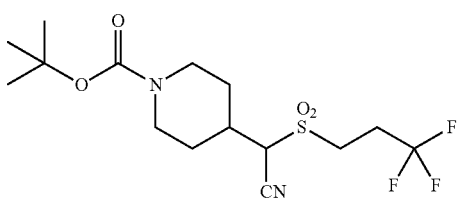

(2)

$^1$H-NMR (CDCl$_3$, TMS, δ (ppm)): 1.46 (9H, s), 1.53-1.66 (2H, m), 1.76-1.86 (1H, m), 2.09-2.17 (1H, m), 2.53-2.66 (1H, m), 2.67-2.88 (4H, m), 3.39-3.49 (1H, m), 3.50-3.61 (1H, m), 3.86 (1H, d), 4.17-4.32 (2H, m)

Production Example 3

To a solution of 6.43 g of the present compound (2) in 15 ml of chloroform were added 5 ml of trifluoroacetic acid and 0.01 g of thioanisole. The reaction mixture was stirred at room temperature for 48 hours, cooled to 0° C. and neutralized with an aqueous saturated sodium hydrogen carbonate solution. Then, the chloroform layer was separated. The aqueous layer was saturated with sodium chloride and extracted five times with 30 ml of acetonitrile. The organic layer was dried over sodium sulfate, and filtered. The solvent was distilled off under reduced pressure. The residue was crystallized from chloroform to obtain 2.96 g of 2-(1H-piperidin-4-yl)-2-(3,3,3-trifluoropropylsulfonyl)acetonitrile (hereinafter referred to as the present compound (3)) represented by the following formula.

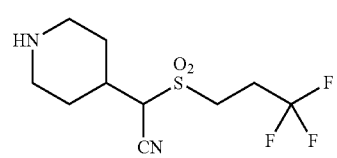

(3)

$^1$H-NMR (DMSO-d6, TMS, δ (ppm)): 1.16-1.37 (2H, m), 1.64-1.80 (1H, m), 1.85-1.99 (1H, m), 2.43-3.04 (5H, m), 3.28-3.88 (3H, m), 4.17-4.32 (2H, m), 5.21 (1H, br. s)

Production Example 4

A mixture of 2.01 g of (3,3,3-trifluoropropylsulfonyl)acetonitrile, 50 ml of tetrahydrofuran, 0.23 g of L-proline and 1.39 g of 4-oxothiane was heated and stirred under reflux conditions for 7 hours. After the reaction mixture was cooled to 0° C., 0.19 g of sodium borohydride was added thereto. After the mixture was stirred at room temperature for 1 hour and then cooled to 0° C., 50 ml of water and 50 ml of ethyl acetate were added thereto. To the solution was added dropwise 60 ml of 1 N hydrochloric acid while the solution was stirred. The mixture was extracted twice with 50 ml of ethyl acetate. The organic layer was washed with 50 ml of a saturated sodium hydrogen carbonate solution and 50 ml of a saturated aqueous sodium chloride solution, dried over sodium sulfate, and filtered. The solvent was distilled off under reduced pressure. The residue was subjected to silica gel column chromatography to obtain 2.14 g of 2-(tetrahydrothiopyran-4-yl)-2-(3,3,3-trifluoropropylsulfonyl)acetonitrile (hereinafter referred to as the present compound (4)) represented by the following formula.

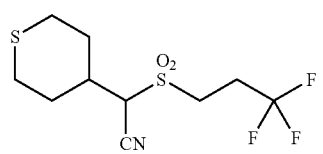

(4)

$^1$H-NMR (CDCl$_3$, TMS, δ (ppm)): 1.78-1.92 (2H, m), 2.03-2.12 (1H, m), 2.45-2.54 (2H, m), 2.65-2.85 (6H, m), 3.39-3.47 (1H, m), 3.51-3.60 (1H, m), 3.77 (1H, d)

Production Example 5

A solution of 1.82 g of 2-(tetrahydrothiopyran-4-yl)-2-(3,3,3-trifluoropropylsulfonyl)acetonitrile in 12 ml of methanol was cooled to −20° C. under a nitrogen atmosphere. To the solution was added dropwise a solution of 3.72 g of a double salt of 2KHSO$_5$.KHSO$_4$.K$_2$SO$_4$ (Oxone, registered mark) in 24 ml of water over 30 minutes, followed by stirring for 1 hour. To the mixture was added 30 ml of an aqueous 10% sodium sulfite solution, and methanol was distilled off under reduced pressure. Then, the mixture was extracted three times with 30 ml of ethyl acetate. Organic layers were combined, washed with 30 ml of an aqueous 10% sodium sulfite solution and 30 ml of a saturated aqueous sodium chloride solution, dried over sodium sulfate, filtered, and then concentrated under reduced pressure. The residue was subjected to silica gel column chromatography to obtain 1.02 g of 2-(1-oxo-1λ$^4$-tetrahydrothiopyran-4-yl)-2-(3,3,3-trifluoropropylsulfonyl)acetonitrile (hereinafter referred to as the present compound (5)) and 0.73 g of 2-(1,1-dioxo-1λ$^4$-tetrahydrothiopyran-4-yl)-2-(3,3,3-trifluoropropylsulfonyl)acetonitrile (hereinafter referred to as the present compound (6)), which are represented by the following formulae.

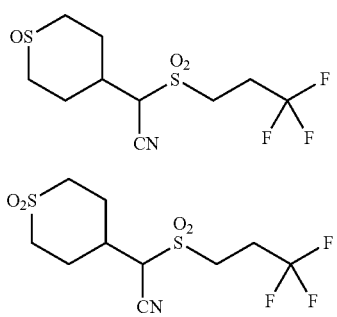

The present compound (5) was obtained as a 1:1 mixture of two stereoisomers.
Present Compound (5) (Isomer 1)
$^1$H-NMR (CDCl$_3$, TMS, δ (ppm)): 1.84-2.41 (3H, m), 2.48-2.86 (5H, m), 3.06-3.66 (5H, m), 3.98 (1H, d)
Present Compound (5) (Isomer 2)
$^1$H-NMR (CDCl$_3$, TMS, δ (ppm)): 1.84-2.41 (3H, m), 2.48-2.86 (5H, m), 3.06-3.66 (5H, m), 4.05 (1H, d)
Present Compound (6)
$^1$H-NMR (CDCl$_3$, TMS, δ (ppm)): 2.22-2.42 (3H, m), 2.58-2.89 (4H, m), 3.06-3.23 (4H, m), 3.43-3.52 (1H, m), 3.58-3.67 (1H, m), 3.94 (1H, d)

Production Example 6

A mixture of 8.05 g of (3,3,3-trifluoropropylsulfonyl)acetonitrile, 160 ml of toluene, 0.92 g of L-proline and 4.29 g of 3-oxotetrahydrothiophene was heated under reflux for 3 hours under a nitrogen atmosphere. After 40 ml of toluene was distilled off from the reaction mixture, 40 ml of toluene and 4.29 g of 3-oxotetrahydrothiophene were added thereto. The mixture was heated under reflux for 1 hour and then cooled to room temperature. After the reaction mixture was cooled to 0° C., 4 ml of N,N-dimethylformamide and 1.48 g of sodium borohydride were added thereto. The mixture was stirred at room temperature for 1 hour and then cooled to 0° C., and 50 ml of water and 50 ml of ethyl acetate were added thereto. To the solution was added dropwise 60 ml of 1N hydrochloric acid while the solution was stirred. The mixture was extracted twice with 50 ml of ethyl acetate. The organic layer was washed with 50 ml of a saturated sodium hydrogen carbonate solution and 50 ml of a saturated aqueous sodium chloride solution, dried over sodium sulfate, and filtered. The solvent was distilled off under reduced pressure. The residue was subjected to silica gel column chromatography to obtain 0.33 g of 2-(tetrahydrothiophen-3-yl)-2-(3,3,3-trifluoropropylsulfonyl)acetonitrile (hereinafter referred to as the present compound (7)) represented by the following formula.

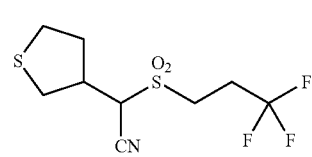

The present compound (7) was obtained as a 1:1 mixture of two stereoisomers.
Present Compound (7) (Isomer 1)
$^1$H-NMR (CDCl$_3$, TMS, δ (ppm)): 2.02-2.13 (1H, m), 2.37-2.44 (1H, m), 2.72-2.86 (2H, m), 2.89-3.25 (5H, m), 3.43-3.53 (1H, m), 3.55-3.64 (1H, m), 4.15-4.18 (1H, m)
Present Compound (7) (Isomer 2)
$^1$H-NMR (CDCl$_3$, TMS, δ (ppm)): 2.02-2.13 (1H, m), 2.47-2.55 (1H, m), 2.72-2.86 (2H, m), 2.89-3.25 (5H, m), 3.43-3.53 (1H, m), 3.55-3.64 (1H, m), 4.15-4.18 (1H, m)

Production Example 7

A solution of 0.49 g of 2-(tetrahydrothiophen-3-yl)-2-(3,3,3-trifluoropropylsulfonyl)acetonitrile in 3 ml of methanol was cooled to −20° C. under a nitrogen atmosphere.

To the solution was added dropwise a suspension of 0.53 g of double salt of 2KHSO$_5$.KHSO$_4$.K$_2$SO$_4$ (Oxone, registered mark) in 2 ml of water over 5 minutes, followed by stirring at room temperature for 1 hour. Further 0.21 g of Oxone was added thereto, followed by stirring at room temperature for 2 hours. The mixture was cooled to 0° C. and 10 ml of an aqueous 10% sodium sulfite solution was added thereto. Then, methanol was distilled off under reduced pressure, and the mixture was extracted three times with 50 ml of ethyl acetate. Organic layers were combined, washed with 20 ml of an aqueous 10% sodium sulfite solution and 20 ml of a saturated aqueous sodium chloride solution, dried over sodium sulfate, filtered, and then concentrated under reduced pressure. The residue was subjected to silica gel column chromatography to obtain 0.17 g of 2-(1-oxo-1λ$^4$-tetrahydrothiophen-3-yl)-2-(3,3,3-trifluoropropylsulfonyl)acetonitrile (hereinafter referred to as the present compound (8)) represented by the following formula.

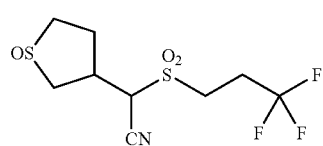

The present compound (8) was obtained as a 1:1 mixture of two stereoisomers.
Present Compound (8)
GC-MS m/z (M+): Calcd. For $C_9H_{12}F_3NO_3S_2$: 303. Found: 303.

Production Example 8

To a solution of 1.76 g of (3,3,3-trifluoropropylsulfonyl) acetonitrile in 8 ml of N,N-dimethylformamide were added 0.15 g of potassium iodide, 1.21 g of potassium carbonate and 2.12 g of tetrahydrofuran-3-yl-p-toluenesulfonate, followed by stirring at 50° C. for 6 hours. The reaction mixture was cooled to room temperature. Thereto, 50 ml of ethyl acetate and then 30 ml of an aqueous 1 N hydrochloric acid solution were sequentially added. The organic layer was separated and the aqueous layer was extracted twice with 50 ml of ethyl acetate. Organic layers were combined, washed with 30 ml of an aqueous saturated sodium hydrogen carbonate solution and then 30 ml of a saturated aqueous sodium chloride solution, dried over sodium sulfate, filtered, and then concentrated under reduced pressure. The residue was subjected to silica gel column chromatography to obtain 0.45 g of 3-(tetrahydrofuran-3-yl)-2-(3,3,3-trifluoropropylsulfonyl)propionitrile (hereinafter referred to as the present compound (9)) represented by the following formula.

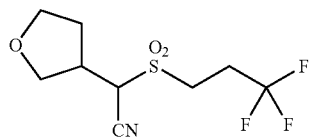
(9)

The present compound was obtained as a 1:1 mixture of two stereoisomers.
Present Compound (9) (Isomer 1)
$^1$H-NMR (CDCl$_3$, TMS, δ (ppm)): 1.93-2.12 (1H, m), 2.30-2.46 (1H, m), 2.71-2.86 (2H, m), 3.06-3.15 (1H, m), 3.43-3.51 (1H, m), 3.54-3.62 (1H, m), 3.80-3.88 (2H, m), 3.94-4.15 (3H, m).
Present Compound (9) (Isomer 2)
$^1$H-NMR (CDCl$_3$, TMS, δ (ppm)): 1.93-2.12 (1H, m), 2.30-2.46 (1H, m), 2.71-2.86 (2H, m), 3.06-3.15 (1H, m), 3.43-3.51, (1H, m), 3.54-3.62 (1H, m), 3.72-3.76 (1H, m), 3.80-3.88 (1H, m), 3.94-4.15 (3H, m).

Production Example 9

To a solution of 1.03 g of (3,3,3-trifluoropropylsulfonyl) acetonitrile in 4 ml of N,N-dimethylformamide were added 0.55 g of potassium carbonate and 1.03 g of tetrahydrofuran-2-ylmethyl-p-toluenesulfonate, followed by stirring at 50° C. for 4 hours. The reaction mixture was cooled to room temperature, and 30 ml of ethyl acetate and then 30 ml of an aqueous 1 N hydrochloric acid solution were sequentially added thereto. The organic layer was separated and the aqueous layer was extracted twice with 30 ml of ethyl acetate. Organic layers were combined, washed with 30 ml of an aqueous saturated sodium hydrogen carbonate solution and then 30 ml of a saturated aqueous sodium chloride solution, dried over sodium sulfate, filtered, and then concentrated under reduced pressure. The residue was subjected to silica gel column chromatography to obtain 0.43 g of 3-(2-tetrahydrofuran-2-yl)-2-(3,3,3-trifluoropropylsulfonyl)propionitrile (hereinafter referred to as the present compound (10)).

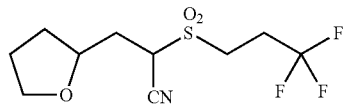
(10)

The present compound was obtained as a 1:1 mixture of two stereoisomers.
Present Compound (10)
$^1$H-NMR (CDCl$_3$, TMS, δ (ppm)): 1.52-1.65 (1H, m), 1.85-1.99 (2H, m), 1.99-2.86 (5H, m), 3.73-3.92 (5H, m), 1.14-4.25 (1H, m)

Production Example 10

To a solution of 0.81 g of (3,3,3-trifluoropropylsulfonyl) acetonitrile in 4 ml of N,N-dimethylformamide were added 0.55 g of potassium carbonate, 0.66 g of potassium iodide and 1.00 g of tetrahydrofuran-3-ylmethyl-p-toluenesulfonate, followed by stirring at 50° C. for 4 hours. The reaction mixture was cooled to room temperature, and 30 ml of ethyl acetate and then 30 ml of an aqueous 1 N hydrochloric acid solution were sequentially added thereto. The organic layer was separated and the aqueous layer was extracted twice with 30 ml of ethyl acetate. Organic layers were combined, washed with 30 ml of an aqueous saturated sodium hydrogen carbonate solution and then 30 ml of a saturated aqueous sodium chloride solution, dried over sodium sulfate, filtered, and then concentrated under reduced pressure. The residue was subjected to silica gel column chromatography to obtain 0.62 g of 3-(tetrahydrofuran-3-yl)-2-(3,3,3-trifluoropropylsulfonyl) propionitrile (hereinafter referred to as the present compound (11)) represented by the following formula.

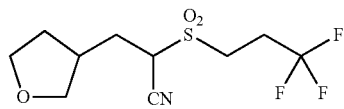
(11)

$^1$H-NMR (CDCl$_3$, TMS, δ (ppm)): 1.53-1.76 (1H, m), 2.12-2.32 (3H, m), 2.49-2.59 (1H, m), 2.73-2.84 (2H, m), 3.43-3.58 (3H, m), 3.77-3.84 (1H, m), 3.87-4.02 (3H, m)

Production Example 11

To a solution of 1.91 g of (3,3,3-trifluoropropylsulfonyl) acetonitrile in 10 ml of N,N-dimethylformamide were added 1.31 g of potassium carbonate, 1.58 g of potassium iodide and 1.28 g of 2-chloromethyltetrahydropyran, followed by stirring at 50° C. for 8 hours. The reaction mixture was cooled to room temperature, and 30 ml of ethyl acetate and then 30 ml of an aqueous 1 N hydrochloric acid solution were sequentially added thereto. The organic layer was separated and the aqueous layer was extracted twice with 30 ml of ethyl acetate. Organic layers were combined, washed with 30 ml of an aqueous saturated sodium hydrogen carbonate solution and then 30 ml of a saturated aqueous sodium chloride solution, dried over sodium sulfate, filtered, and then concentrated under reduced pressure. The residue was subjected to silica gel column chromatography to obtain 0.38 g of 3-(2-tetrahydropyran-2-yl)-2-(3,3,3-trifluoropropylsulfonyl)propionitrile (hereinafter referred to as the present compound (12)) represented by the following formula.

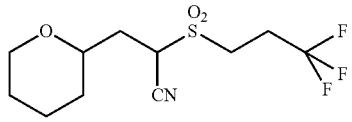

Present Compound (12)
$^1$H-NMR (CDCl$_3$, TMS, δ (ppm)): 1.30-1.41 (1H, m), 1.45-1.61 (3H, m), 1.63-1.72 (1H, m), 1.84-1.92 (1H, m), 2.09-2.29 (2H, m), 2.71-2.83 (2H, m), 3.40-3.56 (4H, m), 3.95-4.00 (1H, m), 4.35-4.00 (1H, m)

Production Example 12

To a solution of 1.01 g of (3,3,3-trifluoropropylsulfonyl)acetonitrile in 5 ml of N,N-dimethylformamide were added 0.69 g of potassium carbonate and 0.90 g of 5-bromomethyl-γ-butyrolactone, followed by stirring at 50° C. for 4 hours. The reaction mixture was cooled to room temperature, and 30 ml of ethyl acetate and then 30 ml of an aqueous 1 N hydrochloric acid solution were sequentially added thereto. The organic layer was separated and the aqueous layer was extracted twice with 30 ml of ethyl acetate. Organic layers were combined, washed with 30 ml of an aqueous saturated sodium hydrogen carbonate solution and then 30 ml of a saturated aqueous sodium chloride solution, dried over sodium sulfate, filtered, and then concentrated under reduced pressure. The residue was subjected to silica gel column chromatography to obtain 0.43 g of 3-(2-oxotetrahydrofuran-5-yl)-2-(3,3,3-trifluoropropylsulfonyl)propionitrile (hereinafter referred to as the present compound (13)) represented by the following formula.

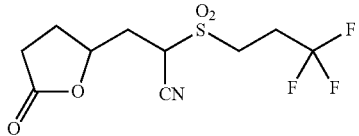

Present Compound (13)
$^1$H-NMR (CDCl$_3$, TMS, δ (ppm)): 1.99-2.10 (1H, m), 2.36-2.49 (2H, m), 2.52-2.62 (1H, m), 2.63-2.70 (2H, m), 2.73-2.85 (2H, m), 3.47-3.63 (2H, m), 4.37-4.42 (1H, m), 4.73-4.81 (1H, m)

Reference Production Example 2

[Step 2-1]
To a suspension of 22.85 g of potassium thioacetate in 200 ml of methanol was added dropwise 54.79 g of 1-iodo-3,3,4,4,4-pentafluorobutane under a nitrogen atmosphere at 0° C. over 30 minutes, followed by stirring at room temperature for 1 hour. After the mixture was cooled to 0° C., 40.52 g of a 28% solution of sodium methoxide in methanol was added dropwise over 15 minutes, followed by stirring at room temperature for 1 hour. To the mixture, 16.61 g of chloroacetonitrile was added at 0° C., followed by stirring at room temperature for 3 hours. The reaction mixture was cooled in an ice bath and an aqueous 1N hydrochloric acid solution was added thereto. Then, methanol was distilled off under reduced pressure. The mixture was extracted twice with 200 ml of t-butyl methyl ether. The combined organic layer was washed with a saturated aqueous sodium chloride solution, dried over sodium sulfate, and filtered. The solvent was distilled off under reduced pressure. The residue was subjected to silica gel column chromatography to obtain 17.81 g of (3,3,4,4,4-pentafluorobutylthio)acetonitrile represented by the following formula.

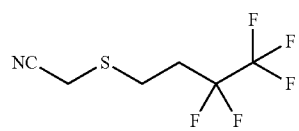 [SMILES: N#CCSCCC(F)(F)C(F)(F)F]

$^1$H-NMR (CDCl$_3$, TMS, δ (ppm)): 2.35-2.52 (2H, m), 2.94-3.03 (2H, m), 3.36 (2H, s)

[Step 2-2]
To a suspension of 17.81 g of (3,3,4,4,4-pentafluorobutylthio)acetonitrile and 0.28 g of sodium tungstate dihydrate in 30 mL of water was added 8.94 ml of a 31% solution of hydrogen peroxide in water while the suspension was stirred. The mixture was heated to 65° C., and 8.94 ml of a 31% solution of hydrogen peroxide in water was added thereto. The mixture was stirred at 70° C. for 1 hour and then cooled to room temperature. To the mixture was added 30 ml of an aqueous sodium sulfite solution, followed by extraction three times with 150 ml of ethyl acetate. Organic layers were combined, washed with a saturated aqueous sodium chloride solution, dried over sodium sulfate, and filtered. The solvent was distilled off under reduced pressure. The residue was crystallized from a 1:2 mixture of chloroform and hexane to obtain 17.84 g of (3,3,4,4,4-pentafluorobutylsulfonyl)acetonitrile represented by the following formula.

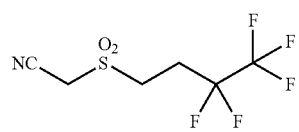

$^1$H-NMR (CDCl$_3$, TMS, δ (ppm)): 2.66-2.80 (2H, m), 3.53-3.58 (2H, m), 4.09 (2H, s)

Production Example 13

Under reflux conditions, 1.25 g of (3,3,4,4,4-pentafluorobutylsulfonyl)acetonitrile obtained in Reference Production Example 2, 50 ml of toluene, 0.11 g of DL-proline and 1.20 g of 1-tert-butoxycarbonyl-4-oxopiperidine were heated and stirred for 3 hours. After 40 ml of toluene was distilled off from the reaction mixture, the mixture was cooled to room temperature. To the reaction mixture was added 20 ml of tetrahydrofuran. The mixture was cooled to 0° C., and 0.23 g of sodium borohydride was added thereto. The mixture was stirred at room temperature for 6 hours and then cooled to 0° C., and 30 ml of water and 30 ml of ethyl acetate were added thereto. To the solution was added dropwise 30 ml of 1 N hydrochloric acid while the solution was stirred. Then, the mixture was extracted twice with 30 ml of ethyl acetate. The organic layer was washed with 30 ml of a saturated sodium hydrogen carbonate solution and 30 ml of a saturated aqueous sodium chloride solution, dried over sodium sulfate, and filtered. The solvent was distilled off under reduced pressure.

The residue was subjected to silica gel column chromatography to obtain 1.19 g of 2-[N-(tert-butoxycarbonyl)piperidin-4-yl]-2-(3,3,4,4,4-pentafluorobutylsulfonyl)acetonitrile (hereinafter referred to as the present compound (14)) represented by the following formula.

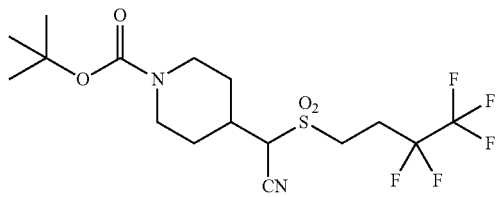

(14)

Present Compound (14)
$^1$H-NMR (CDCl$_3$, TMS, δ (ppm)): 1.46 (9H, s), 1.54-1.63 (2H, m), 1.79-1.83 (1H, m), 2.11-2.15 (1H, m), 2.55-2.64 (1H, m), 2.65-2.83 (4H, m), 3.42-3.51 (1H, m), 3.53-3.64 (1H, m), 3.87 (1H, d), 4.17-4.34 (2H, m)

Production Example 14

To a solution of 2.40 g of the present compound (14) in 10 ml of chloroform were added 5 ml of trifluoroacetic acid and 0.01 g of thioanisole. The reaction mixture was stirred at room temperature for 48 hours, cooled to 0° C. and then neutralized with an aqueous saturated sodium hydrogen carbonate solution. Then, the chloroform layer was separated. The aqueous layer was saturated with sodium chloride and extracted five times with 30 ml of acetonitrile. The organic layer was dried over sodium sulfate and filtered. The solvent was distilled off under reduced pressure. To the residue containing 2-(1H-piperidin-4-yl)-2-(3,3,3,4,4,4-pentafluorobutylsulfonyl)acetonitrile, 15 ml of tetrahydrofuran was added. The mixture was cooled to 0° C. under a nitrogen atmosphere, and 0.72 g of triethylamine and 0.66 g of methyl chloroformate were added thereto, followed by stirring at room temperature for 18 hours. To the reaction mixture were added 30 ml of ethyl acetate and 30 ml of an aqueous sodium hydrogen carbonate solution, and then, the organic layer was separated. The aqueous layer was extracted twice with 30 ml of ethyl acetate. Organic layers were combined. The combined organic layer was washed with 30 ml of a saturated sodium hydrogen carbonate solution and 30 ml of a saturated aqueous sodium chloride solution, dried over sodium sulfate, and filtered. The solvent was distilled off under reduced pressure. The residue was subjected to silica gel column chromatography to obtain 0.45 g of 2-[N-(methoxycarbonyl)piperidin-4-yl]-2-(3,3,4,4,4-pentafluorobutylsulfonyl)acetonitrile (hereinafter referred to as the present compound (15)) represented by the following formula.

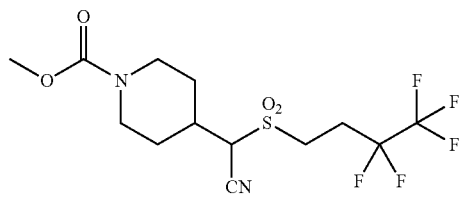

(15)

Present Compound (15)
$^1$H-NMR (CDCl$_3$, TMS, δ (ppm)): 1.53-1.65 (2H, m), 1.82-1.85 (1H, m), 2.14-2.17 (1H, m), 2.58-2.89 (5H, m), 3.43-3.51 (1H, m), 3.56-3.65 (1H, m), 3.71 (3H, s), 3.87 (1H, d), 4.17-4.38 (2H, m)

Production Example 15

Under reflux conditions, 1.40 g of (3,3,4,4,4-pentafluorobutylsulfonyl)acetonitrile, 70 ml of toluene, 0.13 g of L-proline and 0.65 g of 4-oxothiane was heated and stirred for 2 hours. After 50 ml of toluene was distilled off from the reaction mixture, the mixture was cooled to room temperature. To the reaction mixture, 2 ml of N,N-dimethylformamide was added. After the mixture was cooled to 0° C., 0.21 g of sodium borohydride was added thereto. The mixture was stirred at room temperature for 1 hour and then cooled to 0° C., and 20 ml of water and 50 ml of ethyl acetate were added thereto. To the solution was added 30 ml of 1 N hydrochloric acid while the solution was stirred. The mixture was extracted twice with 50 ml of ethyl acetate. The organic layer was washed with 30 ml of a saturated sodium hydrogen carbonate solution and 30 ml of a saturated aqueous sodium chloride solution, dried over sodium sulfate, and filtered. The solvent was distilled off under reduced pressure. The residue was subjected to silica gel column chromatography to obtain 0.42 g of 2-(tetrahydrothiopyran-4-yl)-2-(3,3,4,4,4-pentafluorobutylsulfonyl)acetonitrile (hereinafter referred to as the present compound (16)) represented by the following formula.

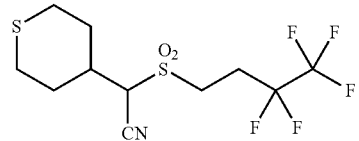

(16)

Present Compound (16)
$^1$H-NMR (CDCl$_3$, TMS, δ (ppm)): 1.79-1.93 (2H, m), 2.07-2.11 (1H, m), 2.48-2.55 (2H, m), 2.64-2.85 (6H, m), 3.41-3.49 (1H, m), 3.56-3.63 (1H, m), 3.80 (1H, d)

Reference Production Example 3

[Step 3-1]

To a solution of 24.77 g of tetrahydrofuran-2-ylmethyl-p-toluenesulfonate in 50 ml of N,N-dimethylformamide was added 20.97 g of potassium thioacetate. After the mixture was stirred under a nitrogen atmosphere at 50° C. for 6 hours and then cooled to room temperature, 100 ml of ethyl acetate and then 100 ml of an aqueous 1 N hydrochloric acid solution were sequentially added thereto. The organic layer was separated and the aqueous layer was extracted twice with 100 ml of ethyl acetate. Organic layers were combined, washed with 30 ml of an aqueous 1 N hydrochloric acid solution, 100 ml of an aqueous saturated sodium hydrogen carbonate solution and then 100 ml of a saturated aqueous sodium chloride solution, dried over sodium sulfate, filtered, and then concentrated under reduced pressure. The residue was subjected to silica gel column chromatography to obtain 24.77 g of a S-(tetrahydrofuran-2-ylmethyl)thioacetate represented by the following formula.

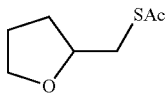

¹H-NMR (CDCl₃, TMS, δ (ppm)): 1.52-1.63 (1H, m), 1.82-1.96 (2H, m), 1.99-2.09 (1H, m), 2.35 (3H, s), 2.96-3.02 (1H, m), 3.11-3.18 (1H, m), 3.72-3.78 (1H, m), 3.85-3.92 (1H, m), 3.96-4.03 (1H, m)

[Step 3-2]

A solution of 24.77 g of S-(tetrahydrofuran-2-ylmethyl) thioacetate in 150 ml of tetrahydrofuran was cooled to 0° C. To the solution was added dropwise 29.90 g of a 28% solution of sodium methoxide in methanol over 15 minutes, followed by stirring at room temperature for 1 hour. To the mixture, 11.63 g of chloroacetonitrile was added at 0° C., followed by stirring at room temperature for 4 hours. The reaction mixture was cooled in an ice bath and 100 ml of a saturated aqueous sodium chloride solution was added thereto. The mixture was extracted twice with 100 ml of t-butyl methyl ether. The combined organic layer was washed with 100 ml of a saturated aqueous sodium chloride solution, dried over sodium sulfate, filtered, and then concentrated under reduced pressure. The residue was subjected to silica gel column chromatography to obtain 18.82 g of (tetrahydrofuran-2-ylmethylthio)acetonitrile represented by the following formula.

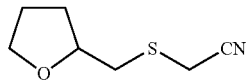

¹H-NMR (CDCl₃, TMS, δ (ppm)): 1.63-1.72 (1H, m), 1.85-2.00 (2H, m), 2.02-2.11 (1H, m), 2.84-2.87 (2H, m), 3.36-3.40 (1H, m), 3.56-3.61 (1H, m), 3.74-3.80 (1H, m), 3.89-3.95 (1H, m), 4.12-4.18 (1H, m)

[Step 3-3]

To a suspension of 67.54 g of a double salt 2KHSO₅.KHSO₄.K₂SO₄ (Oxone, registered mark) in 100 ml of water was added dropwise a solution of 15.72 g of (tetrahydrofuran-2-ylmethylthio)acetonitrile in 200 ml of methanol under a nitrogen atmosphere at 0° C. over 1 hour, followed by stirring at room temperature for 2 hours. The reaction mixture was heated to 50° C. and stirred for 4 hours. The reaction mixture was cooled in an ice bath and 300 ml of an aqueous 10% sodium sulfite solution was added thereto. Methanol was distilled off under reduced pressure. The reaction mixture was extracted three times with 200 ml of ethyl acetate. Organic layers were combined, washed with 100 ml of an aqueous 10% sodium sulfite solution and 100 ml of a saturated aqueous sodium chloride solution, dried over sodium sulfate, filtered, and then concentrated under reduced pressure. The residue was subjected to silica gel column chromatography to obtain 16.11 g of (tetrahydrofuran-2-ylmethylsulfonyl)acetonitrile represented by the following formula.

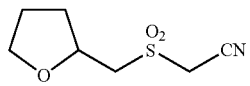

¹H-NMR (CDCl₃, TMS, δ (ppm)): 1.62-1.72 (1H, m), 1.92-2.03 (2H, m), 2.16-2.25 (1H, m), 3.15-3.22 (1H, m), 3.51-3.59 (1H, m), 3.81-4.02 (3H, m), 4.33-4.43 (1H, m), 4.48-4.52 (1H, m)

Production Example 16

To a solution of 0.30 g of (tetrahydrofuran-2-ylmethylsulfonyl)acetonitrile obtained in Reference Production Example 3 in 2 ml of N,N-dimethylformamide were added 0.22 g of potassium carbonate and 0.36 g of 3,3,3-trifluoro-1-iodopropane, followed by stirring at 50° C. for 8 hours. The reaction mixture was cooled to room temperature, and 10 ml of ethyl acetate and 10 ml of an aqueous 1 N hydrochloric acid solution were added thereto. The organic layer was separated, washed with 15 ml of an aqueous 1 N hydrochloric acid solution and then 10 ml of a saturated aqueous sodium chloride solution, dried over sodium sulfate, filtered, and then concentrated under reduced pressure. The residue was subjected to silica gel column chromatography to obtain 0.20 g of 5,5,5-trifluoro-2-(tetrahydrofuran-2-ylmethanesulfonyl) pentanenitrile (hereinafter referred to as the present compound (17)).

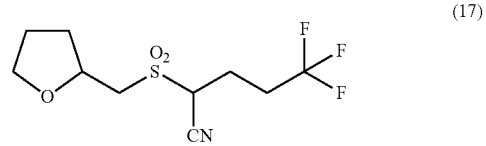 [SMILES: N#CC(CCC(F)(F)F)S(=O)(=O)CC1CCCO1]

The present compound (17) was a 3:1 mixture of two stereoisomers.

Present Compound (17) (Main Isomer)
¹H-NMR (CDCl₃, TMS, δ (ppm)): 1.62-1.71 (1H, m), 1.91-2.06 (2H, m), 2.16-2.26 (1H, m), 2.32-2.50 (4H, m), 3.18-3.22 (1H, m), 3.63-3.71 (1H, m), 3.80-3.89 (1H, m), 3.96-4.03 (1H, m) 4.31-4.42 (1H, m), 4.62-4.66 (1H, m)

Present compound (17) (Another Isomer)
¹H-NMR (CDCl₃, TMS, δ (ppm)): 1.70-1.79 (1H, m), 1.91-2.06 (2H, m), 2.16-2.26 (1H, m), 2.32-2.65 (4H, m), 3.40-3.41 (2H, m), 3.80-3.96 (2H, m), 4.31-4.42 (1H, m), 4.53-4.57 (1H, m)

Production Example 17

In the same manner as in Production Example 16 except that 0.44 g of 3,3,4,4,4-pentafluoro-1-iodobutane was used in place of 0.36 g of 3,3,3-trifluoro-1-iodopropane, 0.30 g of 5,5,6,6,6-pentafluoro-2-(tetrahydrofuran-2-ylmethanesulfonyl)hexanenitrile (hereinafter referred to as the present compound (18)) represented by the following formula:

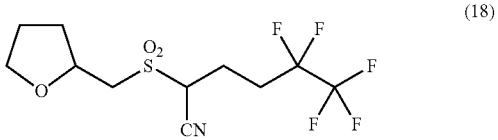 [SMILES: N#CC(CCC(F)(F)C(F)(F)F)S(=O)(=O)CC1CCCO1]

was obtained. The present compound (18) was a 5:1 mixture of two stereoisomers.

Present Compound (18) (Main Isomer)
¹H-NMR (CDCl₃, TMS, δ (ppm)): 1.62-1.71 (1H, m), 1.93-2.06 (2H, m), 2.16-2.26 (1H, m), 2.29-2.57 (4H, m), 3.18-3.23 (1H, m), 3.65-3.71 (1H, m), 3.81-3.90 (1H, m), 3.97-4.03 (1H, m) 4.33-4.43 (1H, m), 4.64-4.68 (1H, m)
Present Compound (18) (Another Isomer)
$^1$H-NMR (CDCl$_3$, TMS, δ (ppm)): 1.70-1.80 (1H, m), 1.93-2.06 (2H, m), 2.16-2.26 (1H, m), 2.29-2.57 (4H, m), 3.40-3.42 (2H, m), 3.81-3.95 (2H, m), 4.33-4.43 (1H, m), 4.53-4.57 (1H, m)

Production Example 18

In the same manner as in Production Example 16 except that 0.53 g of a 4,4,5,5,5-pentafluoropentyl-p-toluenesulfonate was used in place of 0.36 g of 3,3,3-trifluoro-1-iodopropane, 0.49 g of 6,6,7,7,7-pentafluoro-2-(tetrahydrofuran-2-ylmethanesulfonyl)heptanenitrile (hereinafter referred to as the present compound (19)) represented by the following formula:

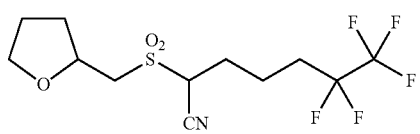

was obtained. The present compound (19) was a 4:1 mixture of two stereoisomers.
Present Compound (19) (Main Isomer)
$^1$H-NMR (CDCl$_3$, TMS, δ (ppm)): 1.62-2.29 (10H, m), 3.16-3.20 (1H, m), 3.64-3.70 (1H, m), 3.83-3.90 (1H, m), 3.97-4.03 (1H, m) 4.36-4.43 (1H, m), 4.51-4.54 (1H, m)
Present compound (19) (Another Isomer)
$^1$H-NMR (CDCl$_3$, TMS, δ (ppm)): 1.71-2.29 (10H, m), 3.39-3.41 (2H, m), 3.83-4.03 (2H, m), 4.36-4.43 (2H, m)

Reference Production Example 4

[Step 4-1]
To a solution of 28.25 g of 2-bromomethyl-1,3-dioxolane in 80 ml of N,N-dimethylformamide was added 21.25 g of potassium thioacetate. After the mixture was stirred under a nitrogen atmosphere at 50° C. for 6 hours and then cooled to room temperature, 200 ml of ethyl acetate and then 200 ml of an aqueous 1 N hydrochloric acid solution were sequentially added thereto. The organic layer was separated and the aqueous layer was extracted twice with 100 ml of ethyl acetate. Organic layers were combined, washed with 100 ml of an aqueous 1 N hydrochloric acid solution, 100 ml of an aqueous saturated sodium hydrogen carbonate solution and then 100 ml of a saturated aqueous sodium chloride solution, dried over sodium sulfate, filtered, and then concentrated under reduced pressure. The residue was subjected to silica gel column chromatography to obtain 22.69 g of a S-(1,3-dioxolan-2-ylmethyl)thioacetate represented by the following formula.

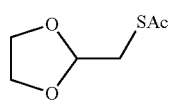

$^1$H-NMR (CDCl$_3$, TMS, δ (ppm)): 2.36 (3H, s), 3.19 (2H, d), 3.86-3.92 (2H, m), 3.96-4.03 (2H, m), 5.04 (1H, dd)

[Step 4-2]
A solution of 22.69 g of S-(1,3-dioxolan-2-ylmethyl)thioacetate in 150 ml of tetrahydrofuran was cooled to 0° C. To the solution was added dropwise 27.01 g of a 28% solution of sodium methoxide in methanol over 15 minutes, followed by stirring at room temperature for 1 hour. To the mixture, 10.49 g of chloroacetonitrile was added at 0° C., followed by stirring at room temperature for 4 hours. The reaction mixture was cooled in an ice bath and 100 ml of a saturated aqueous sodium chloride solution was added thereto. Then, the mixture was extracted twice with 100 ml of t-butyl methyl ether. The combined organic layer was washed with 100 ml of a saturated aqueous sodium chloride solution, dried over sodium sulfate, filtered, and then concentrated under reduced pressure. A solution of 14.98 g of the residue containing (1,3-dioxolan-2-ylmethylthio)acetonitrile in 200 ml of methanol was added dropwise to a suspension of 63.55 g of a double salt of 2KHSO$_5$.KHSO$_4$.K$_2$SO$_4$ (Oxone, registered mark) in 100 ml of water which was cooled to 0° C., under a nitrogen atmosphere over 1 hour. The reaction mixture was stirred at room temperature for 2 hours and heated to 50° C., followed by stirring for 4 hours. The reaction mixture was cooled in an ice bath and 300 ml of an aqueous 10% sodium sulfite solution was added thereto. Then, methanol was distilled off under reduced pressure. The reaction mixture was extracted three times with 200 ml of ethyl acetate. Organic layers were combined, washed with 100 ml of an aqueous 10% sodium sulfite solution and 100 ml of a saturated aqueous sodium chloride solution, dried over sodium sulfate, filtered, and then concentrated under reduced pressure. The residue was subjected to silica gel column chromatography to obtain 16.11 g of (1,3-dioxolan-2-ylmethanesulfonyl)acetonitrile represented by the following formula.

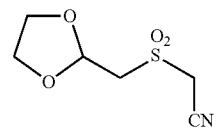 [SMILES: N#CCS(=O)(=O)CC1OCCO1]

$^1$H-NMR (CDCl$_3$, TMS, δ (ppm)): 3.54 (2H, d), 3.98-4.01 (2H, m), 4.08-4.11 (2H, m), 4.19 (2H, s), 5.37 (1H, dd)

Production Example 19

To a solution of 1.91 g of (1,3-dioxolan-2-ylmethanesulfonyl)acetonitrile obtained in Reference Production Example 4 in 10 ml of N,N-dimethylformamide were added 1.38 g of potassium carbonate and 2.74 g of 3,3,4,4,4-pentafluoro-1-iodobutane, followed by stirring at 50° C. for 6 hours. The reaction mixture was cooled to room temperature, and 50 ml of ethyl acetate and 50 ml of a saturated aqueous sodium chloride solution were added thereto. The organic layer was separated and the aqueous layer was extracted twice with 50 ml of ethyl acetate. Organic layers were combined, washed with 30 ml of an aqueous 1 N hydrochloric acid solution, 30 ml of an aqueous saturated sodium hydrogen carbonate solution, and then 30 ml of a saturated aqueous sodium chloride solution, dried over sodium sulfate, filtered, and then concentrated under reduced pressure. The residue was subjected to silica gel column chromatography to obtain 2.18 g of 5,5,5-trifluoro-2-(1,3-dioxolan-2-ylmethanesulfonyl)pentanenitrile (hereinafter referred to as the present compound (20)) represented by the following formula.

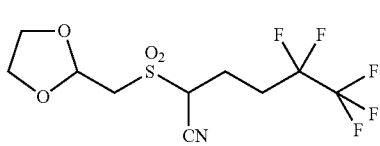

Present Compound (20)

$^1$H-NMR (CDCl$_3$, TMS, δ (ppm)): 2.31-2.59 (4H, m), 3.48-3.52 (1H, m), 3.68-3.75 (1H, m), 3.95-4.15 (4H, m), 4.51-4.55 (1H, m), 5.36-4.38 (1H, m)

Reference Production Example 5

[Step 5-1]

To a solution of 50.55 g of 2-(2-bromoethyl)-1,3-dioxolane in 100 ml of N,N-dimethylformamide was added 31.89 g of potassium thioacetate. After the mixture was stirred under a nitrogen atmosphere at 50° C. for 6 hours and then cooled to room temperature, 200 ml of ethyl acetate and then 300 ml of an aqueous 1 N hydrochloric acid solution were sequentially added thereto. The organic layer was separated and the aqueous layer was extracted once with 200 ml of ethyl acetate. Organic layers were combined, washed with 100 ml of an aqueous 1 N hydrochloric acid solution, 100 ml of an aqueous saturated sodium hydrogen carbonate solution and then 100 ml of a saturated aqueous sodium chloride solution, dried over sodium sulfate, filtered, and then concentrated under reduced pressure. The residue was subjected to silica gel column chromatography to obtain 48.64 g of a S-[2-(1,3-dioxolan-2-yl)ethyl]thioacetate represented by the following formula.

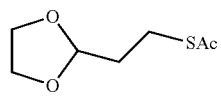

$^1$H-NMR (CDCl$_3$, TMS, δ (ppm)): 1.59 (3H, s), 2.32-2.36 (2H, m), 3.41-3.45 (2H, m), 3.90-4.11 (4H, m), 5.05 (1H, dd)

[Step 5-2]

A solution of 48.64 g of S-[2-(1,3-dioxolan-2-yl)ethyl]thioacetate in 200 ml of tetrahydrofuran was cooled to 0° C. To the solution was added dropwise 58.82 g of a 28% solution of sodium methoxide in methanol over 20 minutes, followed by stirring at room temperature for 1 hour. To the mixture, 20.48 g of chloroacetonitrile was added at 0° C., followed by stirring at room temperature for 8 hours. The reaction mixture was cooled in an ice bath and 200 ml of a saturated aqueous sodium chloride solution was added thereto. The reaction mixture was extracted twice with 200 ml of ethyl acetate. The combined organic layer was washed with 100 ml of a saturated aqueous sodium chloride solution, dried over sodium sulfate, filtered, and then concentrated under reduced pressure. The residue was subjected to silica gel column chromatography to obtain 32.58 g of [2-(1,3-dioxolan-2-yl)ethylthio]acetonitrile represented by the following formula.

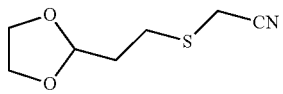 [SMILES: N#CCSCCC1OCCO1]

$^1$H-NMR (CDCl$_3$, TMS, δ (ppm)): 2.01-2.06 (2H, m), 2.84-2.88 (2H, m), 3.32 (2H, s), 3.86-3.90 (2H, m), 3.97-4.01 (2H, m), 4.99 (1H, dd)

[Step 5-3]

To a suspension of 115.63 g of a double salt of 2KHSO$_5$.KHSO$_4$.K$_2$SO$_4$ (Oxone, registered mark) 2KHSO$_5$.KHSO$_4$.K$_2$SO$_4$ (Oxone, registered mark) in 200 ml of water was added dropwise a solution of 32.58 g of [2-(1, 3-dioxolan-2-yl)ethylthio]acetonitrile in 400 ml of methanol under a nitrogen atmosphere at 0° C. over 1 hour, followed by stirring at room temperature for 2 hours. The reaction mixture was heated to 50° C. and stirred for 4 hours. The reaction mixture was cooled in an ice bath and 300 ml of an aqueous 10% sodium sulfite solution was added thereto. Then, methanol was distilled off under reduced pressure. The reaction mixture was extracted three times with 200 ml of ethyl acetate. Organic layers were combined, washed with 100 ml of an aqueous 10% sodium sulfite solution and 100 ml of a saturated aqueous sodium chloride solution, dried over sodium sulfate, filtered, and then concentrated under reduced pressure. The residue was subjected to silica gel column chromatography to obtain 24.82 g of [2-(1,3-dioxolan-2-yl) ethanesulfonyl]acetonitrile represented by the following formula.

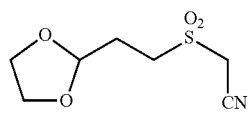 [SMILES: N#CCS(=O)(=O)CCC1OCCO1]

$^1$H-NMR (CDCl$_3$, TMS, δ (ppm)): 2.30-2.35 (2H, m), 3.41-3.44 (2H, m), 3.90-3.94 (2H, m), 4.02-4.06 (2H, m), 4.08 (2H, s), 5.06 (1H, dd)

Production Example 20

To solution of 2.05 g of [2-(1,3-dioxolan-2-yl)ethanesulfonyl]acetonitrile obtained in Reference Production Example 5 in 10 ml of N,N-dimethylformamide were added 1.38 g of potassium carbonate and 2.74 g of 3,3,4,4,4-pentafluoro-1-iodobutane, followed by stirring at 50° C. for 6 hours. The reaction mixture was cooled to room temperature, and 50 ml of ethyl acetate and 50 ml of a saturated aqueous sodium chloride solution were added thereto. The organic layer was separated and the aqueous layer was extracted twice with 50 ml of ethyl acetate. Organic layers were combined, washed with 30 ml of an aqueous 1 N hydrochloric acid solution, 30 ml of an aqueous saturated sodium hydrogen carbonate solution and then 30 ml of a saturated aqueous sodium chloride solution, dried over sodium sulfate, filtered, and then concentrated under reduced pressure. The residue was subjected to silica gel column chromatography to obtain 2.02 g of 5,5,6, 6,6,-pentafluoro-2-[2-(1,3-dioxolan-2-yl)ethanesulfonyl]- pentanenitrile (hereinafter referred to as the present compound (21)) represented by the following formula.

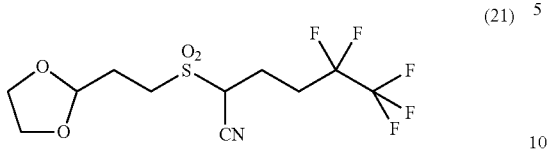

Present Compound (21)

$^1$H-NMR (CDCl$_3$, TMS, δ (ppm)): 2.29-2.56 (6H, m), 3.34-3.42 (1H, m), 3.51-3.58 (1H, m), 3.91-3.94 (2H, m), 4.03-4.06 (2H, m) 4.17-4.21 (1H, m), 5.06 (1H, dd)

Reference Production Example 6

[Step 6-1]

To a solution of 20.03 g of 2-chloromethyltetrahydropyran in 100 ml of N,N-dimethylformamide was added 17.00 g of potassium thioacetate. After the mixture was stirred under a nitrogen atmosphere at 50° C. for 10 hours and then cooled to room temperature, 100 ml of ethyl acetate and then 200 ml of an aqueous 1 N hydrochloric acid solution were sequentially added thereto. The organic layer was separated and the aqueous layer was extracted twice with 100 ml of ethyl acetate. Organic layers were combined, washed with 100 ml of an aqueous 1 N hydrochloric acid solution, 100 ml of an aqueous saturated sodium hydrogen carbonate solution and then 100 ml of a saturated aqueous sodium chloride solution, dried over sodium sulfate, filtered, and then concentrated under reduced pressure. The residue was subjected to silica gel column chromatography to obtain 9.37 g of S-(tetrahydropyran-2-ylmethyl)thioacetate represented by the following formula.

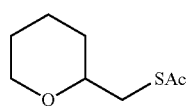

$^1$H-NMR (CDCl$_3$, TMS, δ (ppm)): 1.26-1.36 (1H, m), 1.42-1.56 (3H, m), 1.67-1.70 (1H, m), 1.81-1.86 (1H, m), 2.35 (3H, s), 2.86-2.92 (1H, m), 3.08-3.13 (1H, m), 3.34-3.45 (2H, m), 3.96-4.01 (1H, m)

[Step 6-2]

A solution of 9.37 g of S-(tetrahydropyran-2-ylmethyl) thioacetate in 50 ml of tetrahydrofuran was cooled to 0° C. To the solution was added dropwise 10.38 g of a 28% solution of sodium methoxide in methanol over 15 minutes, followed by stirring at room temperature for 1 hour. To the mixture, 4.06 g of chloroacetonitrile was added at 0° C., followed by stirring at room temperature for 8 hours. The reaction mixture was cooled in an ice bath and 100 ml of a saturated aqueous sodium chloride solution was added thereto. Then, the mixture was extracted twice with 100 ml of t-butyl methyl ether. The combined organic layer was washed with 100 ml of a saturated aqueous sodium chloride solution, dried over sodium sulfate, filtered, and then concentrated under reduced pressure. The residue was subjected to silica gel column chromatography to obtain 8.23 g of (tetrahydropyran-2-ylmethylthio)acetonitrile represented by the following formula.

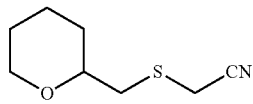 [SMILES: N#CCSCC1CCCCO1]

$^1$H-NMR (CDCl$_3$, TMS, δ (ppm)): 1.38-1.67 (5H, m), 1.85-1.87 (1H, m), 2.72-2.83 (2H, m), 3.36-3.59 (4H, m), 3.98-4.01 (1H, m)

[Step 6-3]

To a suspension of 32.53 g of a double salt of 2KHSO$_5$.KHSO$_4$.K$_2$SO$_4$ (Oxone, registered mark) in 100 ml of water was added dropwise a solution of 8.23 g of (tetrahydropyran-2-ylmethylthio)acetonitrile in 200 ml of methanol under a nitrogen atmosphere at 0° C. over 1 hour, followed by stirring at room temperature for 2 hours. The reaction mixture was heated to 50° C. and stirred for 4 hours. The reaction mixture was cooled in an ice bath and 300 ml of an aqueous 10% sodium sulfite solution was added thereto. Then, methanol was distilled off under reduced pressure. The reaction mixture was extracted three times with 200 ml of ethyl acetate. Organic layers were combined, washed with 100 ml of an aqueous 10% sodium sulfite solution and 100 ml of a saturated aqueous sodium chloride solution, dried over sodium sulfate, filtered, and then concentrated under reduced pressure. The residue was subjected to silica gel column chromatography to obtain 8.15 g of (tetrahydropyran-2-yl)-methanesulfonylacetonitrile represented by the following formula.

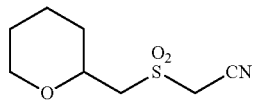 [SMILES: N#CCS(=O)(=O)CC1CCCCO1]

$^1$H-NMR (CDCl$_3$, TMS, δ (ppm)): 1.39-1.48 (1H, m), 1.53-1.66 (4H, m), 1.89-1.93 (1H, m), 3.03-3.07 (1H, m), 3.47-3.56 (2H, m), 3.91-4.04 (3H, m), 4.31-4.35 (1H, m)

Production Example 21

To a solution of 1.02 g of (tetrahydropyran-2-ylmethanesulfonyl)acetonitrile obtained in Reference Production Example 6 in 5 ml of N,N-dimethylformamide were added 0.69 g of potassium carbonate and 1.37 g of 3,3,4,4,4-pentafluoro-1-iodobutane, followed by stirring at 50° C. for 6 hours. The reaction mixture was cooled to room temperature, and 30 ml of ethyl acetate and 20 ml of an aqueous 1 N hydrochloric acid solution were added thereto. The aqueous layer was separated and extracted twice with 30 ml of ethyl acetate. Organic layers were combined, washed with 15 ml of an aqueous 1 N hydrochloric acid solution and then 10 ml of a saturated aqueous sodium chloride solution, dried over sodium sulfate, filtered, and then concentrated under reduced pressure. The residue was subjected to silica gel column chromatography to obtain 0.81 g of 5,5,6,6,6-pentafluoro-2-(tetrahydropyran-2-ylmethanesulfonyl)hexanenitrile (hereinafter referred to as the present compound (22)) represented by the formula shown below. The present compound (22) was obtained as a single isomer.

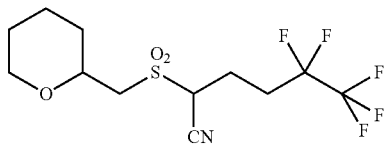

Present Compound (22)

¹H-NMR (CDCl₃, TMS, δ (ppm)): 1.40-1.47 (1H, m), 1.52-1.64 (4H, m), 1.90-1.93 (1H, m), 2.30-2.52 (4H, m), 3.03-3.07 (1H, m), 3.45-3.51 (1H, m), 3.66-3.72 (1H, m), 3.89-3.94 (1H, m), 3.97-4.01 (1H, m), 4.51-4.55 (1H, m)

Reference Production Example 7

[Step 7-1]

To a solution of 5.49 g of 7-octyn-1-yl-4-ol in 100 ml of acetone was added 8.65 g of N-bromosuccinimide under a nitrogen atmosphere at 0° C. After the mixture was stirred at room temperature for 4 hours, the solvent was distilled off under reduced pressure. Thereto 50 ml of an aqueous 5% sodium sulfite solution was added and the mixture was extracted three times with 50 ml of ethyl acetate. Organic layers were combined, washed twice with 100 ml of a saturated aqueous sodium chloride solution, dried over sodium sulfate, filtered, and then concentrated under reduced pressure. The residue was subjected to silica gel column chromatography to obtain 6.99 g of 2-bromomethyl-5-prop-2-ynyl-tetrahydrofuran.

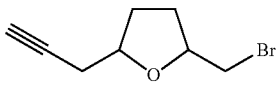

¹H-NMR (CDCl₃, TMS, δ (ppm)): 1.81-1.90 (2H, m), 1.98-2.00 (1H, m), 2.15-2.22 (2H, m), 2.41-2.47 (2H, m), 3.34-3.39 (1H, m), 3.43-4.47 (1H, m), 4.18-4.35 (2H, m)

[Step 7-2]

To a solution of 4.06 g of 2-bromomethyl-5-(prop-2-ynyl) tetrahydrofuran in 20 ml of dimethyl sulfoxide was added 2.52 g of potassium thioacetate. After the mixture was stirred under a nitrogen atmosphere at 50° C. for 6 hours and then cooled to room temperature, 50 ml of water was added thereto. The mixture was extracted three times with 50 ml of ethyl acetate. Organic layers were combined, washed twice with 50 ml of a saturated aqueous sodium chloride solution, dried over sodium sulfate, filtered, and then concentrated under reduced pressure. The residue was subjected to silica gel column chromatography to obtain 3.63 g of S-[5-(prop-2-ynyl)tetrahydrofuran-2-ylmethyl]thioacetate represented by the following formula.

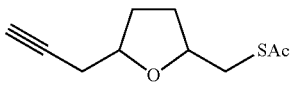

¹H-NMR (CDCl₃, TMS, δ (ppm)): 1.60-1.84 (2H, m), 1.97-1.99 (1H, m), 2.09-2.20 (2H, m), 2.33-2.49 (2H, m), 3.34 (3H, s), 3.04-3.09 (2H, m), 4.02-4.24 (2H, m)

Production Example 22

A solution of 3.52 g of S-[5-(prop-2-ynyl)tetrahydrofuran-2-ylmethyl]thioacetate obtained in Reference Production Example 7 in 40 ml of methanol was cooled to 0° C. To the solution was added 3.78 g of a 28% solution of sodium methoxide in methanol, followed by stirring at room temperature for 1 hour. To the mixture, 4.78 g of 3,3,3-trifluoro-1-iodopropane was added at 0° C., followed by stirring at room temperature for 8 hours. The reaction mixture was cooled in an ice bath and 100 ml of a saturated aqueous sodium chloride solution was added thereto. Then, methanol was distilled off under reduced pressure. The mixture was extracted three times with 50 ml of ethyl acetate. The combined organic layer was washed with 50 ml of a saturated aqueous sodium chloride solution, dried over sodium sulfate, filtered, and then concentrated under reduced pressure. The residue was subjected to silica gel column chromatography to obtain 1.68 g of 2-(prop-2-ynyl)-5-(3,3,3-trifluoropropylthiomethyl)tetrahydrofuran (hereinafter referred to as the present compound (23)) represented by the formula shown below. The present compound (23) was obtained as a single isomer.

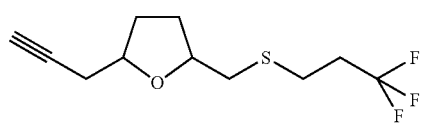

Present Compound (23)

¹H-NMR (CDCl₃, TMS, δ (ppm)): 1.68-1.85 (2H, m), 1.98-2.00 (1H, m), 2.11-2.19 (2H, m), 2.35-2.48 (4H, m), 2.62-2.83 (4H, m), 4.15-4.29 (2H, m)

Production Example 23

To a suspension of 24.60 g of a double salt of 2KHSO₅.KHSO₄.K₂SO₄ (Oxone, registered mark) in 40 ml of water was added dropwise a solution of 2.43 g of 2-(prop-2-ynyl)-5-(3,3,3-trifluoropropylthiomethyl)tetrahydrofuran in 400 ml of methanol under a nitrogen atmosphere at 0° C. over 1 hour. The reaction mixture was heated to 50° C. and then stirred for 3 hours. The reaction mixture was cooled in an ice bath and 50 ml of an aqueous 10% sodium sulfite solution was added thereto. Then, methanol was distilled off under reduced pressure. The reaction mixture was extracted three times with 50 ml of ethyl acetate. Organic layers were combined, washed with 50 ml of an aqueous 10% sodium sulfite solution and 50 ml of a saturated aqueous sodium chloride solution, dried over sodium sulfate, filtered, and then concentrated under reduced pressure. The residue was subjected to silica gel column chromatography to obtain 1.58 g of 2-(prop-2-ynyl)-5-(3,3,3-trifluoropropanesulfonylmethyl)tetrahydrofuran (hereinafter referred to as the present compound (24)) represented by the formula shown below. The present compound (24) was obtained as a single isomer.

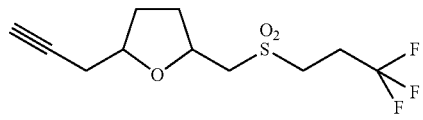

Present Compound (24)

$^1$H-NMR (CDCl$_3$, TMS, δ (ppm)): 1.66-1.86 (2H, m), 1.97-1.99 (1H, m), 2.15-2.30 (2H, m), 2.41-2.44 (2H, m), 2.62-2.76 (2H, m), 3.09-3.13 (1H, m), 3.18-3.24 (1H, m), 3.39-3.45 (2H, m), 4.18-4.25 (1H, m), 4.49-4.56 (1H, m)

Reference Production Example 8

[Step 8-1]

To a solution of 49.14 g of tetrahydrofuran-2-ylmethyl-p-toluenesulfonate in 100 ml of N,N-dimethylformamide was added 20.35 g of methyl thioglycolate and 26.50 g of potassium carbonate. After the mixture was stirred under a nitrogen atmosphere at 50° C. for 6 hours and then cooled to room temperature, 200 ml of a saturated aqueous sodium chloride solution were added thereto. The mixture was extracted twice with 200 ml of ethyl acetate. Organic layers were combined, washed twice with 200 ml of water, dried over sodium sulfate, filtered, and then concentrated under reduced pressure. The residue was subjected to silica gel column chromatography to obtain 34.33 g of a methyl 2-(tetrahydrofuran-2-ylmethylthio)acetate represented by the following formula.

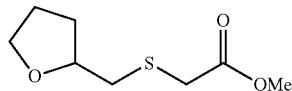 [SMILES: COC(=O)CSCC1CCCO1]

$^1$H-NMR (CDCl$_3$, TMS, δ (ppm)): 1.62-1.69 (1H, m), 1.85-1.96 (2H, m), 2.01-2.09 (1H, m), 2.78 (2H, d), 3.29-3.38 (2H, dd), 3.73-3.79 (4H, m), 3.86-3.92 (1H, m), 4.04-4.11 (1H, m)

[Step 3-2]

To a suspension of 120.00 g of a double salt 2KHSO$_5$.KHSO$_4$.K$_2$SO$_4$ (Oxone, registered mark) in 200 ml of water was added dropwise a solution of 34.33 g of methyl 2-(tetrahydrofuran-2-ylmethylthio)acetate in 200 ml of methanol under a nitrogen atmosphere at 0° C. over 1 hour, followed by stirring at room temperature for 2 hours. The reaction mixture was heated to 50° C. and stirred for 4 hours. The reaction mixture was cooled in an ice bath and 300 ml of an aqueous 10% sodium sulfite solution was added thereto. Methanol was distilled off under reduced pressure. The reaction mixture was extracted three times with 300 ml of ethyl acetate. Organic layers were combined, washed with 100 ml of an aqueous 10% sodium sulfite solution and 100 ml of a saturated aqueous sodium chloride solution, dried over sodium sulfate, filtered, and then concentrated under reduced pressure. The residue was subjected to silica gel column chromatography to obtain 32.00 g of methyl 2-(tetrahydrofuran-2-ylmethylsulfonyl)acetate represented by the following formula.

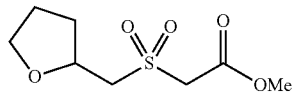 [SMILES: COC(=O)CS(=O)(=O)CC1CCCO1]

$^1$H-NMR (CDCl$_3$, TMS, δ (ppm)): 1.61-1.71 (1H, m), 1.88-2.10 (2H, m), 2.13-2.21 (1H, m), 3.07-3.12 (1H, m), 3.72-3.99 (7H, m), 4.37-4.43 (1H, m), 4.50-4.54 (1H, m)

Production Example 24

To a solution of 8.89 g of methyl 2-(tetrahydrofuran-2-ylmethylsulfonyl)acetate obtained in Reference Production Example 8 in 40 ml of N,N-dimethylformamide were added 5.55 g of potassium carbonate and 10.95 g of 3,3,4,4,4-pentafluorofluoro-1-iodobutane, followed by stirring at 50° C. for 3 hours. The reaction mixture was cooled to room temperature, and 200 ml of ethyl acetate and 150 ml of an aqueous 1 N hydrochloric acid solution were added thereto. The organic layer was separated, washed with 150 ml of an aqueous 1 N hydrochloric acid solution and then 100 ml of a saturated aqueous sodium chloride solution, dried over sodium sulfate, filtered, and then concentrated under reduced pressure. The residue was subjected to silica gel column chromatography to obtain 6.12 g of methyl 5,5,6,6,6-pentafluoro-2-(tetrahydrofuran-2-ylmethanesulfonyl)hexanoate (hereinafter referred to as the present compound (25)).

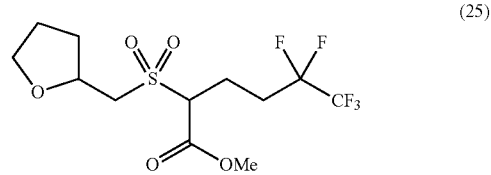 [SMILES: COC(=O)C(CCC(F)(F)C(F)(F)F)S(=O)(=O)CC1CCCO1]

The present compound (25) was a 3:1 mixture of two stereoisomers.

Present Compound (25) (Main Isomer)

$^1$H-NMR (CDCl$_3$, TMS, δ (ppm)): 1.59-1.68 (1H, m), 1.90-2.00 (2H, m), 2.13-2.52 (5H, m), 3.04-3.10 (1H, m), 3.74-3.95 (6H, m), 4.37-4.44 (1H, m), 4.53-4.57 (1H, m)

Present Compound (25) (Another Isomer)

$^1$H-NMR (CDCl$_3$, TMS, δ (ppm)): 1.70-1.78 (1H, m), 1.90-2.00 (2H, m), 2.13-2.52 (5H, m), 3.27-3.46 (2H, m), 3.74-3.95 (5H, m), 4.24-4.27 (1H, m), 4.37-4.44 (1H, m)

Production Example 25

A solution of 2.16 g of the present compound (25) in 30 ml of tetrahydrofuran was cooled to 0° C. under a nitrogen atmosphere. Thereto 0.10 g of 60% sodium hydride dispersion in paraffin liquid was added, and the mixture was stirred for 30 minutes. Then 0.86 g of N-chlorosuccinimide was added, and the mixture was stirred at room temperature overnight. To the reaction solution was added 50 ml of an aqueous 1N hydrochloric acid solution, followed by extraction with 50 ml of ethyl acetate twice. Organic layers were combined, washed with 50 ml of an aqueous saturated sodium hydrogen carbonate solution and 50 ml of an aqueous saturated sodium chloride solution. The resulting organic layer was dried over sodium sulfate, filtered, and then concentrated under reduced pressure. The residue was dissolved in 20 ml of ethanol. To the solution was added 20 ml of 28% ammonia aqueous solution and the mixture was stirred at room temperature overnight. Ethanol was distilled off under reduced pressure. To the reaction mixture was added 30 ml of an aqueous saturated sodium chloride solution, followed by extraction with 30 ml of ethyl acetate twice. Organic layers were dried over sodium sulfate, filtered, and then concentrated under reduced pressure. The residue was subjected to silica gel column chromatography, followed by crystallization with 10:1 mixture of hexane:ethyl acetate to obtain 0.50 g of 5,5,6,6,6-pentafluoro-2-(tetrahydrofuran-2-ylmethanesulfonyl)

hexanoic acid amide (hereinafter referred to as the present compound (26).

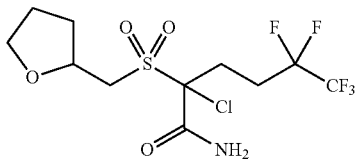
(26)

Present Compound (26)

$^1$H-NMR (CDCl$_3$, TMS, δ (ppm)): 1.68-1.82 (1H, m), 1.91-2.02 (2H, m), 2.16-2.29 (2H, m), 2.32-2.42 (1H, m), 2.49-2.58 (1H, m), 2.82-2.94 (1H, m), 3.18-3.22 (1H, m), 3.29-3.81 (2H, m), 3.81-3.86 (1H, m), 3.89-3.97 (1H, m), 4.47-4.53 (1H, m), 5.95 (1H, br.s), 6.91 (1H, br.s)

Specific examples of the compound of the present invention are shown below.

A compound represented by the formula (Iα):

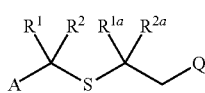
(Iα)

wherein A, $R^1$, $R^2$, $R^{1a}$, $R^{2a}$, Q, and n represent any one of combinations shown below. Combinations of A, $R^1$, $R^2$, $R^{1a}$, $R^{2a}$, Q, and n are as follows:

[A, $R^1$, $R^2$, $R^{1A}$, $R^{2A}$, Q]=

[A1, H, H, H, H, CF$_3$]; [A1, H, H, H, H, CF$_3$CH$_2$];
[A1, H, H, H, H, CF$_3$CF$_2$]; [A1, H, H, H, H, CF$_3$CH$_2$CH$_2$];
[A1, H, H, H, H, CF$_3$CF$_2$CH$_2$]; [A1, H, H, H, H, CF$_3$CF$_2$CF$_2$];
[A1, H, CN, H, H, CF$_3$]; [A1, H, CN, H, H, CF$_3$CH$_2$];
[A1, H, CN, H, H, CF$_3$CF$_2$]; [A1, H, CN, H, H, CF$_3$CH$_2$CH$_2$];
[A1, H, CN, H, H, CF$_3$CF$_2$CH$_2$]; [A1, H, CN, H, H, CF$_3$CF$_2$CF$_2$];
[A1, F, CN, H, H, CF$_3$]; [A1, F, CN, H, H, CF$_3$CH$_2$];
[A1, F, CN, H, H, CF$_3$CF$_2$]; [A1, F, CN, H, H, CF$_3$CH$_2$CH$_2$];
[A1, F, CN, H, H, CF$_3$CF$_2$CH$_2$]; [A1, F, CN, H, H, CF$_3$CF$_2$CF$_2$];
[A1, Cl, CN, H, H, CF$_3$]; [A1, Cl, CN, H, H, CF$_3$CH$_2$];
[A1, Cl, CN, H, H, CF$_3$CF$_2$]; [A1, Cl, CN, H, H, CF$_3$CH$_2$CH$_2$];
[A1, Cl, CN, H, H, CF$_3$CF$_2$CH$_2$]; [A1, Cl, CN, H, H, CF$_3$CF$_2$CF$_2$];
[A1, H, C(=O)NH$_2$, H, H, CF$_3$]; [A1, H, C(=O)NH$_2$, H, H, CF$_3$CH$_2$];
[A1, H, C(=O)NH$_2$, H, H, CF$_3$CF$_2$]; [A1, H, C(=O)NH$_2$, H, H, CF$_3$CH$_2$CH$_2$];
[A1, H, C(=O)NH$_2$, H, H, CF$_3$CF$_2$CH$_2$]; [A1, H, C(=O)NH$_2$, H, H, CF$_3$CF$_2$CF$_2$];
[A1, F, C(=O)NH$_2$, H, H, CF$_3$]; [A1, F, C(=O)NH$_2$, H, H, CF$_3$CH$_2$];
[A1, F, C(=O)NH$_2$, H, H, CF$_3$CF$_2$]; [A1, F, C(=O)NH$_2$, H, H, CF$_3$CH$_2$CH$_2$];
[A1, F, C(=O)NH$_2$, H, H, CF$_3$CF$_2$CH$_2$]; [A1, F, C(=O)NH$_2$, H, H, CF$_3$CF$_2$CF$_2$];
[A1, Cl, C(=O)NH$_2$, H, H, CF$_3$]; [A1, Cl, C(=O)NH$_2$, H, H, CF$_3$CH$_2$];
[A1, Cl, C(=O)NH$_2$, H, H, CF$_3$CF$_2$]; [A1, Cl, C(=O)NH$_2$, H, H, CF$_3$CH$_2$CH$_2$];
[A1, Cl, C(=O)NH$_2$, H, H, CF$_3$CF$_2$CH$_2$]; [A1, Cl, C(=O)NH$_2$, H, H, CF$_3$CF$_2$CF$_2$];
[A1, H, H, H, CN, CF$_3$]; [A1, H, H, H, CN, CF$_3$CH$_2$];
[A1, H, H, H, CN, CF$_3$CF$_2$]; [A1, H, H, H, CN, CF$_3$CH$_2$CH$_2$];
[A1, H, H, H, CN, CF$_3$CF$_2$CH$_2$]; [A1, H, H, H, CN, CF$_3$CF$_2$CF$_2$];
[A1, H, H, F, CN, CF$_3$]; [A1, H, H, F, CN, CF$_3$CH$_2$];
[A1, H, H, F, CN, CF$_3$CF$_2$]; [A1, H, H, F, CN, CF$_3$CH$_2$CH$_2$];
[A1, H, H, F, CN, CF$_3$CF$_2$CH$_2$]; [A1, H, H, F, CN, CF$_3$CF$_2$CF$_2$];
[A1, H, H, Cl, CN, CF$_3$]; [A1, H, H, Cl, CN, CF$_3$CH$_2$];
[A1, H, H, Cl, CN, CF$_3$CF$_2$]; [A1, H, H, Cl, CN, CF$_3$CH$_2$CH$_2$];
[A1, H, H, Cl, CN, CF$_3$CF$_2$CH$_2$]; [A1, H, H, Cl, CN, CF$_3$CF$_2$CF$_2$];
[A1, H, H, H, C(=O)NH$_2$, CF$_3$]; [A1, H, H, H, C(=O)NH$_2$, CF$_3$CH$_2$];
[A1, H, H, H, C(=O)NH$_2$, CF$_3$CF$_2$]; [A1, H, H, H, C(=O)NH$_2$, CF$_3$CH$_2$CH$_2$];
[A1, H, H, H, C(=O)NH$_2$, CF$_3$CF$_2$CH$_2$]; [A1, H, H, H, C(=O)NH$_2$, CF$_3$CF$_2$CF$_2$];
[A1, H, H, F, C(=O)NH$_2$, CF$_3$]; [A1, H, H, F, C(=O)NH$_2$, CF$_3$CH$_2$];
[A1, H, H, F, C(=O)NH$_2$, CF$_3$CF$_2$]; [A1, H, H, F, C(=O)NH$_2$, CF$_3$CH$_2$CH$_2$];
[A1, H, H, F, C(=O)NH$_2$, CF$_3$CF$_2$CH$_2$]; [A1, H, H, F, C(=O)NH$_2$, CF$_3$CF$_2$CF$_2$];
[A1, H, H, Cl, C(=O)NH$_2$, CF$_3$]; [A1, H, H, Cl, C(=O)NH$_2$, CF$_3$CH$_2$];
[A1, H, H, Cl, C(=O)NH$_2$, CF$_3$CF$_2$]; [A1, H, H, Cl, C(=O)NH$_2$, CF$_3$CH$_2$CH$_2$];
[A1, H, H, Cl, C(=O)NH$_2$, CF$_3$CF$_2$CH$_2$]; [A1, H, H, Cl, C(=O)NH$_2$, CF$_3$CF$_2$CF$_2$];
[A1, H, C(=O)OCH$_3$, H, H, CF$_3$]; [A1, H, C(=O)OCH$_3$, H, H, CF$_3$CH$_2$];
[A1, H, C(=O)OCH$_3$, H, H, CF$_3$CF$_2$]; [A1, H, C(=O)OCH$_3$, H, H, CF$_3$CH$_2$CH$_2$];
[A1, F, C(=O)OCH$_3$, H, H, CF$_3$]; [A1, F, C(=O)OCH$_3$, H, H, CF$_3$CH$_2$];
[A1, F, C(=O)OCH$_3$, H, H, CF$_3$CF$_2$]; [A1, F, C(=O)OCH$_3$, H, H, CF$_3$CH$_2$CH$_2$];
[A1, Cl, C(=O)OCH$_3$, H, H, CF$_3$]; [A1, Cl, C(=O)OCH$_3$, H, H, CF$_3$CH$_2$];
[A1, Cl, C(=O)OCH$_3$, H, H, CF$_3$CF$_2$]; [A1, Cl, C(=O)OCH$_3$, H, H, CF$_3$CH$_2$CH$_2$];
[A1, H, H, H, C(=O)OCH$_3$, CF$_3$]; [A1, H, H, H, C(=O)OCH$_3$, CF$_3$CH$_2$];
[A1, H, H, H, C(=O)OCH$_3$CF$_3$CF$_2$]; [A1, H, H, H, C(=O)OCH$_3$, CF$_3$CH$_2$CH$_2$];
[A1, H, H, F, C(=O)OCH$_3$CF$_3$]; [A1, H, H, F, C(=O)OCH$_3$CF$_3$CH$_2$];
[A1, H, H, F, C(=O)OCH$_3$, CF$_3$CF$_2$]; [A1, H, H, F, C(=O)OCH$_3$ CF$_3$CH$_2$CH$_2$];
[A1, H, H, Cl, C(=O)OCH$_3$, CF$_3$]; [A1, H, H, Cl, C(=O)OCH$_3$, CF$_3$CH$_2$];
[A1, H, H, Cl, C(=O)OCH$_3$, CF$_3$CF$_2$]; [A1, H, H, Cl, C(=O)OCH$_3$, CF$_3$CH$_2$CH$_2$];
[A2, H, H, H, H, CF$_3$]; [A2, H, H, H, H, CF$_3$CH$_2$]; [A2, H, H, H, H, CF$_3$CF$_2$]; [A2, H, H, H, H, CF$_3$CH$_2$CH$_2$];
[A2, H, H, H, H, CF$_3$CF$_2$CH$_2$]; [A2, H, H, H, H, CF$_3$CF$_2$CF$_2$];
[A2, H, CN, H, H, CF$_3$]; [A2, H, CN, H, H, CF$_3$CH$_2$];
[A2, H, CN, H, H, CF$_3$CF$_2$]; [A2, H, CN, H, H, CF$_3$CH$_2$CH$_2$];
[A2, H, CN, H, H, CF$_3$CF$_2$CH$_2$]; [A2, H, CN, H, H, CF$_3$CF$_2$CF$_2$];
[A2, F, CN, H, H, CF$_3$]; [A2, F, CN, H, H, CF$_3$CH$_2$];
[A2, F, CN, H, H, CF$_3$CF$_2$]; [A2, F, CN, H, H, CF$_3$CH$_2$CH$_2$];

[A2, F, CN, H, H, CF₃CF₂CH₂]; [A2, F, CN, H, H, CF₃CF₂CF₂];
[A2, Cl, CN, H, H, CF₃]; [A2, Cl, CN, H, H, CF₃CH₂];
[A2, Cl, CN, H, H, CF₃CF₂]; [A2, Cl, CN, H, H, CF₃CH₂CH₂];
[A2, Cl, CN, H, H, CF₃CF₂CH₂]; [A2, Cl, CN, H, H, CF₃CF₂CF₂];
[A2, H, C(=O)NH₂, H, H, CF₃]; [A2, H, C(=O)NH₂, H, H, CF₃CH₂];
[A2, H, C(=O)NH₂, H, H, CF₃CF₂]; [A2, H, C(=O)NH₂, H, H, CF₃CH₂CH₂];
[A2, H, C(=O)NH₂, H, H, CF₃CF₂CH₂]; [A2, H, C(=O)NH₂, H, H, CF₃CF₂CF₂];
[A2, F, C(=O)NH₂, H, H, CF₃]; [A2, F, C(=O)NH₂, H, H, CF₃CH₂];
[A2, F, C(=O)NH₂, H, H, CF₃CF₂]; [A2, F, C(=O)NH₂, H, H, CF₃CH₂CH₂];
[A2, F, C(=O)NH₂, H, H, CF₃CF₂CH₂]; [A2, F, C(=O)NH₂, H, H, CF₃CF₂CF₂];
[A2, Cl, C(=O)NH₂, H, H, CF₃]; [A2, Cl, C(=O)NH₂, H, H, CF₃CH₂];
[A2, Cl, C(=O)NH₂, H, H, CF₃CF₂]; [A2, Cl, C(=O)NH₂, H, H, CF₃CH₂CH₂];
[A2, Cl, C(=O)NH₂, H, H, CF₃CF₂CH₂]; [A2, Cl, C(=O)NH₂, H, H, CF₃CF₂CF₂];
[A2, H, H, H, CN, CF₃]; [A2, H, H, H, CN, CF₃CH₂];
[A2, H, H, H, CN, CF₃CF₂]; [A2, H, H, CN, CF₃CH₂CH₂];
[A2, H, H, H, CN, CF₃CF₂CH₂]; [A2, H, H, H, CN, CF₃CF₂CF₂];
[A2, H, H, F, CN, CF₃]; [A2, H, H, F, CN, CF₃CH₂];
[A2, H, H, F, CN, CF₃CF₂]; [A2, H, H, F, CN, CF₃CH₂CH₂];
[A2, H, H, F, CN, CF₃CF₂CH₂]; [A2, H, H, F, CN, CF₃CF₂CF₂];
[A2, H, H, Cl, CN, CF₃]; [A2, H, H, Cl, CN, CF₃CH₂];
[A2, H, H, Cl, CN, CF₃CF₂]; [A2, H, H, Cl, CN, CF₃CH₂CH₂];
[A2, H, H, Cl, CN, CF₃CF₂CH₂]; [A2, H, H, Cl, CN, CF₃CF₂CF₂];
[A2, H, H, H, C(=O)NH₂, CF₃]; [A2, H, H, H, C(=O)NH₂ CF₃CH₂];
[A2, H, H, H, C(=O)NH₂, CF₃CF₂]; [A2, H, H, H, C(=O)NH₂ CF₃CH₂CH₂];
[A2, H, H, H, C(=O)NH₂, CF₃CF₂CH₂]; [A2, H, H, H, C(=O)NH₂, CF₃CF₂CF₂];
[A2, H, H, F, C(=O)NH₂, CF₃]; [A2, H, H, F, C(=O)NH₂, CF₃CH₂];
[A2, H, H, F, C(=O)NH₂, CF₃CF₂]; [A2, H, H, F, C(=O)NH₂, CF₃CH₂CH₂];
[A2, H, H, F, C(=O)NH₂, CF₃CF₂CH₂]; [A2, H, H, F, C(=O)NH₂CF₃CF₂CF₂];
[A2, H, H, Cl, C(=O)NH₂, CF₃]; [A2, H, H, Cl, C(=O)NH₂, CF₃CH₂];
[A2, H, H, Cl, C(=O)NH₂, CF₃CF₂]; [A2, H, H, Cl, C(=O)NH₂, CF₃CH₂CH₂];
[A2, H, H, Cl, C(=O)NH₂, CF₃CF₂CH₂]; [A2, H, H, Cl, C(=O)NH₂, CF₃CF₂CF₂];
[A2, H, H, H, H, CF₃]; [A2, H, H, H, H, CF₃CH₂];
[A2, H, H, H, H, CF₃CF₂]; [A2, H, H, H, H, CF₃CH₂CH₂];
[A2, H, H, H, H, CF₃CF₂CH₂]; [A2, H, H, H, H, CF₃CF₂CF₂];
[A2, H, CN, H, H, CF₃]; [A2, H, CN, H, H, CF₃CH₂];
[A2, H, CN, H, H, CF₃CF₂]; [A2, H, CN, H, H, CF₃CH₂CH₂];
[A2, H, CN, H, H, CF₃CF₂CH₂]; [A2, H, CN, H, H, CF₃CF₂CF₂];
[A2, F, CN, H, H, CF₃]; [A2, F, CN, H, H, CF₃CH₂];
[A2, F, CN, H, H, CF₃CF₂]; [A2, F, CN, H, H, CF₃CH₂CH₂];
[A2, F, CN, H, H, CF₃CF₂CH₂]; [A2, F, CN, H, H, CF₃CF₂CF₂];
[A2, Cl, CN, H, CF₃]; [A2, Cl, CN, H, H, CF₃CH₂];
[A2, Cl, CN, H, H, CF₃CF₂]; [A2, Cl, CN, H, H, CF₃CH₂CH₂];
[A2, Cl, CN, H, H, CF₃CF₂CH₂]; [A2, Cl, CN, H, H, CF₃CF₂CF₂];
[A2, H, C(=O)NH₂, H, H, CF₃]; [A2, H, C(=O)NH₂, H, H, CF₃CH₂];
[A2, H, C(=O)NH₂, H, H, CF₃CF₂]; [A2, H, C(=O)NH₂, H, H, CF₃CH₂CH₂];
[A2, H, C(=O)NH₂, H, H, CF₃CF₂CH₂]; [A2, H, C(=O)NH₂, H, H, CF₃CF₂CF₂];
[A2, F, C(=O)NH₂, H, H, CF₃]; [A2, F, C(=O)NH₂, H, H, CF₃CH₂];
[A2, F, C(=O)NH₂, H, H, CF₃CF₂]; [A2, F, C(=O)NH₂, H, H, CF₃CH₂CH₂];
[A2, F, C(=O)NH₂, H, H, CF₃CF₂CH₂]; [A2, F, C(=O)NH₂, H, H, CF₃CF₂CF₂];
[A2, Cl, C(=O)NH₂, H, H, CF₃]; [A2, Cl, C(=O)NH₂, H, H, CF₃CH₂];
[A2, Cl, C(=O)NH₂, H, H, CF₃CF₂]; [A2, Cl, C(=O)NH₂, H, H, CF₃CH₂CH₂];
[A2, Cl, C(=O)NH₂, H, H, CF₃CF₂CH₂]; [A2, Cl, C(=O)NH₂, H, H, CF₃CF₂CF₂];
[A2, H, H, H, CN, CF₃]; [A2, H, H, H, CN, CF₃CH₂];
[A2, H, H, H, CN, CF₃CF₂]; [A2, H, H, H, CN, CF₃CH₂CH₂];
[A2, H, H, H, CN, CF₃CF₂CH₂]; [A2, H, H, H, CN, CF₃CF₂CF₂];
[A2, H, H, F, CN, CF₃]; [A2, H, H, F, CN, CF₃CH₂];
[A2, H, H, F, CN, CF₃CF₂]; [A2, H, H, F, CN, CF₃CH₂CH₂];
[A2, H, H, F, CN, CF₃CF₂CH₂]; [A2, H, H, F, CN, CF₃CF₂CF₂];
[A2, H, H, Cl, CN, CF₃]; [A2, H, H, Cl, CN, CF₃CH₂];
[A2, H, H, Cl, CN, CF₃CF₂]; [A2, H, H, Cl, CN, CF₃CH₂CH₂];
[A2, H, H, Cl, CN, CF₃CF₂CH₂]; [A2, H, H, Cl, CN, CF₃CF₂CF₂];
[A2, H, H, H, C(=O)NH₂, CF₃]; [A2, H, H, H, C(=O)NH₂, CF₃CH₂];
[A2, H, H, H, C(=O)NH₂, CF₃CF₂]; [A2, H, H, H, C(=O)NH₂, CF₃CH₂CH₂];
[A2, H, H, H, C(=O)NH₂, CF₃CF₂CH₂]; [A2, H, H, H, O(=O)NH₂, CF₃CF₂CF₂];
[A2, H, H, F, C(=O)NH₂, CF₃]; [A2, H, H, F, C(=O)NH₂, CF₃CH₂];
[A2, H, H, F, C(=O)NH₂, CF₃CF₂]; [A2, H, H, F, C(=O)NH₂, CF₃CH₂CH₂];
[A2, H, H, F, C(=O)NH₂, CF₃CF₂CH₂]; [A2, H, H, F, O(=O)NH₂, CF₃CF₂CF₂];
[A2, H, H, Cl, C(=O)NH₂, CF₃]; [A2, H, H, Cl, C(=O)NH₂, CF₃CH₂];
[A2, H, H, Cl, C(=O)NH₂, CF₃CF₂]; [A2, H, H, Cl, C(=O)NH₂, CF₃CH₂CH₂];
[A2, H, H, Cl, C(=O)NH₂, CF₃CF₂CH₂]; [A2, H, H, Cl, C(=O)NH₂, CF₃CF₂CF₂];
[A3, H, H, H, H, CF₃]; [A3, H, H, H, H, CF₃CH₂];
[A3, H, H, H, H, CF₃CF₂]; [A3, H, H, H, H, CF₃CH₂CH₂];
[A3, H, H, H, H, CF₃CF₂CH₂]; [A3, H, H, H, H, CF₃CF₂CF₂];
[A3, H, CN, H, H, CF₃]; [A3, H, CN, H, H, CF₃CH₂];
[A3, H, CN, H, H, CF₃CF₂]; [A3, H, CN, H, H, CF₃CH₂CH₂];
[A3, H, CN, H, H, CF₃CF₂CH₂]; [A3, H, CN, H, H, CF₃CF₂CF₂];
[A3, F, CN, H, H, CF₃]; [A3, F, CN, H, H, CF₃CH₂];
[A3, F, CN, H, H, CF₃CF₂]; [A3, F, CN, H, H, CF₃CH₂CH₂];

[A3, F, CN, H, H, CF$_3$CF$_2$CH$_2$]; [A3, F, CN, H, H, CF$_3$CF$_2$CF$_2$];
[A3, Cl, CN, H, H, CF$_3$]; [A3, Cl, CN, H, H, CF$_3$CH$_2$];
[A3, Cl, CN, H, H, CF$_3$CF$_2$]; [A3, Cl, CN, H, H, CF$_3$CH$_2$CH$_2$];
[A3, Cl, CN, H, H, CF$_3$CF$_2$CH$_2$]; [A3, Cl, CN, H, H, CF$_3$CF$_2$CF$_2$];
[A3, H, C(=O)NH$_2$, H, H, CF$_3$]; [A3, H, C(=O)NH$_2$, H, H, CF$_3$CH$_2$];
[A3, H, C(=O)NH$_2$, H, H, CF$_3$CF$_2$]; [A3, H, C(=O)NH$_2$, H, H, CF$_3$CH$_2$CH$_2$];
[A3, H, C(=O)NH$_2$, H, H, CF$_3$CF$_2$CH$_2$]; [A3, H, C(=O)NH$_2$, H, H, CF$_3$CF$_2$CF$_2$];
[A3, F, C(=O)NH$_2$, H, H, CF$_3$]; [A3, F, C(=O)NH$_2$, H, H, CF$_3$CH$_2$];
[A3, F, C(=O)NH$_2$, H, H, CF$_3$CF$_2$]; [A3, F, C(=O)NH$_2$, H, H, CF$_3$CH$_2$CH$_2$];
[A3, F, C(=O)NH$_2$, H, H, CF$_3$CF$_2$CH$_2$]; [A3, F, C(=O)NH$_2$, H, H, CF$_3$CF$_2$CF$_2$];
[A3, Cl, C(=O)NH$_2$, H, H, CF$_3$]; [A3, Cl, C(=O)NH$_2$, H, H, CF$_3$CH$_2$];
[A3, Cl, C(=O)NH$_2$, H, H, CF$_3$CF$_2$]; [A3, Cl, C(=O)NH$_2$, H, H, CF$_3$CH$_2$CH$_2$];
[A3, Cl, C(=O)NH$_2$, H, H, CF$_3$CF$_2$CH$_2$]; [A3, Cl, C(=O)NH$_2$, H, H, CF$_3$CF$_2$CF$_2$];
[A3, H, H, H, CN, CF$_3$]; [A3, H, H, H, CN, CF$_3$CH$_2$];
[A3, H, H, H, CN, CF$_3$CF$_2$]; [A3, H, H, H, CN, CF$_3$CH$_2$CH$_2$];
[A3, H, H, H, CN, CF$_3$CF$_2$CH$_2$]; [A3, H, H, H, CN, CF$_3$CF$_2$CF$_2$];
[A3, H, H, F, CN, CF$_3$]; [A3, H, H, F, CN, CF$_3$CH$_2$];
[A3, H, H, F, CN, CF$_3$CF$_2$]; [A3, H, H, F, CN, CF$_3$CH$_2$CH$_2$];
[A3, H, H, F, CN, CF$_3$CF$_2$CH$_2$]; [A3, H, H, F, CN, CF$_3$CF$_2$CF$_2$];
[A3, H, H, Cl, CN, CF$_3$]; [A3, H, H, Cl, CN, CF$_3$CH$_2$];
[A3, H, H, Cl, CN, CF$_3$CF$_2$]; [A3, H, H, Cl, CN, CF$_3$CH$_2$CH$_2$];
[A3, H, H, Cl, CN, CF$_3$CF$_2$CH$_2$]; [A3, H, H, Cl, CN, CF$_3$CF$_2$CF$_2$];
[A3, H, H, H, C(=O)NH$_2$, CF$_3$]; [A3, H, H, H, C(=O)NH$_2$, CF$_3$CH$_2$];
[A3, H, H, H, C(=O)NH$_2$, CF$_3$CF$_2$]; [A3, H, H, H, C(=O)NH$_2$, CF$_3$CH$_2$CH$_2$];
[A3, H, H, H, C(=O)NH$_2$, CF$_3$CF$_2$CH$_2$]; [A3, H, H, H, C(=O)NH$_2$, CF$_3$CF$_2$CF$_2$];
[A3, H, H, F, C(=O)NH$_2$, CF$_3$]; [A3, H, H, F, C(=O)NH$_2$, CF$_3$CH$_2$];
[A3, H, H, F, C(=O)NH$_2$, CF$_3$CF$_2$]; [A3, H, H, F, C(=O)NH$_2$, CF$_3$CH$_2$CH$_2$];
[A3, H, H, F, C(=O)NH$_2$, CF$_3$CF$_2$CH$_2$]; [A3, H, H, F, C(=O)NH$_2$, CF$_3$CF$_2$CF$_2$];
[A3, H, H, Cl, C(=O)NH$_2$, CF$_3$]; [A3, H, H, Cl, C(=O)NH$_2$, CF$_3$CH$_2$];
[A3, H, H, Cl, C(=O)NH$_2$, CF$_3$CF$_2$]; [A3, H, H, Cl, C(=O)NH$_2$, CF$_3$CH$_2$CH$_2$];
[A3, H, H, Cl, C(=O)NH$_2$, CF$_3$CF$_2$CH$_2$]; [A3, H, H, Cl, C(=O)NH$_2$, CF$_3$CF$_2$CF$_2$];
[A3, H, C(=O)OCH$_3$, H, H, CF$_3$]; [A3, H, C(=O)OCH$_3$, H, H, CF$_3$CH$_2$];
[A3, H, C(=O)OCH$_3$, H, H, CF$_3$CF$_2$]; [A3, H, C(=O)OCH$_3$, H, H, CF$_3$CH$_2$CH$_2$];
[A3, F, C(=O)OCH$_3$, H, H, CF$_3$]; [A3, F, C(=O)OCH$_3$, H, H, CF$_3$CH$_2$];
[A3, F, C(=O)OCH$_3$, H, H, CF$_3$CF$_2$]; [A3, F, C(=O)OCH$_3$, H, H, CF$_3$CH$_2$CH$_2$];
[A3, Cl, C(=O)OCH$_3$, H, H, CF$_3$]; [A3, Cl, C(=O)OCH$_3$, H, H, CF$_3$CH$_2$];
[A3, Cl, C(=O)OCH$_3$, H, H, CF$_3$CF$_2$]; [A3, Cl, C(=O)OCH$_3$, H, H, CF$_3$CH$_2$CH$_2$];
[A3, H, H, H, C(=O)OCH$_3$CF$_3$]; [A3, H, H, H, C(=O)OCH$_3$, CF$_3$CH$_2$];
[A3, H, H, H, C(=O)OCH$_3$CF$_3$CF$_2$]; [A3, H, H, H, C(=O)OCH$_3$, CF$_3$CH$_2$CH$_2$];
[A3, H, H, F, C(=O)OCH$_3$CF$_3$]; [A3, H, H, F, C(=O)OCH$_3$, CF$_3$CH$_2$];
[A3, H, H, F, C(=O)OCH$_3$, CF$_3$CF$_2$]; [A3, H, H, F, C(=O)OCH$_3$, CF$_3$CH$_2$CH$_2$];
[A3, H, H, Cl, C(=O)OCH$_3$, CF$_3$]; [A3, H, H, Cl, C(=O)OCH$_3$, CF$_3$CH$_2$];
[A3, H, H, Cl, C(=O)OCH$_3$, CF$_3$CF$_2$]; [A3, H, H, Cl, C(=O)OCH$_3$, CF$_3$CH$_2$CH$_2$];
[A4, H, H, H, H, CF$_3$]; [A4, H, H, H, H, CF$_3$CH$_2$];
[A4, H, H, H, H, CF$_3$CF$_2$]; [A4, H, H, H, H, CF$_3$CH$_2$CH$_2$];
[A4, H, H, H, H, CF$_3$CF$_2$CH$_2$]; [A4, H, H, H, H, CF$_3$CF$_2$CF$_2$];
[A4, H, CN, H, H, CF$_3$]; [A4, H, CN, H, H, CF$_3$CH$_2$];
[A4, H, CN, H, H, CF$_3$CF$_2$]; [A4, H, CN, H, H, CF$_3$CH$_2$CH$_2$];
[A4, H, CN, H, H, CF$_3$CF$_2$CH$_2$]; [A4, H, CN, H, H, CF$_3$CF$_2$CF$_2$];
[A4, F, CN, H, H, CF$_3$]; [A4, F, CN, H, H, CF$_3$CH$_2$];
[A4, F, CN, H, H, CF$_3$CF$_2$]; [A4, F, CN, H, H, CF$_3$CH$_2$CH$_2$];
[A4, F, CN, H, H, CF$_3$CF$_2$CH$_2$]; [A4, F, CN, H, H, CF$_3$CF$_2$CF$_2$];
[A4, Cl, CN, H, H, CF$_3$]; [A4, Cl, CN, H, H, CF$_3$CH$_2$];
[A4, Cl, CN, H, H, CF$_3$CF$_2$]; [A4, Cl, CN, H, H, CF$_3$CH$_2$CH$_2$];
[A4, Cl, CN, H, H, CF$_3$CF$_2$CH$_2$]; [A4, Cl, CN, H, H, CF$_3$CF$_2$CF$_2$];
[A4, H, C(=O)NH$_2$, H, H, CF$_3$]; [A4, H, C(=O)NH$_2$, H, H, CF$_3$CH$_2$];
[A4, H, C(=O)NH$_2$, H, H, CF$_3$CF$_2$]; [A4, H, C(=O)NH$_2$, H, H, CF$_3$CH$_2$CH$_2$];
[A4, H, C(=O)NH$_2$, H, H, CF$_3$CF$_2$CH$_2$]; [A4, H, C(=O)NH$_2$, H, H, CF$_3$CF$_2$CF$_2$];
[A4, F, C(=O)NH$_2$, H, H, CF$_3$]; [A4, F, C(=O)NH$_2$, H, H, CF$_3$CH$_2$];
[A4, F, C(=O)NH$_2$, H, H, CF$_3$CF$_2$]; [A4, F, C(=O)NH$_2$, H, H, CF$_3$CH$_2$CH$_2$];
[A4, F, C(=O)NH$_2$, H, H, CF$_3$CF$_2$CH$_2$]; [A4, F, C(=O)NH$_2$, H, H, CF$_3$CF$_2$CF$_2$];
[A4, Cl, C(=O)NH$_2$, H, H, CF$_3$]; [A4, Cl, C(=O)NH$_2$, H, H, CF$_3$CH$_2$];
[A4, Cl, C(=O)NH$_2$, H, H, CF$_3$CF$_2$]; [A4, Cl, C(=O)NH$_2$, H, H, CF$_3$CH$_2$CH$_2$];
[A4, Cl, C(=O)NH$_2$, H, H, CF$_3$CF$_2$CH$_2$]; [A4, Cl, C(=O)NH$_2$, H, H, CF$_3$CF$_2$CF$_2$];
[A4, H, H, H, CN, CF$_3$]; [A4, H, H, H, CN, CF$_3$CH$_2$];
[A4, H, H, H, CN, CF$_3$CF$_2$]; [A4, H, H, H, CN, CF$_3$CH$_2$CH$_2$];
[A4, H, H, H, CN, CF$_3$CF$_2$CH$_2$]; [A4, H, H, H, CN, CF$_3$CF$_2$CF$_2$];
[A4, H, H, F, CN, CF$_3$]; [A4, H, H, F, CN, CF$_3$CH$_2$];
[A4, H, H, F, CN, CF$_3$CF$_2$]; [A4, H, H, F, CN, CF$_3$CH$_2$CH$_2$];
[A4, H, H, F, CN, CF$_3$CF$_2$CH$_2$]; [A4, H, H, F, CN, CF$_3$CF$_2$CF$_2$];
[A4, H, H, Cl, CN, CF$_3$]; [A4, H, H, Cl, CN, CF$_3$CH$_2$];
[A4, H, H, Cl, CN, CF$_3$CF$_2$]; [A4, H, H, Cl, CN, CF$_3$CH$_2$CH$_2$];
[A4, H, H, Cl, CN, CF$_3$CF$_2$CH$_2$]; [A4, H, H, Cl, CN, CF$_3$CF$_2$CF$_2$];
[A4, H, H, H, C(=O)NH$_2$, CF$_3$]; [A4, H, H, H, C(=O)NH$_2$, CF$_3$CH$_2$];
[A4, H, H, H, C(=O)NH$_2$, CF$_3$CF$_2$]; [A4, H, H, H, C(=O)NH$_2$, CF$_3$CH$_2$CH$_2$];

[A4, H, H, H, C(=O)NH$_2$, CF$_3$CF$_2$CH$_2$]; [A4, H, H, H, C(=O)NH$_2$, CF$_3$CF$_2$CF$_2$];
[A4, H, H, F, C(=O)NH$_2$, CF$_3$]; [A4, H, H, F, C(=O)NH$_2$, CF$_3$CH$_2$];
[A4, H, H, F, C(=O)NH$_2$, CF$_3$CF$_2$]; [A4, H, H, F, C(=O)NH$_2$, CF$_3$CH$_2$CH$_2$];
[A4, H, H, F, C(=O)NH$_2$, CF$_3$CF$_2$CH$_2$]; [A4, H, H, F, C(=O)NH$_2$, CF$_3$CF$_2$CF$_2$];
[A4, H, H, Cl, C(=O)NH$_2$, CF$_3$]; [A4, H, H, Cl, C(=O)NH$_2$, CF$_3$CH$_2$];
[A4, H, H, Cl, C(=O)NH$_2$, CF$_3$CF$_2$]; [A4, H, H, Cl, C(=O)NH$_2$, CF$_3$CH$_2$CH$_2$];
[A4, H, H, Cl, C(=O)NH$_2$, CF$_3$CF$_2$CH$_2$]; [A4, H, H, Cl, C(=O)NH$_2$, CF$_3$CF$_2$CF$_2$];
[A5, H, H, H, H, CF$_3$]; [A5, H, H, H, H, CF$_3$CH$_2$];
[A5, H, H, H, H, CF$_3$CF$_2$]; [A5, H, H, H, H, CF$_3$CH$_2$CH$_2$];
[A5, H, H, H, H, CF$_3$CF$_2$CH$_2$]; [A5, H, H, H, H, CF$_3$CF$_2$CF$_2$];
[A5, H, CN, H, H, CF$_3$]; [A5, H, CN, H, H, CF$_3$CH$_2$];
[A5, H, CN, H, H, CF$_3$CF$_2$]; [A5, H, CN, H, H, CF$_3$CH$_2$CH$_2$];
[A5, H, CN, H, H, CF$_3$CF$_2$CH$_2$]; [A5, H, CN, H, H, CF$_3$CF$_2$CF$_2$];
[A5, F, CN, H, H, CF$_3$]; [A5, F, CN, H, H, CF$_3$CH$_2$];
[A5, F, CN, H, H, CF$_3$CF$_2$]; [A5, F, CN, H, H, CF$_3$CH$_2$CH$_2$];
[A5, F, CN, H, H, CF$_3$CF$_2$CH$_2$]; [A5, F, CN, H, H, CF$_3$CF$_2$CF$_2$];
[A5, Cl, CN, H, H, CF$_3$]; [A5, Cl, CN, H, H, CF$_3$CH$_2$];
[A5, Cl, CN, H, H, CF$_3$CF$_2$]; [A5, Cl, CN, H, H, CF$_3$CH$_2$CH$_2$];
[A5, Cl, CN, H, H, CF$_3$CF$_2$CH$_2$]; [A15, Cl, CN, H, H, CF$_3$CF$_2$CF$_2$];
[A5, H, C(=O)NH$_2$, H, H, CF$_3$]; [A5, H, C(=O)NH$_2$, H, H, CF$_3$CH$_2$];
[A5, H, C(=O)NH$_2$, H, H, CF$_3$CF$_2$]; [A15, H, C(=O)NH$_2$, H, H, CF$_3$CH$_2$CH$_2$];
[A5, H, C(=O)NH$_2$, H, H, CF$_3$CF$_2$CH$_2$]; [A5, H, C(=O)NH$_2$, H, H, CF$_3$CF$_2$CF$_2$];
[A5, F, C(=O)NH$_2$, H, H, CF$_3$]; [A5, F, C(=O)NH$_2$, H, H, CF$_3$CH$_2$];
[A5, F, C(=O)NH$_2$, H, H, CF$_3$CF$_2$]; [A15, F, C(=O)NH$_2$, H, H, CF$_3$CH$_2$CH$_2$];
[A5, F, C(=O)NH$_2$, H, H, CF$_3$CF$_2$CH$_2$]; [A5, F, C(=O)NH$_2$, H, H, CF$_3$CF$_2$CF$_2$];
[A5, Cl, C(=O)NH$_2$, H, H, CF$_3$]; [A5, Cl, C(=O)NH$_2$, H, H, CF$_3$CH$_2$];
[A5, Cl, C(=O)NH$_2$, H, H, CF$_3$CF$_2$]; [A5, Cl, C(=O)NH$_2$, H, H, CF$_3$CH$_2$CH$_2$];
[A5, Cl, C(=O)NH$_2$, H, H, CF$_3$CF$_2$CH$_2$]; [A5, Cl, C(=O)NH$_2$, H, H, CF$_3$CF$_2$CF$_2$];
[A5, H, H, H, CN, CF$_3$]; [A5, H, H, H, CN, CF$_3$CH$_2$];
[A5, H, H, H, CN, CF$_3$CF$_2$]; [A5, H, H, H, CN, CF$_3$CH$_2$CH$_2$];
[A5, H, H, H, CN, CF$_3$CF$_2$CH$_2$]; [A15, H, H, H, CN, CF$_3$CF$_2$CF$_2$];
[A5, H, H, F, CN, CF$_3$]; [A5, H, H, F, CN, CF$_3$CH$_2$];
[A5, H, H, F, CN, CF$_3$CF$_2$]; [A5, H, H, F, CN, CF$_3$CH$_2$CH$_2$];
[A5, H, H, F, CN, CF$_3$CF$_2$CH$_2$]; [A5, H, H, F, CN, CF$_3$CF$_2$CF$_2$];
[A5, H, H, Cl, CN, CF$_3$]; [A5, H, H, Cl, CN, CF$_3$CH$_2$];
[A5, H, H, Cl, CN, CF$_3$CF$_2$]; [A5, H, H, Cl, CN, CF$_3$CH$_2$CH$_2$];
[A5, H, H, Cl, CN, CF$_3$CF$_2$CH$_2$]; [A5, H, H, Cl, CN, CF$_3$CF$_2$CF$_2$];
[A5, H, H, H, C(=O)NH$_2$, CF$_3$]; [A5, H, H, H, C(=O)NH$_2$, CF$_3$CH$_2$];
[A5, H, H, H, C(=O)NH$_2$, CF$_3$CF$_2$]; [A5, H, H, H, C(=O)NH$_2$ CF$_3$CH$_2$CH$_2$];

[A5, H, H, H, C(=O)NH$_2$, CF$_3$CF$_2$CH$_2$]; [A5, H, H, H, C(=O)NH$_2$, CF$_3$CF$_2$CF$_2$];
[A5, H, H, F, C(=O)NH$_2$CF$_3$]; [A5, H, H, F, C(=O)NH$_2$, CF$_3$CH$_2$];
[A5, H, H, F, C(=O)NH$_2$, CF$_3$CF$_2$]; [A5, H, H, F, C(=O)NH$_2$, CF$_3$CH$_2$CH$_2$];
[A5, H, H, F, C(=O)NH$_2$, CF$_3$CF$_2$CH$_2$]; [A5, H, H, F, C(=O)NH$_2$, CF$_3$CF$_2$CF$_2$];
[A5, H, H, Cl, C(=O)NH$_2$, CF$_3$]; [A5, H, H, Cl, C(=O)NH$_2$, CF$_3$CH$_2$];
[A5, H, H, Cl, C(=O)NH$_2$, CF$_3$CF$_2$]; [A5, H, H, Cl, C(=O)NH$_2$, CF$_3$CH$_2$CH$_2$];
[A5, H, H, Cl, C(=O)NH$_2$, CF$_3$CF$_2$CH$_2$]; [A5, H, H, Cl, C(=O)NH$_2$, CF$_3$CF$_2$CF$_2$];
[A5, H, C(=O)OCH$_3$, H, H, CF$_3$]; [A5, H, C(=O)OCH$_3$, H, H, CF$_3$CH$_2$];
[A5, H, C(=O)OCH$_3$, H, H, CF$_3$CF$_2$]; [A5, H, C(=O)OCH$_3$, H, H, CF$_3$CH$_2$CH$_2$];
[A5, F, C(=O)OCH$_3$, H, H, CF$_3$]; [A5, F, C(=O)OCH$_3$, H, H, CF$_3$CH$_2$];
[A5, F, C(=O)OCH$_3$, H, H, CF$_3$CF$_2$]; [A5, F, C(=O)OCH$_3$, H, H, CF$_3$CH$_2$CH$_2$];
[A5, Cl, C(=O)OCH$_3$, H, H, CF$_3$]; [A5, Cl, C(=O)OCH$_3$, H, H, CF$_3$CH$_2$];
[A5, Cl, C(=O)OCH$_3$, H, H, CF$_3$CF$_2$]; [A5, Cl, C(=O)OCH$_3$, H, H, CF$_3$CH$_2$CH$_2$];
[A5, H, H, H, C(=O)OCH$_3$, CF$_3$]; [A5, H, H, H, C(=O)OCH$_3$, CF$_3$CH$_2$];
[A5, H, H, H, C(=O)OCH$_3$, CF$_3$CF$_2$]; [A5, H, H, H, C(=O)OCH$_3$, CF$_3$CH$_2$CH$_2$];
[A5, H, H, F, C(=O)OCH$_3$, CF$_3$]; [A5, H, H, F, C(=O)OCH$_3$, CF$_3$CH$_2$];
[A5, H, H, F, C(=O)OCH$_3$, CF$_3$CF$_2$]; [A5, H, H, F, C(=O)OCH$_3$, CF$_3$CH$_2$CH$_2$];
[A5, H, H, Cl, C(=O)OCH$_3$, CF$_3$]; [A5, H, H, Cl, C(=O)OCH$_3$, CF$_3$CH$_2$];
[A5, H, H, Cl, C(=O)OCH$_3$CF$_3$CF$_2$]; [A5, H, H, Cl, C(=O)OCH$_3$, CF$_3$CH$_2$CH$_2$];
[A6, H, H, H, H, CF$_3$]; [A6, H, H, H, H, CF$_3$CH$_2$];
[A6, H, H, H, H, CF$_3$CF$_2$]; [A6, H, H, H, H, CF$_3$CH$_2$CH$_2$];
[A6, H, H, H, H, CF$_3$CF$_2$CH$_2$]; [A6, H, H, H, H, CF$_3$CF$_2$CF$_2$];
[A6, H, CN, H, H, CF$_3$]; [A6, H, CN, H, H, CF$_3$CH$_2$];
[A6, H, CN, H, H, CF$_3$CF$_2$]; [A6, H, CN, H, H, CF$_3$CH$_2$CH$_2$];
[A6, H, CN, H, H, CF$_3$CF$_2$CH$_2$]; [A6, H, CN, H, H, CF$_3$CF$_2$CF$_2$];
[A6, F, CN, H, H, CF$_3$]; [A6, F, CN, H, H, CF$_3$CH$_2$];
[A6, F, CN, H, H, CF$_3$CF$_2$]; [A6, F, CN, H, H, CF$_3$CH$_2$CH$_2$];
[A6, F, CN, H, H, CF$_3$CF$_2$CH$_2$]; [A6, F, CN, H, H, CF$_3$CF$_2$CF$_2$];
[A6, Cl, CN, H, H, CF$_3$]; [A6, Cl, CN, H, H, CF$_3$CH$_2$];
[A6, Cl, CN, H, H, CF$_3$CF$_2$]; [A6, Cl, CN, H, H, CF$_3$CH$_2$CH$_2$];
[A6, Cl, CN, H, H, CF$_3$CF$_2$CH$_2$]; [A6, Cl, CN, H, H, CF$_3$CF$_2$CF$_2$];
[A6, H, C(=O)NH$_2$, H, H, CF$_3$]; [A6, H, C(=O)NH$_2$, H, H, CF$_3$CH$_2$];
[A6, H, C(=O)NH$_2$, H, H, CF$_3$CF$_2$]; [A6, H, C(=O)NH$_2$, H, H, CF$_3$CH$_2$CH$_2$];
[A6, H, C(=O)NH$_2$, H, H, CF$_3$CF$_2$CH$_2$]; [A6, H, C(=O)NH$_2$, H, H, CF$_3$CF$_2$CF$_2$];
[A6, F, C(=O)NH$_2$, H, H, CF$_3$]; [A6, F, C(=O)NH$_2$, H, H, CF$_3$CH$_2$];
[A6, F, C(=O)NH$_2$, H, H, CF$_3$CF$_2$]; [A6, F, C(=O)NH$_2$, H, H, CF$_3$CH$_2$CH$_2$];
[A6, F, C(=O)NH$_2$, H, H, CF$_3$CF$_2$CH$_2$]; [A6, F, C(=O)NH$_2$, H, H, CF$_3$CF$_2$CF$_2$];

[A6, Cl, C(=O)NH₂, H, H, CF₃]; [A6, Cl, C(=O)NH₂, H, H, CF₃CH₂];
[A6, Cl, C(=O)NH₂, H, H, CF₃CF₂]; [A6, Cl, C(=O)NH₂, H, H, CF₃CH₂CH₂];
[A6, Cl, C(=O)NH₂, H, H, CF₃CF₂CH₂]; [A6, Cl, C(=O)NH₂, H, H, CF₃CF₂CF₂];
[A6, H, H, H, CN, CF₃]; [A6, H, H, H, CN, CF₃CH₂];
[A6, H, H, H, CN, CF₃CF₂]; [A6, H, H, H, CN, CF₃CH₂CH₂];
[A6, H, H, H, CN, CF₃CF₂CH₂]; [A6, H, H, H, CN, CF₃CF₂CF₂];
[A6, H, H, F, CN, CF₃]; [A6, H, H, F, CN, CF₃CH₂];
[A6, H, H, F, CN, CF₃CF₂]; [A6, H, H, F, CN, CF₃CH₂CH₂];
[A6, H, H, F, CN, CF₃CF₂CH₂]; [A6, H, H, F, CN, CF₃CF₂CF₂];
[A6, H, H, Cl, CN, CF₃]; [A6, H, H, Cl, CN, CF₃CH₂];
[A6, H, H, Cl, CN, CF₃CF₂]; [A6, H, H, Cl, CN, CF₃CH₂CH₂];
[A6, H, H, Cl, CN, CF₃CF₂CH₂]; [A6, H, H, Cl, CN, CF₃CF₂CF₂];
[A6, H, H, H, C(=O)NH₂, CF₃]; [A6, H, H, H, C(=O)NH₂, CF₃CH₂];
[A6, H, H, H, C(=O)NH₂, CF₃CF₂]; [A6, H, H, H, C(=O)NH₂, CF₃CH₂CH₂];
[A6, H, H, H, C(=O)NH₂, CF₃CF₂CH₂]; [A6, H, H, H, C(=O)NH₂, CF₃CF₂CF₂];
[A6, H, H, F, C(=O)NH₂, CF₃]; [A6, H, H, F, C(=O)NH₂CF₃CH₂];
[A6, H, H, F, C(=O)NH₂, CF₃CF₂]; [A6, H, H, F, C(=O)NH₂, CF₃CH₂CH₂];
[A6, H, H, F, C(=O)NH₂, CF₃CF₂CH₂]; [A6, H, H, F, C(=O)NH₂, CF₃CF₂CF₂];
[A6, H, H, Cl, C(=O)NH₂, CF₃]; [A6, H, H, Cl, C(=O)NH₂, CF₃CH₂];
[A6, H, H, Cl, C(=O)NH₂, CF₃CF₂]; [A6, H, H, Cl, C(=O)NH₂, CF₃CH₂CH₂];
[A6, H, H, Cl, C(=O)NH₂, CF₃CF₂CH₂]; [A6, H, H, Cl, C(=O)NH₂, CF₃CF₂CF₂];
[A7, H, H, H, H, CF₃]; [A7, H, H, H, H, CF₃CH₂];
[A7, H, H, H, H, CF₃CF₂]; [A7, H, H, H, H, CF₃CH₂CH₂];
[A7, H, H, H, H, CF₃CF₂CH₂]; [A7, H, H, H, H, CF₃CF₂CF₂];
[A7, H, CN, H, H, CF₃]; [A7, H, CN, H, H, CF₃CH₂];
[A7, H, CN, H, H, CF₃CF₂]; [A7, H, CN, H, H, CF₃CH₂CH₂];
[A7, H, CN, H, H, CF₃CF₂CH₂]; [A7, H, CN, H, H, CF₃CF₂CF₂];
[A7, F, CN, H, H, CF₃]; [A7, F, CN, H, H, CF₃CH₂];
[A7, F, CN, H, H, CF₃CF₂]; [A7, F, CN, H, H, CF₃CH₂CH₂];
[A7, F, CN, H, H, CF₃CF₂CH₂]; [A7, F, CN, H, H, CF₃CF₂CF₂];
[A7, Cl, CN, H, H, CF₃]; [A7, Cl, CN, H, H, CF₃CH₂];
[A7, Cl, CN, H, H, CF₃CF₂]; [A7, Cl, CN, H, H, CF₃CH₂CH₂];
[A7, Cl, CN, H, H, CF₃CF₂CH₂]; [A7, Cl, CN, H, H, CF₃CF₂CF₂];
[A7, H, C(=O)NH₂, H, H, CF₃]; [A7, H, C(=O)NH₂, H, H, CF₃CH₂];
[A7, H, C(=O)NH₂, H, CF₃CF₂]; [A7, H, C(=O)NH₂, H, H, CF₃CH₂CH₂];
[A7, H, C(=O)NH₂, H, H, CF₃CF₂CH₂]; [A7, H, C(=O)NH₂, H, H, CF₃CF₂CF₂];
[A7, F, C(=O)NH₂, H, H, CF₃]; [A7, F, O(=O)NH₂, H, H, CF₃CH₂];
[A7, F, C(=O)NH₂, H, H, CF₃CF₂]; [A7, F, C(=O)NH₂, H, H, CF₃CH₂CH₂];
[A7, F, O(=O)NH₂, H, H, CF₃CF₂CH₂]; [A7, F, C(=O)NH₂, H, H, CF₃CF₂CF₂];

[A7, Cl, C(=O)NH₂, H, H, CF₃]; [A7, Cl, C(=O)NH₂, H, H, CF₃CH₂];
[A7, Cl, C(=O)NH₂, H, H, CF₃CF₂]; [A7, Cl, C(=O)NH₂, H, H, CF₃CH₂CH₂];
[A7, Cl, C(=O)NH₂, H, H, CF₃CF₂CH₂]; [A7, Cl, C(=O)NH₂, H, H, CF₃CF₂CF₂];
[A7, H, H, H, CN, CF₃]; [A7, H, H, H, CN, CF₃CH₂];
[A7, H, H, H, CN, CF₃CF₂]; [A7, H, H, H, CN, CF₃CH₂CH₂];
[A7, H, H, H, CN, CF₃CF₂CH₂]; [A7, H, H, H, CN, CF₃CF₂CF₂];
[A7, H, H, F, CN, CF₃]; [A7, H, H, F, CN, CF₃CH₂];
[A7, H, H, F, CN, CF₃CF₂]; [A7, H, H, F, CN, CF₃CH₂CH₂];
[A7, H, H, F, CN, CF₃CF₂CH₂]; [A7, H, H, F, CN, CF₃CF₂CF₂];
[A7, H, H, Cl, CN, CF₃]; [A7, H, H, Cl, CN, CF₃CH₂];
[A7, H, H, Cl, CN, CF₃CF₂]; [A7, H, H, Cl, CN, CF₃CH₂CH₂];
[A7, H, H, Cl, CN, CF₃CF₂CH₂]; [A7, H, H, Cl, CN, CF₃CF₂CF₂];
[A7, H, H, H, C(=O)NH₂, CF₃]; [A7, H, H, H, C(=O)NH₂, CF₃CH₂];
[A7, H, H, H, C(=O)NH₂, CF₃CF₂]; [A7, H, H, H, C(=O)NH₂, CF₃CH₂CH₂];
[A7, H, H, H, C(=O)NH₂, CF₃CF₂CH₂]; [A7, H, H, H, C(=O)NH₂ CF₃CF₂CF₂];
[A7, H, H, F, C(=O)NH₂, CF₃]; [A7, H, H, F, C(=O)NH₂, CF₃CH₂];
[A7, H, H, F, C(=O)NH₂, CF₃CF₂]; [A7, H, H, F, C(=O)NH₂, CF₃CH₂CH₂];
[A7, H, H, F, C(=O)NH₂, CF₃CF₂CH₂]; [A7, H, H, F, C(=O)NH₂, CF₃CF₂CF₂];
[A7, H, H, Cl, C(=O)NH₂, CF₃]; [A7, H, H, Cl, C(=O)NH₂, CF₃CH₂];
[A7, H, H, Cl, C(=O)NH₂, CF₃CF₂]; [A7, H, H, Cl, C(=O)NH₂, CF₃CH₂CH₂];
[A7, H, H, Cl, C(=O)NH₂, CF₃CF₂CH₂]; [A7, H, H, Cl, C(=O)NH₂, CF₃CF₂CF₂];
[A8, H, H, H, H, CF₃]; [A8, H, H, H, H, CF₃CH₂];
[A8, H, H, H, H, CF₃CF₂]; [A8, H, H, H, H, CF₃CH₂CH₂];
[A8, H, H, H, H, CF₃CF₂CH₂]; [A8, H, H, H, H, CF₃CF₂CF₂];
[A8, H, CN, H, H, CF₃]; [A8, H, CN, H, H, CF₃CH₂];
[A8, H, CN, H, H, CF₃CF₂]; [A8, H, CN, H, H, CF₃CH₂CH₂];
[A8, H, CN, H, H, CF₃CF₂CH₂]; [A8, H, CN, H, H, CF₃CF₂CF₂];
[A8, F, CN, H, H, CF₃]; [A8, F, CN, H, H, CF₃CH₂];
[A8, F, CN, H, H, CF₃CF₂]; [A8, F, CN, H, H, CF₃CH₂CH₂];
[A8, F, CN, H, H, CF₃CF₂CH₂]; [A8, F, CN, H, H, CF₃CF₂CF₂];
[A8, Cl, CN, H, H, CF₃]; [A8, Cl, CN, H, H, CF₃CH₂];
[A8, Cl, CN, H, H, CF₃CF₂]; [A8, Cl, CN, H, H, CF₃CH₂CH₂];
[A8, Cl, CN, H, H, CF₃CF₂CH₂]; [A8, Cl, CN, H, H, CF₃CF₂CF₂];
[A8, H, C(=O)NH₂, H, H, CF₃]; [A8, H, C(=O)NH₂, H, H, CF₃CH₂];
[A8, H, C(=O)NH₂, H, H, CF₃CF₂]; [A8, H, C(=O)NH₂, H, H, CF₃CH₂CH₂];
[A8, H, C(=O)NH₂, H, H, CF₃CF₂CH₂]; [A8, H, C(=O)NH₂, H, H, CF₃CF₂CF₂];
[A8, F, C(=O)NH₂, H, H, CF₃]; [A8, F, C(=O)NH₂, H, H, CF₃CH₂];
[A8, F, C(=O)NH₂, H, H, CF₃CF₂]; [A8, F, C(=O)NH₂, H, H, CF₃CH₂CH₂];
[A8, F, C(=O)NH₂, H, H, CF₃CF₂CH₂]; [A8, F, C(=O)NH₂, H, H, CF₃CF₂CF₂];

[A8, Cl, C(=O)NH₂, H, H, CF₃]; [A8, Cl, C(=O)NH₂, H, H, CF₃CH₂];
[A8, Cl, C(=O)NH₂, H, H, CF₃CF₂]; [A8, Cl, C(=O)NH₂, H, H, CF₃CH₂CH₂];
[A8, Cl, C(=O)NH₂, H, H, CF₃CF₂CH₂]; [A8, Cl, C(=O)NH₂, H, H, CF₃CF₂CF₂];
[A8, H, H, H, CN, CF₃]; [A8, H, H, H, CN, CF₃CH₂];
[A8, H, H, H, CN, CF₃CF₂]; [A8, H, H, H, CN, CF₃CH₂CH₂];
[A8, H, H, H, CN, CF₃CF₂CH₂]; [A8, H, H, H, CN, CF₃CF₂CF₂];
[A8, H, H, F, CN, CF₃]; [A8, H, H, F, CN, CF₃CH₂];
[A8, H, H, F, CN, CF₃CF₂]; [A8, H, H, F, CN, CF₃CH₂CH₂];
[A8, H, H, F, CN, CF₃CF₂CH₂]; [A8, H, H, F, CN, CF₃CF₂CF₂];
[A8, H, H, Cl, CN, CF₃]; [A8, H, H, Cl, CN, CF₃CH₂];
[A8, H, H, Cl, CN, CF₃CF₂]; [A8, H, H, Cl, CN, CF₃CH₂CH₂];
[A8, H, H, Cl, CN, CF₃CF₂CH₂]; [A8, H, H, Cl, CN, CF₃CF₂CF₂];
[A8, H, H, H, C(=O)NH₂, CF₃]; [A8, H, H, H, C(=O)NH₂, CF₃CH₂];
[A8, H, H, H, C(=O)NH₂, CF₃CF₂]; [A8, H, H, H, C(=O)NH₂, CF₃CH₂CH₂];
[A8, H, H, H, C(=O)NH₂CF₃CF₂CH₂]; [A8, H, H, H, C(=O)NH₂, CF₃CF₂CF₂];
[A8, H, H, F, C(=O)NH₂, CF₃]; [A8, H, H, F, C(=O)NH₂, CF₃CH₂];
[A8, H, H, F, C(=O)NH₂CF₃CF₂]; [A8, H, H, F, C(=O)NH₂, CF₃CH₂CH₂];
[A8, H, H, F, C(=O)NH₂CF₃CF₂CH₂]; [A8, H, H, F, C(=O)NH₂, CF₃CF₂CF₂];
[A8, H, H, Cl, C(=O)NH₂, CF₃]; [A8, H, H, Cl, C(=O)NH₂, CF₃CH₂];
[A8, H, H, Cl, C(=O)NH₂, CF₃CF₂]; [A8, H, H, Cl, (=O)NH₂, CF₃CH₂CH₂];
[A8, H, H, Cl, C(=O)NH₂, CF₃CF₂CH₂]; [A8, H, H, Cl, C(=O)NH₂, CF₃CF₂CF₂];
[A9, H, H, H, H, CF₃]; [A9, H, H, H, H, CF₃CH₂];
[A9, H, H, H, H, CF₃CF₂]; [A9, H, H, H, H, CF₃CH₂CH₂];
[A9, H, H, H, H, CF₃CF₂CH₂]; [A9, H, H, H, H, CF₃CF₂CF₂];
[A9, H, CN, H, H, CF₃]; [A9, H, CN, H, H, CF₃CH₂];
[A9, H, CN, H, H, CF₃CF₂]; [A9, H, CN, H, H, CF₃CH₂CH₂];
[A9, H, CN, H, H, CF₃CF₂CH₂]; [A9, H, CN, H, H, CF₃CF₂CF₂];
[A9, F, CN, H, H, CF₃]; [A9, F, CN, H, H, CF₃CH₂];
[A9, F, CN, H, H, CF₃CF₂]; [A9, F, CN, H, H, CF₃CH₂CH₂];
[A9, F, CN, H, H, CF₃CF₂CH₂]; [A9, F, CN, H, H, CF₃CF₂CF₂];
[A9, Cl, CN, H, H, CF₃]; [A9, Cl, CN, H, H, CF₃CH₂];
[A9, Cl, CN, H, H, CF₃CF₂]; [A9, Cl, CN, H, H, CF₃CH₂CH₂];
[A9, Cl, CN, H, H, CF₃CF₂CH₂]; [A9, Cl, CN, H, H, CF₃CF₂CF₂];
[A9, H, C(=O)NH₂, H, H, CF₃]; [A9, H, C(=O)NH₂, H, H, CF₃CH₂];
[A9, H, C(=O)NH₂, H, H, CF₃CF₂]; [A9, H, C(=O)NH₂, H, H, CF₃CH₂CH₂];
[A9, H, C(=O)NH₂, H, H, CF₃CF₂CH₂]; [A9, H, C(=O) NH₂, H, H, CF₃CF₂CF₂];
[A9, F, C(=O)NH₂, H, H, CF₃]; [A9, F, C(=O)NH₂, H, H, CF₃CH₂];
[A9, F, C(=O)NH₂, H, H, CF₃CF₂]; [A9, F, C(=O)NH₂, H, H, CF₃CH₂CH₂];
[A9, F, C(=O)NH₂, H, H, CF₃CF₂CH₂]; [A9, F, C(=O) NH₂, H, H, CF₃CF₂CF₂];
[A9, Cl, C(=O)NH₂, H, H, CF₃]; [A9, Cl, C(=O)NH₂, H, H, CF₃CH₂];
[A9, Cl, C(=O)NH₂, H, H, CF₃CF₂]; [A9, Cl, C(=O)NH₂, H, H, CF₃CH₂CH₂];
[A9, Cl, C(=O)NH₂, H, H, CF₃CF₂CH₂]; [A9, Cl, C(=O) NH₂, H, H, CF₃CF₂CF₂];
[A9, H, H, H, CN, CF₃]; [A9, H, H, H, CN, CF₃CH₂];
[A9, H, H, H, CN, CF₃CF₂]; [A9, H, H, H, CN, CF₃CH₂CH₂];
[A9, H, H, H, CN, CF₃CF₂CH₂]; [A9, H, H, H, CN, CF₃CF₂CF₂];
[A9, H, H, F, CN, CF₃]; [A9, H, H, F, CN, CF₃CH₂];
[A9, H, H, F, CN, CF₃CF₂]; [A9, H, H, F, CN, CF₃CH₂CH₂];
[A9, H, H, F, CN, CF₃CF₂CH₂]; [A9, H, H, F, CN, CF₃CF₂CF₂];
[A9, H, H, Cl, CN, CF₃]; [A9, H, H, Cl, CN, CF₃CH₂]; [A9, H, H, Cl, CN, CF₃CF₂]; [A9, H, H, Cl, CN, CF₃CH₂CH₂];
[A9, H, H, Cl, CN, CF₃CF₂CH₂]; [A9, H, H, Cl, CN, CF₃CF₂CF₂];
[A9, H, H, H, C(=O)NH₂, CF₃]; [A9, H, H, H, C(=O)NH₂, CF₃CH₂];
[A9, H, H, H, C(=O)NH₂, CF₃CF₂]; [A9, H, H, H, C(=O) NH₂, CF₃CH₂CH₂];
[A9, H, H, H, C(=O)NH₂, CF₃CF₂CH₂]; [A9, H, H, H, C(=O)NH₂, CF₃CF₂CF₂];
[A9, H, H, F, C(=O)NH₂, CF₃]; [A9, H, H, F, C(=O)NH₂, CF₃CH₂];
[A9, H, H, F, C(=O)NH₂, CF₃CF₂]; [A9, H, H, F, C(=O) NH₂, CF₃CH₂CH₂];
[A9, H, H, F, C(=O)NH₂, CF₃CF₂CH₂]; [A9, H, H, F, C(=O)NH₂ CF₃CF₂CF₂];
[A9, H, H, Cl, C(=O)NH₂, CF₃]; [A9, H, H, Cl, C(=O)NH₂, CF₃CH₂];
[A9, H, H, Cl, C(=O)NH₂, CF₃CF₂]; [A9, H, H, Cl, C(=O) NH₂, CF₃CH₂CH₂];
[A9, H, H, Cl, C(=O)NH₂CF₃CF₂CH₂]; [A9, H, H, Cl, C(=O)NH₂, CF₃CF₂CF₂];
[A9, H, C(=O)OCH₃, H, H, CF₃]; [A9, H, C(=O)OCH₃, H, H, CF₃CH₂];
[A9, H, C(=O)OCH₃, H, H, CF₃CF₂]; [A9, H, C(=O) OCH₃, H, H, CF₃CH₂CH₂];
[A9, F, C(=O)OCH₃, H, CF₃]; [A9, F, C(=O)OCH₃H, H, CF₃CH₂];
[A9, F, C(=O)OCH₃, H, H, CF₃CF₂]; [A9, F, C(=O)OCH₃, H, H, CF₃CH₂CH₂];
[A9, Cl, C(=O)OCH₃, H, H, CF₃]; [A9, Cl, C(=O)OCH₃, H, H, CF₃CH₂];
[A9, Cl, C(=O)OCH₃H, H, CF₃CF₂]; [A9, Cl, C(=O) OCH₃, H, H, CF₃CH₂CH₂];
[A9, H, H, H, C(=O)OCH₃CF₃]; [A9, H, H, H, C(=O) OCH₃, CF₃CH₂];
[A9, H, H, H, C(=O)OCH₃CF₃CF₂]; [A9, H, H, H, C(=O) OCH₃, CF₃CH₂CH₂];
[A9, H, H, F, C(=O)OCH₃, CF₃]; [A9, H, H, F, C(=O) OCH₃ CF₃CH₂];
[A9, H, H, F, C(=O)OCH₃CF₃CF₂]; [A9, H, H, F, C(=O) OCH₃, CF₃CH₂CH₂];
[A9, H, H, Cl, C(=O)OCH₃CF₃]; [A9, H, H, Cl, C(=O) OCH₃, CF₃CH₂];
[A9, H, H, Cl, C(=O)OCH₃CF₃CF₂]; [A9, H, H, Cl, C(=O) OCH₃, CF₃CH₂CH₂];
[A10, H, H, H, H, CF₃]; [A10, H, H, H, H, CF₃CH₂];
[A10, H, H, H, H, CF₃CF₂]; [A10, H, H, H, H, CF₃CH₂CH₂];
[A10, H, H, H, H, CF₃CF₂CH₂]; [A10, H, H, H, H, CF₃CF₂CF₂];
[A10, H, CN, H, H, CF₃]; [A10, H, CN, H, H, CF₃CH₂];
[A10, H, CN, H, H, CF₃CF₂]; [A10, H, CN, H, H, CF₃CH₂CH₂];

[A10, H, CN, H, H, CF₃CF₂CH₂]; [A10, H, CN, H, H, CF₃CF₂CF₂];
[A10, F, CN, H, H, CF₃]; [A10, F, CN, H, H, CF₃CH₂];
[A10, F, CN, H, H, CF₃CF₂]; [A10, F, CN, H, H, CF₃CH₂CH₂];
[A10, F, CN, H, H, CF₃CF₂CH₂]; [A10, F, CN, H, H, CF₃CF₂CF₂];
[A10, Cl, CN, H, H, CF₃]; [A10, Cl, CN, H, H, CF₃CH₂];
[A10, Cl, CN, H, H, CF₃CF₂]; [A10, Cl, CN, H, H, CF₃CH₂CH₂];
[A10, Cl, CN, H, H, CF₃CF₂CH₂]; [A10, Cl, CN, H, H, CF₃CF₂CF₂];
[A10, H, C(=O)NH₂, H, H, CF₃]; [A10, H, C(=O)NH₂, H, H, CF₃CH₂];
[A10, H, C(=O)NH₂, H, H, CF₃CF₂]; [A10, H, C(=O)NH₂, H, H, CF₃CH₂CH₂];
[A10, H, C(=O)NH₂, H, H, CF₃CF₂CH₂]; [A10, H, C(=O)NH₂, H, H, CF₃CF₂CF₂];
[A10, F, C(=O)NH₂, H, H, CF₃]; [A10, F, C(=O)NH₂, H, H, CF₃CH₂];
[A10, F, C(=O)NH₂, H, H, CF₃CF₂]; [A10, F, C(=O)NH₂, H, H, CF₃CH₂CH₂];
[A10, F, C(=O)NH₂, H, H, CF₃CF₂CH₂]; [A10, F, C(=O)NH₂, H, H, CF₃CF₂CF₂];
[A10, Cl, C(=O)NH₂, H, H, CF₃]; [A10, Cl, C(=O)NH₂, H, H, CF₃CH₂];
[A10, Cl, C(=O)NH₂, H, H, CF₃CF₂]; [A10, Cl, C(=O)NH₂, H, H, CF₃CH₂CH₂];
[A10, Cl, C(=O)NH₂, H, H, CF₃CF₂CH₂]; [A10, Cl, C(=O)NH₂, H, H, CF₃CF₂CF₂];
[A10, H, H, H, CN, CF₃]; [A10, H, H, H, CN, CF₃CH₂];
[A10, H, H, H, CN, CF₃CF₂]; [A10, H, H, H, CN, CF₃CH₂CH₂];
[A10, H, H, H, CN, CF₃CF₂CH₂]; [A10, H, H, H, CN, CF₃CF₂CF₂];
[A10, H, H, F, CN, CF₃]; [A10, H, H, F, CN, CF₃CH₂];
[A10, H, H, F, CN, CF₃CF₂]; [A10, H, H, F, CN, CF₃CH₂CH₂];
[A10, H, H, F, CN, CF₃CF₂CH₂]; [A10, H, H, F, CN, CF₃CF₂CF₂];
[A10, H, H, Cl, CN, CF₃]; [A10, H, H, Cl, CN, CF₃CH₂];
[A10, H, H, Cl, CN, CF₃CF₂]; [A10, H, H, Cl, CN, CF₃CH₂CH₂];
[A10, H, H, Cl, CN, CF₃CF₂CH₂]; [A10, H, H, Cl, CN, CF₃CF₂CF₂];
[A10, H, H, H, C(=O)NH₂, CF₃]; [A10, H, H, H, C(=O)NH₂, CF₃CH₂];
[A10, H, H, H, C(=O)NH₂, CF₃CF₂]; [A10, H, H, H, C(=O)NH₂, CF₃CH₂CH₂];
[A10, H, H, H, C(=O)NH₂, CF₃CF₂CH₂]; [A10, H, H, H, C(=O)NH₂, CF₃CF₂CF₂];
[A10, H, H, F, C(=O)NH₂, CF₃]; [A10, H, H, F, C(=O)NH₂, CF₃CH₂];
[A10, H, H, F, C(=O)NH₂, CF₃CF₂]; [A10, H, H, F, C(=O)NH₂, CF₃CH₂CH₂];
[A10, H, H, F, C(=O)NH₂, CF₃CF₂CH₂]; [A10, H, H, F, C(=O)NH₂, CF₃CF₂CF₂];
[A10, H, H, Cl, C(=O)NH₂, CF₃]; [A10, H, H, Cl, C(=O)NH₂, CF₃CH₂];
[A10, H, H, Cl, C(=O)NH₂, CF₃CF₂]; [A10, H, H, Cl, C(=O)NH₂, CF₃CH₂CH₂];
[A10, H, H, Cl, C(=O)NH₂, CF₃CF₂CH₂]; [A10, H, H, Cl, C(=O)NH₂, CF₃CF₂CF₂];
[A10, H, O(=O)OCH₃, H, H, CF₃]; [A10, H, C(=O)OCH₃, H, H, CF₃CH₂];
[A10, H, C(=O)OCH₃, H, H, CF₃CF₂]; [A10, H, C(=O)OCH₃, H, H, CF₃CH₂CH₂];
[A10, F, C(=O)OCH₃, H, H, CF₃]; [A10, F, C(=O)OCH₃, H, H, CF₃CH₂];
[A10, F, C(=O)OCH₃, H, H, CF₃CF₂]; [A10, F, C(=O)OCH₃, H, H, CF₃CH₂CH₂];
[A10, Cl, C(=O)OCH₃, H, H, CF₃]; [A10, Cl, C(=O)OCH₃, H, H, CF₃CH₂];
[A10, Cl, C(=O)OCH₃, H, H, CF₃CF₂]; [A10, Cl, C(=O)OCH₃, H, H, CF₃CH₂CH₂];
[A10, H, H, H, C(=O)OCH₃, CF₃]; [A10, H, H, H, C(=O)OCH₃, CF₃CH₂];
[A10, H, H, H, C(=O)OCH₃, CF₃CF₂]; [A10, H, H, H, C(=O)OCH₃ CF₃CH₂CH₂];
[A10, H, H, F, C(=O)OCH₃, CF₃]; [A10, H, H, F, C(=O)OCH₃, CF₃CH₂];
[A10, H, H, F, C(=O)OCH₃, CF₃CF₂]; [A10, H, H, F, C(=O)OCH₃, CF₃CH₂CH₂];
[A10, H, H, Cl, C(=O)OCH₃, CF₃]; [A10, H, H, Cl, C(=O)OCH₃, CF₃CH₂];
[A10, H, H, Cl, C(=O)OCH₃CF₃CF₂]; [A10, H, H, Cl, C(=O)OCH₃, CF₃CH₂CH₂];
[A11, H, H, H, H, CF₃]; [A11, H, H, H, H, CF₃CH₂];
[A11, H, H, H, H, CF₃CF₂]; [A11, H, H, H, H, CF₃CH₂CH₂];
[A11, H, H, H, H, CF₃CF₂CH₂]; [A11, H, H, H, H, CF₃CF₂CF₂];
[A11, H, CN, H, H, CF₃]; [A11, H, CN, H, H, CF₃CH₂];
[A11, H, CN, H, H, CF₃CF₂]; [A11, H, CN, H, H, CF₃CH₂CH₂];
[A11, H, CN, H, H, CF₃CF₂CH₂]; [A11, H, CN, H, H, CF₃CF₂CF₂];
[A11, F, CN, H, H, CF₃]; [A11, F, CN, H, H, CF₃CH₂];
[A11, F, CN, H, H, CF₃CF₂]; [A11, F, CN, H, H, CF₃CH₂CH₂];
[A11, F, CN, H, H, CF₃CF₂CH₂]; [A11, F, CN, H, H, CF₃CF₂CF₂];
[A11, Cl, CN, H, H, CF₃]; [A11, Cl, CN, H, H, CF₃CH₂];
[A11, Cl, CN, H, H, CF₃CF₂]; [A11, Cl, CN, H, H, CF₃CH₂CH₂];
[A11, Cl, CN, H, H, CF₃CF₂CH₂]; [A11, Cl, CN, H, H, CF₃CF₂CF₂];
[A11, H, C(=O)NH₂, H, H, CF₃]; [A11, H, C(=O)NH₂, H, H, CF₃CH₂];
[A11, H, C(=O)NH₂, H, H, CF₃CF₂]; [A11, H, C(=O)NH₂, H, H, CF₃CH₂CH₂];
[A11, H, O(=O)NH₂, H, H, CF₃CF₂CH₂]; [A11, H, C(=O)NH₂, H, H, CF₃CF₂CF₂];
[A11, F, C(=O)NH₂, H, H, CF₃]; [A11, F, C(=O)NH₂, H, H, CF₃CH₂];
[A11, F, C(=O)NH₂, H, H, CF₃CF₂]; [A11, F, C(=O)NH₂, H, H, CF₃CH₂CH₂];
[A11, F, C(=O)NH₂, H, H, CF₃CF₂CH₂]; [A11, F, C(=O)NH₂, H, H, CF₃CF₂CF₂];
[A11, Cl, C(=O)NH₂, H, H, CF₃]; [A11, Cl, C(=O)NH₂, H, H, CF₃CH₂];
[A11, Cl, C(=O)NH₂, H, H, CF₃CF₂]; [A11, Cl, C(=O)NH₂, H, H, CF₃CH₂CH₂];
[A11, Cl, C(=O)NH₂, H, H, CF₃CF₂CH₂]; [A11, Cl, C(=O)NH₂, H, H, CF₃CF₂CF₂];
[A11, H, H, H, CN, CF₃]; [A11, H, H, H, CN, CF₃CH₂];
[A11, H, H, H, CN, CF₃CF₂]; [A11, H, H, H, CN, CF₃CH₂CH₂];
[A11, H, H, H, CN, CF₃CF₂CH₂]; [A11, H, H, H, CN, CF₃CF₂CF₂];
[A11, H, H, F, CN, CF₃]; [A11, H, H, F, CN, CF₃CH₂];
[A11, H, H, F, CN, CF₃CF₂]; [A11, H, H, F, CN, CF₃CH₂CH₂];
[A11, H, H, F, CN, CF₃CF₂CH₂]; [A11, H, H, F, CN, CF₃CF₂CF₂];

[A11, H, H, Cl, CN, CF$_3$]; [A11, H, H, Cl, CN, CF$_3$CH$_2$];
[A11, H, H, Cl, CN, CF$_3$CF$_2$]; [A11, H, H, Cl, CN, CF$_3$CH$_2$CH$_2$];
[A11, H, H, Cl, CN, CF$_3$CF$_2$CH$_2$]; [A11, H, H, Cl, CN, CF$_3$CF$_2$CF$_2$];
[A11, H, H, H, C(=O)NH$_2$, CF$_3$]; [A11, H, H, H, C(=O)NH$_2$, CF$_3$CH$_2$];
[A11, H, H, H, C(=O)NH$_2$, CF$_3$CF$_2$]; [A11, H, H, H, C(=O)NH$_2$, CF$_3$CH$_2$CH$_2$];
[A11, H, H, H, C(=O)NH$_2$, CF$_3$CF$_2$CH$_2$]; [A11, H, H, H, C(=O)NH$_2$, CF$_3$CF$_2$CF$_2$];
[A11, H, H, F, C(=O)NH$_2$, CF$_3$]; [A11, H, H, F, C(=O)NH$_2$, CF$_3$CH$_2$];
[A11, H, H, F, C(=O)NH$_2$, CF$_3$CF$_2$]; [A11, C(=O)NH$_2$, CF$_3$CH$_2$CH$_2$];
[A11, H, H, F, C(=O)NH$_2$, CF$_3$CF$_2$CH$_2$]; [A11, H, H, F, C(=O)NH$_2$, CF$_3$CF$_2$CF$_2$];
[A11, H, H, Cl, C(=O)NH$_2$, CF$_3$]; [A11, H, H, Cl, C(=O)NH$_2$, CF$_3$CH$_2$];
[A11, H, H, Cl, C(=O)NH$_2$, CF$_3$CF$_2$]; [A11, H, H, Cl, C(=O)NH$_2$, CF$_3$CH$_2$CH$_2$];
[A11, H, H, Cl, C(=O)NH$_2$, CF$_3$CF$_2$CH$_2$]; [A11, H, H, Cl, C(=O)NH$_2$, CF$_3$CF$_2$CF$_2$];
[A11, H, C(=O)OCH$_3$, H, H, CF$_3$]; [A11, H, C(=O)OCH$_3$, H, H, CF$_3$CH$_2$];
[A11, H, C(=O)OCH$_3$, H, H, CF$_3$CF$_2$]; [A11, H, C(=O)OCH$_3$, H, H, CF$_3$CH$_2$CH$_2$];
[A11, F, C(=O)OCH$_3$, H, H, CF$_3$]; [A11, F, C(=O)OCH$_3$, H, H, CF$_3$CH$_2$];
[A11, F, C(=O)OCH$_3$, H, H, CF$_3$CF$_2$]; [A11, F, C(=O)OCH$_3$, H, H, CF$_3$CH$_2$CH$_2$];
[A11, Cl, C(=O)OCH$_3$, H, H, CF$_3$]; [A11, Cl, C(=O)OCH$_3$, H, H, CF$_3$CH$_2$];
[A11, Cl, C(=O)OCH$_3$, H, H, CF$_3$CF$_2$]; [A11, Cl, C(=O)OCH$_3$, H, CF$_3$CH$_2$CH$_2$];
[A11, H, H, H, C(=O)OCH$_3$, CF$_3$]; [A11, H, H, H, C(=O)OCH$_3$, CF$_3$CH$_2$];
[A11, H, H, H, C(=O)OCH$_3$, CF$_3$CF$_2$]; [A11, H, H, H, C(=O)OCH$_3$, CF$_3$CH$_2$CH$_2$];
[A11, H, H, F, C(=O)OCH$_3$, CF$_3$]; [A11, H, H, F, C(=O)OCH$_3$, CF$_3$CH$_2$];
[A11, H, H, F, C(=O)OCH$_3$, CF$_3$CF$_2$]; [A11, H, H, F, C(=O)OCH$_3$, CF$_3$CH$_2$CH$_2$];
[A11, H, H, Cl, C(=O)OCH$_3$, CF$_3$]; [A11, H, H, Cl, C(=O)OCH$_3$, CF$_3$CH$_2$];
[A11, H, H, Cl, C(=O)OCH$_3$, CF$_3$CF$_2$]; [A11, H, H, Cl, C(=O)OCH$_3$, CF$_3$CH$_2$CH$_2$];
[A12, H, H, H, H, CF$_3$]; [A12, H, H, H, H, CF$_3$CH$_2$];
[A12, H, H, H, H, CF$_3$CF$_2$]; [A12, H, H, H, H, CF$_3$CH$_2$CH$_2$];
[A12, H, H, H, H, CF$_3$CF$_2$CH$_2$]; [A12, H, H, H, H, CF$_3$CF$_2$CF$_2$];
[A12, H, CN, H, H, CF$_3$]; [A12, H, CN, H, H, CF$_3$CH$_2$];
[A12, H, CN, H, H, CF$_3$CF$_2$]; [A12, H, CN, H, H, CF$_3$CH$_2$CH$_2$];
[A12, H, CN, H, H, CF$_3$CF$_2$CH$_2$]; [A12, H, CN, H, H, CF$_3$CF$_2$CF$_2$];
[A12, F, CN, H, H, CF$_3$]; [A12, F, CN, H, H, CF$_3$CH$_2$];
[A12, F, CN, H, H, CF$_3$CF$_2$]; [A12, F, CN, H, H, CF$_3$CH$_2$CH$_2$];
[A12, F, CN, H, H, CF$_3$CF$_2$CH$_2$]; [A12, F, CN, H, H, CF$_3$CF$_2$CF$_2$];
[A12, Cl, CN, H, H, CF$_3$]; [A12, Cl, CN, H, H, CF$_3$CH$_2$];
[A12, Cl, CN, H, H, CF$_3$CF$_2$]; [A12, Cl, CN, H, H, CF$_3$CH$_2$CH$_2$];
[A12, Cl, CN, H, H, CF$_3$CF$_2$CH$_2$]; [A12, Cl, CN, H, H, CF$_3$CF$_2$CF$_2$];
[A12, H, C(=O)NH$_2$, H, H, CF$_3$]; [A12, H, C(=O)NH$_2$, H, H, CF$_3$CH$_2$];
[A12, H, C(=O)NH$_2$, H, H, CF$_3$CF$_2$]; [A12, H, C(=O)NH$_2$, H, H, CF$_3$CH$_2$CH$_2$];
[A12, H, C(=O)NH$_2$, H, H, CF$_3$CF$_2$CH$_2$]; [A12, H, C(=O)NH$_2$, H, H, CF$_3$CF$_2$CF$_2$];
[A12, F, C(=O)NH$_2$, H, H, CF$_3$]; [A12, F, C(=O)NH$_2$, H, H, CF$_3$CH$_2$];
[A12, F, C(=O)NH$_2$, H, H, CF$_3$CF$_2$]; [A12, F, C(=O)NH$_2$, H, H, CF$_3$CH$_2$CH$_2$];
[A12, F, C(=O)NH$_2$, H, H, CF$_3$CF$_2$CH$_2$]; [A12, F, C(=O)NH$_2$, H, H, CF$_3$CF$_2$CF$_2$];
[A12, Cl, C(=O)NH$_2$, H, H, CF$_3$]; [A12, Cl, C(=O)NH$_2$, H, H, CF$_3$CH$_2$];
[A12, Cl, C(=O)NH$_2$, H, H, CF$_3$CF$_2$]; [A12, Cl, C(=O)NH$_2$, H, H, CF$_3$CH$_2$CH$_2$];
[A12, Cl, C(=O)NH$_2$, H, H, CF$_3$CF$_2$CH$_2$]; [A12, Cl, C(=O)NH$_2$, H, H, CF$_3$CF$_2$CF$_2$];
[A12, H, H, H, CN, CF$_3$]; [A12, H, H, H, CN, CF$_3$CH$_2$];
[A12, H, H, H, CN, CF$_3$CF$_2$]; [A12, H, H, H, CN, CF$_3$CH$_2$CH$_2$];
[A12, H, H, H, CN, CF$_3$CF$_2$CH$_2$]; [A12, H, H, H, CN, CF$_3$CF$_2$CF$_2$];
[A12, H, H, F, CN, CF$_3$]; [A12, H, H, F, CN, CF$_3$CH$_2$];
[A12, H, H, F, CN, CF$_3$CF$_2$]; [A12, H, H, F, CN, CF$_3$CH$_2$CH$_2$];
[A12, H, H, F, CN, CF$_3$CF$_2$CH$_2$]; [A12, H, H, F, CN, CF$_3$CF$_2$CF$_2$];
[A12, H, H, Cl, CN, CF$_3$]; [A12, H, H, Cl, CN, CF$_3$CH$_2$];
[A12, H, H, Cl, CN, CF$_3$CF$_2$]; [A12, H, H, Cl, CN, CF$_3$CH$_2$CH$_2$];
[A12, H, H, Cl, CN, CF$_3$CF$_2$CH$_2$]; [A12, H, H, Cl, CN, CF$_3$CF$_2$CF$_2$];
[A12, H, H, H, C(=O)NH$_2$, CF$_3$]; [A12, H, H, H, C(=O)NH$_2$, CF$_3$CH$_2$];
[A12, H, H, H, C(=O)NH$_2$, CF$_3$CF$_2$]; [A12, H, H, H, C(=O)NH$_2$, CF$_3$CH$_2$CH$_2$];
[A12, H, H, H, C(=O)NH$_2$, CF$_3$CF$_2$CH$_2$]; [A12, H, H, H, C(=O)NH$_2$, CF$_3$CF$_2$CF$_2$];
[A12, H, H, F, C(=O)NH$_2$, CF$_3$]; [A12, H, H, F, (=O)NH$_2$, CF$_3$CH$_2$];
[A12, H, H, F, C(=O)NH$_2$, CF$_3$CF$_2$]; [A12, H, H, F, C(=O)NH$_2$, CF$_3$CH$_2$CH$_2$];
[A12, H, H, F, C(=O)NH$_2$, CF$_3$CF$_2$CH$_2$]; [A12, H, H, F, C(=O)NH$_2$, CF$_3$CF$_2$CF$_2$];
[A12, H, H, Cl, C(=O)NH$_2$, CF$_3$]; [A12, H, H, Cl, C(=O)NH$_2$, CF$_3$CH$_2$];
[A12, H, H, Cl, C(=O)NH$_2$, CF$_3$CF$_2$]; [A12, H, H, Cl, C(=O)NH$_2$, CF$_3$CH$_2$CH$_2$];
[A12, H, H, Cl, C(=O)NH$_2$, CF$_3$CF$_2$CH$_2$]; [A12, H, C(=O)NH$_2$, CF$_3$CF$_2$CF$_2$];
[A12, H, H, H, H, CF$_3$]; [A12, H, H, H, H, —CF$_3$CH$_2$];
[A12, H, H, H, H, CF$_3$CF$_2$]; [A12, H, H, H, H, CF$_3$CH$_2$CH$_2$];
[A12, H, H, H, H, CF$_3$, CF$_2$CH$_2$]; [A12, H, H, H, H, CF$_3$CF$_2$CF$_2$];
[A12, H, CN, H, H, CF$_3$]; [A12, H, CN, H, H, CF$_3$CH$_2$];
[A12, H, CN, H, H, CF$_3$CF$_2$]; [A12, H, CN, H, H, CF$_3$CH$_2$CH$_2$];
[A12, H, CN, H, H, CF$_3$CF$_2$CH$_2$]; [A12, H, CN, H, H, CF$_3$CF$_2$CF$_2$];
[A12, F, CN, H, H, CF$_3$]; [A12, F, CN, H, H, CF$_3$CH$_2$];
[A12, F, CN, H, H, CF$_3$CF$_2$]; [A12, F, CN, H, H, CF$_3$CH$_2$CH$_2$];
[A12, F, CN, H, H, CF$_3$CF$_2$CH$_2$]; [A12, F, CN, H, H, CF$_3$CF$_2$CF$_2$];
[A12, Cl, CN, H, H, CF$_3$]; [A12, Cl, CN, H, H, CF$_3$CH$_2$];

[A12, Cl, CN, H, H, CF$_3$CF$_2$]; [A12, Cl, CN, H, H, CF$_3$CH$_2$];
[A12, Cl, CN, H, H, CF$_3$CF$_2$CH$_2$]; [A12, Cl, CN, H, H, CF$_3$CF$_2$CF$_2$];
[A12, H, C(=O)NH$_2$, H, H, CF$_3$]; [A12, H, C(=O)NH$_2$, H, H, CF$_3$CH$_2$];
[A12, H, C(=O)NH$_2$, H, H, CF$_3$CF$_2$]; [A12, H, C(=O)NH$_2$, H, H, CF$_3$CH$_2$CH$_2$];
[A12, H, C(=O)NH$_2$, H, H, CF$_3$CF$_2$CH$_2$]; [A12, H, C(=O)NH$_2$, H, H, CF$_3$CF$_2$CF$_2$];
[A12, F, C(=O)NH$_2$, H, H, CF$_3$]; [A12, F, C(=O)NH$_2$, H, H, CF$_3$CH$_2$];
[A12, F, C(=O)NH$_2$, H, H, CF$_3$CF$_2$]; [A12, F, C(=O)NH$_2$, H, H, CF$_3$CH$_2$CH$_2$];
[A12, F, C(=O)NH$_2$, H, H, CF$_3$CF$_2$CH$_2$]; [A12, F, C(=O)NH$_2$, H, H, CF$_3$CF$_2$CF$_2$];
[A12, Cl, C(=O)NH$_2$, H, H, CF$_3$]; [A12, Cl, C(=O)NH$_2$, H, H, CF$_3$CH$_2$];
[A12, Cl, C(=O)NH$_2$, H, H, CF$_3$CF$_2$]; [A12, Cl, C(=O)NH$_2$, H, H, CF$_3$CH$_2$CH$_2$];
[A12, Cl, C(=O)NH$_2$, H, H, CF$_3$CF$_2$CH$_2$]; [A12, Cl, C(=O)NH$_2$, H, H, CF$_3$CF$_2$CF$_2$];
[A12, H, H, H, CN, CF$_3$]; [A12, H, H, H, CN, CF$_3$CH$_2$];
[A12, H, H, H, CN, CF$_3$CF$_2$]; [A12, H, H, H, CN, CF$_3$CH$_2$CH$_2$];
[A12, H, H, H, CN, CF$_3$CF$_2$CH$_2$]; [A12, H, H, H, CN, CF$_3$CF$_2$CF$_2$];
[A12, H, H, F, CN, CF$_3$]; [A12, H, H, F, CN, CF$_3$CH$_2$];
[A12, H, H, F, CN, CF$_3$CF$_2$]; [A12, H, H, F, CN, CF$_3$CH$_2$CH$_2$];
[A12, H, H, F, CN, CF$_3$CF$_2$CH$_2$]; [A12, H, H, F, CN, CF$_3$CF$_2$CF$_2$];
[A12, H, H, Cl, CN, CF$_3$]; [A12, H, H, Cl, CN, CF$_3$CH$_2$];
[A12, H, H, Cl, CN, CF$_3$CF$_2$]; [A12, H, H, Cl, CN, CF$_3$CH$_2$CH$_2$];
[A12, H, H, Cl, CN, CF$_3$CF$_2$CH$_2$]; [A12, H, H, Cl, CN, CF$_3$CF$_2$CF$_2$];
[A12, H, H, H, C(=O)NH$_2$, CF$_3$]; [A12, H, H, H, C(=O)NH$_2$, CF$_3$CH$_2$];
[A12, H, H, H, C(=O)NH$_2$, CF$_3$CF$_2$]; [A12, H, H, H, C(=O)NH$_2$, CF$_3$CH$_2$CH$_2$];
[A12, H, H, H, C(=O)NH$_2$, CF$_3$CF$_2$CH$_2$]; [A12, H, H, H, C(=O)NH$_2$, CF$_3$CF$_2$CF$_2$];
[A12, H, H, F, C(=O)NH$_2$, CF$_3$]; [A12, H, H, F, C(=O)NH$_2$, CF$_3$CH$_2$];
[A12, H, H, F, C(=O)NH$_2$, CF$_3$CF$_2$]; [A12, H, H, F, C(=O)NH$_2$, CF$_3$CH$_2$CH$_2$];
[A12, H, H, F, C(=O)NH$_2$, CF$_3$CF$_2$CH$_2$]; [A12, H, H, F, C(=O)NH$_2$, CF$_3$CF$_2$CF$_2$];
[A12, H, H, Cl, C(=O)NH$_2$, CF$_3$]; [A12, H, H, Cl, C(=O)NH$_2$ CF$_3$CH$_2$];
[A12, H, H, Cl, C(=O)NH$_2$, CF$_3$CF$_2$]; [A12, H, H, Cl, C(=O)NH$_2$, CF$_3$CH$_2$CH$_2$];
[A12, H, H, Cl, C(=O)NH$_2$, CF$_3$CF$_2$CH$_2$]; [A12, H, H, Cl, C(=O)NH$_2$, CF$_3$CF$_2$CF$_2$];
[A14, H, H, H, H, CF$_3$]; [A14, H, H, H, H, CF$_3$CH$_2$];
[A14, H, H, H, H, CF$_3$CF$_2$]; [A14, H, H, H, H, CF$_3$CH$_2$CH$_2$];
[A14, H, H, H, H, CF$_3$CF$_2$CH$_2$]; [A14, H, H, H, H, CF$_3$CF$_2$CF$_2$];
[A14, H, CN, H, H, CF$_3$]; [A14, H, CN, H, H, CF$_3$CH$_2$];
[A14, H, CN, H, H, CF$_3$CF$_2$]; [A14, H, CN, H, H, CF$_3$CH$_2$CH$_2$];
[A14, H, CN, H, H, CF$_3$CF$_2$CH$_2$]; [A14, H, CN, H, H, CF$_3$CF$_2$CF$_2$];
[A14, F, CN, H, H, CF$_3$]; [A14, F, CN, H, H, CF$_3$CH$_2$];
[A14, F, CN, H, H, CF$_3$CF$_2$]; [A14, F, CN, H, H, CF$_3$CH$_2$CH$_2$];
[A14, F, CN, H, H, CF$_3$CF$_2$CH$_2$]; [A14, F, CN, H, H, CF$_3$CF$_2$CF$_2$];
[A14, Cl, CN, H, H, CF$_3$]; [A14, Cl, CN, H, H, CF$_3$CH$_2$];
[A14, Cl, CN, H, H, CF$_3$CF$_2$]; [A14, Cl, CN, H, H, CF$_3$CH$_2$CH$_2$];
[A14, Cl, CN, H, H, CF$_3$CF$_2$CH$_2$]; [A14, Cl, CN, H, H, CF$_3$CF$_2$CF$_2$];
[A14, H, C(=O)NH$_2$, H, H, CF$_3$]; [A14, H, C(=O)NH$_2$, H, H, CF$_3$CH$_2$];
[A14, H, C(=O)NH$_2$, H, H, CF$_3$CF$_2$]; [A14, H, C(=O)NH$_2$, H, H, CF$_3$CH$_2$CH$_2$];
[A14, H, C(=O)NH$_2$, H, H, CF$_3$CF$_2$CH$_2$]; [A14, H, C(=O)NH$_2$, H, H, CF$_3$CF$_2$CF$_2$];
[A14, F, C(=O)NH$_2$, H, H, CF$_3$]; [A14, F, C(=O)NH$_2$, H, CF$_3$CH$_2$];
[A14, F, C(=O)NH$_2$, H, H, CF$_3$CF$_2$]; [A14, F, C(=O)NH$_2$, H, H, CF$_3$CH$_2$CH$_2$];
[A14, F, C(=O)NH$_2$, H, H, CF$_3$CF$_2$CH$_2$]; [A14, F, C(=O)NH$_2$, H, H, CF$_3$CF$_2$CF$_2$];
[A14, Cl, C(=O)NH$_2$, H, H, CF$_3$]; [A14, Cl, C(=O)NH$_2$, H, H, CF$_3$CH$_2$];
[A14, Cl, C(=O)NH$_2$, H, H, CF$_3$CF$_2$]; [A14, Cl, C(=O)NH$_2$, H, H, CF$_3$CH$_2$CH$_2$];
[A14, Cl, C(=O)NH$_2$, H, H, CF$_3$CF$_2$CH$_2$]; [A14, Cl, C(=O)NH$_2$, H, H, CF$_3$CF$_2$CF$_2$];
[A14, H, H, H, CN, CF$_3$]; [A14, H, H, H, CN, CF$_3$CH$_2$];
[A14, H, H, H, CN, CF$_3$CF$_2$]; [A14, H, H, H, CN, CF$_3$CH$_2$CH$_2$];
[A14, H, H, H, CN, CF$_3$CF$_2$CH$_2$]; [A14, H, H, H, CN, CF$_3$CF$_2$CF$_2$];
[A14, H, H, F, CN, CF$_3$]; [A14, H, H, F, CN, CF$_3$CH$_2$];
[A14, H, H, F, CN, CF$_3$CF$_2$]; [A14, CN, CF$_3$CH$_2$CH$_2$];
[A14, H, H, F, CN, CF$_3$CF$_2$CH$_2$]; [A14, H, H, F, CN, CF$_3$CF$_2$CF$_2$];
[A14, H, H, Cl, CN, CF$_3$]; [A14, H, H, Cl, CN, CF$_3$CH$_2$];
[A14, H, H, Cl, CN, CF$_3$CF$_2$]; [A14, H, H, Cl, CN, CF$_3$CH$_2$CH$_2$];
[A14, H, H, Cl, CN, CF$_3$CF$_2$CH$_2$]; [A14, H, H, Cl, CN, CF$_3$CF$_2$CF$_2$];
[A14, H, H, H, C(=O)NH$_2$, CF$_3$]; [A14, H, H, H, C(=O)NH$_2$, CF$_3$CH$_2$];
[A14, H, H, H, C(=O)NH$_2$, CF$_3$CF$_2$]; [A14, H, H, H, C(=O)NH$_2$, CF$_3$CH$_2$CH$_2$];
[A14, H, H, H, C(=O)NH$_2$, CF$_3$CF$_2$CH$_2$]; [A14, C(=O)NH$_2$, CF$_3$CF$_2$CF$_2$];
[A14, H, H, F, C(=O)NH$_2$, CF$_3$]; [A14, H, H, F, C(=O)NH$_2$, CF$_3$CH$_2$];
[A14, H, H, F, C(=O)NH$_2$, CF$_3$CF$_2$]; [A14, C(=O)NH$_2$ CF$_3$CH$_2$CH$_2$];
[A14, H, H, F, C(=O)NH$_2$, CF$_3$CF$_2$CH$_2$]; [A14, H, C(=O)NH$_2$, H, H, CF$_3$CF$_2$CF$_2$];
[A14, H, H, Cl, C(=O) NH$_2$, CF$_3$]; [A14, H, H, Cl, C(=O)NH$_2$, CF$_3$CH$_2$];
[A14, H, H, Cl, C(=O)NH$_2$, CF$_3$CF$_2$]; [A14, H, H, Cl, C(=O)NH$_2$, CF$_3$CH$_2$CH$_2$];
[A14, H, H, Cl, C(=O)NH$_2$, CF$_3$CF$_2$CH$_2$]; [A14, H, H, Cl, C(=O)NH$_2$, CF$_3$CF$_2$CF$_2$];
[A15, H, H, H, H, CF$_3$]; [A15, H, H, H, H, CF$_3$CH$_2$];
[A15, H, H, H, H, CF$_3$CF$_2$]; [A15, H, H, H, H, CF$_3$CH$_2$CH$_2$];
[A15, H, H, H, H, CF$_3$CF$_2$CH$_2$]; [A15, H, H, H, H, CF$_3$CF$_2$CF$_2$];
[A15, H, CN, H, H, CF$_3$]; [A15, H, CN, H, H, CF$_3$CH$_2$];
[A15, H, CN, H, H, CF$_3$CF$_2$]; [A15, H, CN, H, H, CF$_3$CH$_2$CH$_2$];
[A15, H, CN, H, H, CF$_3$CF$_2$CH$_2$]; [A15, H, CN, H, H, CF$_3$CF$_2$CF$_2$];
[A15, F, CN, H, H, CF$_3$]; [A15, F, CN, H, H, CF$_3$CH$_2$];

[A15, F, CN, H, H, CF₃CF₂]; [A15, F, CN, H, H, CF₃CH₂CH₂];
[A15, F, CN, H, H, CF₃CF₂CH₂]; [A15, F, CN, H, H, CF₃CF₂CF₂];
[A15, Cl, CN, H, H, CF₃]; [A15, Cl, CN, H, H, CF₃CH₂];
[A15, Cl, CN, H, H, CF₃CF₂]; [A15, Cl, CN, H, H, CF₃CH₂CH₂];
[A15, Cl, CN, H, H, CF₃CF₂CH₂]; [A15, Cl, CN, H, H, CF₃CF₂CF₂];
[A15, H, C(=O)NH₂, H, H, CF₃]; [A15, H, C(=O)NH₂, H, H, CF₃CH₂];
[A15, H, C(=O)NH₂, H, H, CF₃CF₂]; [A15, H, C(=O)NH₂, H, H, CF₃CH₂CH₂];
[A15, H, C(=O)NH₂, H, H, CF₃CF₂CH₂]; [A15, H, C(=O)NH₂, H, H, CF₃CF₂CF₂];
[A15, F, C(=O)NH₂, H, H, CF₃]; [A15, F, C(=O)NH₂, H, H, CF₃CH₂];
[A15, F, C(=O)NH₂, H, H, CF₃CF₂]; [A15, F, C(=O)NH₂, H, H, CF₃CH₂CH₂];
[A15, F, C(=O)NH₂, H, H, CF₃CF₂CH₂]; [A15, F, C(=O)NH₂, H, H, CF₃CF₂CF₂];
[A15, Cl, C(=O)NH₂, H, H, CF₃]; [A15, Cl, C(=O)NH₂, H, H, CF₃CH₂];
[A15, Cl, C(=O)NH₂, H, H, CF₃CF₂]; [A15, Cl, C(=O)NH₂, H, H, CF₃CH₂CH₂];
[A15, Cl, C(=O)NH₂, H, H, CF₃CF₂CH₂]; [A15, Cl, C(=O)NH₂, H, H, CF₃CF₂CF₂];
[A15, H, H, H, CN, CF₃]; [A15, H, H, H, CN, CF₃CH₂];
[A15, H, H, H, CN, CF₃CF₂]; [A15, H, H, H, CN, CF₃CH₂CH₂];
[A15, H, H, H, CN, CF₃CF₂CH₂]; [A15, H, H, H, CN, CF₃CF₂CF₂];
[A15, H, H, F, CN, CF₃]; [A15, H, H, F, CN, CF₃CH₂];
[A15, H, H, F, CN, CF₃CF₂]; [A15, H, H, F, CN, CF₃CH₂CH₂];
[A15, H, H, F, CN, CF₃CF₂CH₂]; [A15, H, H, F, CN, CF₃CF₂CF₂];
[A15, H, H, Cl, CN, CF₃]; [A15, H, H, Cl, CN, CF₃CH₂];
[A15, H, H, Cl, CN, CF₃CF₂]; [A15, H, H, Cl, CN, CF₃CH₂CH₂];
[A15, H, H, Cl, CN, CF₃CF₂CH₂]; [A15, H, H, Cl, CN, CF₃CF₂CF₂];
[A15, H, H, H, C(=O)NH₂, CF₃]; [A15, H, H, H, C(=O)NH₂, CF₃CH₂];
[A15, H, H, H, C(=O)NH₂, CF₃CF₂]; [A15, H, H, H, C(=O)NH₂, CF₃CH₂CH₂];
[A15, H, H, H, C(=O)NH₂, CF₃CF₂CH₂]; [A15, H, H, H, C(=O)NH₂, CF₃CF₂CF₂];
[A15, H, H, F, C(=O)NH₂, CF₃]; [A15, H, H, F, C(=O)NH₂, CF₃CH₂];
[A15, H, H, F, C(=O)NH₂, CF₃CF₂]; [A15, H, H, F, C(=O)NH₂, CF₃CH₂CH₂];
[A15, H, H, F, C(=O)NH₂, CF₃CF₂CH₂]; [A15, H, H, F, C(=O)NH₂, CF₃CF₂CF₂];
[A15, H, H, Cl, C(=O)NH₂, CF₃]; [A15, H, H, Cl, C(=O)NH₂, CF₃CH₂];
[A15, H, H, Cl, C(=O)NH₂, CF₃CF₂]; [A15, H, H, Cl, C(=O)NH₂, CF₃CH₂CH₂];
[A15, H, H, Cl, C(=O)NH₂, CF₃CF₂CH₂]; [A15, H, H, Cl, C(=O)NH₂, CF₃CF₂CF₂].

Wherein, A1 to A15 are saturated heterocyclic groups represented by the following formulae.

(A1)

(A2)

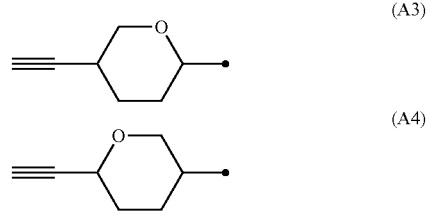
(A3)

(A4)

(A5)

(A5)

(A6)

(A7)

(A8)

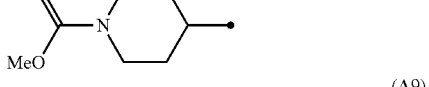
(A9)

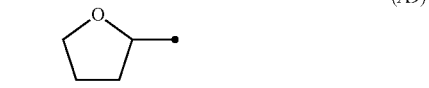
(A10)

(A11)

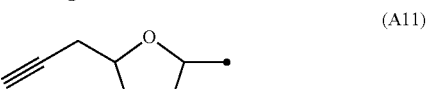
(A12)

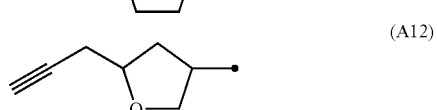
(A13)

(A14)

(A15)

A compound represented by the formula (Iβ):

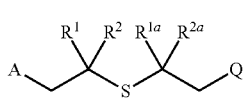

wherein A, $R^1$, $R^2$, $R^{1a}$, $R^{2a}$, Q, and n represent any one of combinations shown above.

A compound represented by the formula (Iγ):

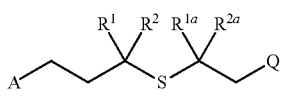

wherein A, $R^1$, $R^2$, $R^{1a}$, $R^{2a}$, Q, and n represent any one of combinations shown above.

A compound represented by the formula (Iδ):

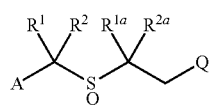

wherein A, $R^1$, $R^2$, $R^{1a}$, $R^{2a}$, Q and n represent any one of combinations shown above.

A compound represented by the formula (Iε):

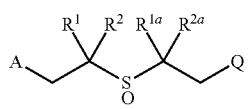

wherein A, $R^1$, $R^2$, $R^{1a}$, $R^{2a}$, Q, and n represent any one of combinations shown above.

A compound represented by the formula (Iζ):

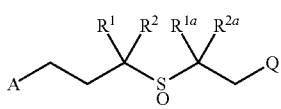

wherein A, $R^1$, $R^2$, $R^{1a}$, $R^{2a}$, Q, and n represent any one of combinations shown above.

A compound represented by the formula (Iη):

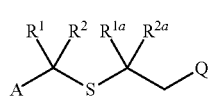

wherein A, $R^1$, $R^2$, $R^{1a}$, $R^{2a}$, Q and n represent any one of combinations shown above.

A compound represented by the formula (Iθ):

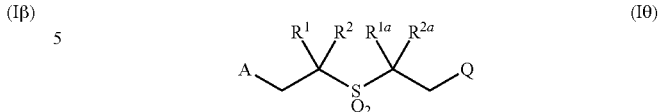

wherein A, $R^1$, $R^2$, $R^{1a}$, $R^{2a}$, Q and n represent any one of combinations shown above.

A compound represented by the formula (Iκ):

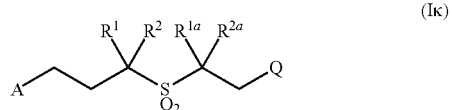

wherein A, $R^1$, $R^2$, $R^{1a}$, $R^{2a}$, Q, and n represent any one of combinations shown above.

Formulation Examples will be shown below. The term "part(s)" means part(s) by weight.

Formulation Example 1

Nine parts of any one of the present compounds (1) to (26) is dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 2

To 40 parts of any one of the present compounds (1) to (26) is added 5 parts of SORPOL 5060 (registered trade name for TOHO Chemical Industry Co., LTD.) and mixed thoroughly. The mixture is mixed with 32 parts of CARPLEX #80 (registered trade name for Shionogi & Co., Ltd., synthetic hydrous silicon oxide fine powder) and 23 parts of 300 mesh diatomaceous earth by using a juice mixer to obtain a wettable powder.

Formulation Example 3

Three parts of any one of the present compounds (1) to (26), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 4

Four point five parts of any one of the present compounds (1) to (24), 1 part of synthetic hydrous silicon oxide fine powder, 1 part of Dorires B (manufactured by Sankyo) as a flocculant, and 7 parts of clay are mixed thoroughly in a mortar, and then mixed by stirring by using a juice mixer. To the resultant mixture 86.5 parts of cut clay is added and mixed by stirring thoroughly to obtain a dust.

Formulation Example 5

Ten parts of any one of the present compounds (1) to (26), 35 parts of a mixture (weight ratio of 1:1) of a polyoxyethylene alkylether sulfate ammonium salt and white carbon, and 55 parts of water are mixed and then finely-divided by a wet grinding method to obtain a formulation.

Formulation Example 6

Zero point five part of any one of the present compounds (1) to (26) is dissolved in 10 parts of dichloromethane. This solution is mixed with 89.5 parts of Isopar M (isoparaffin: registered trade name for Exxon Chemical) to obtain an oil solution.

Formulation Example 7

Zero point one part of any one of the present compounds (1) to (26) and 49.9 parts of NEO-THIOZOL (Chuo Kasei Co., Ltd.) are placed in an aerosol can. An aerosol valve is fitted to the can. The can is charged with 25 parts of dimethyl ether and 25 parts of LPG. An actuator is fitted to the can to obtain an oily aerosol.

Formulation Example 8

Zero point six parts of any one of the present compounds (1) to (26), 0.01 part of BHT, 5 parts of xylene, 3.39 parts of a deodorized kerosine and 1 part of an emulsifying agent [Atmos 300 (registered trade name for Atmos Chemical Ltd.)] are mixed to obtain a solution. An aerosol container is charged with the obtained solution and 50 parts of distilled water. A valve part is attached to the container and the container is then charged with 40 parts of a propellant (LPG) through the valve under increased pressure to obtain an aqueous aerosol.

The following Test Examples demonstrate that the compound of the present invention is effective as an active ingredient of an arthropod pest-controlling composition.

Test Example 1

A formulation of any one of the present compounds (4), (5), (6), (7), (8), (9), (10), (11), (12), (15), (16), (17), (18), (19), (20), (21), (22), (23), (24) and (26) obtained in Formulation Example 5 was diluted with water to prepare a test solution having 500 ppm of the active ingredient.

Separately, 50 g of culture soil, Bonsol No. 2 (manufactured by Sumitomo Chemical Co., Ltd.) was put into a polyethylene cup, and 10 to 15 seeds of rice were planted therein. The rice plants were grown until the second foliage leaf was developed, and then cut into the same height of 5 cm. Then, 20 ml/cup of the test solution was sprayed on the rice plants. After the test solution sprayed over the rice plant was dried, the rice plant was placed in plastic cup so as to prevent escape of a test insect. Thirty (30) first-instar larvae of *Nilaparvata lugens* were released into the cup, and the cup was sealed with a lid. Then, the cup was left in a greenhouse at 25° C. for 6 days. Then, the number of *Nilaparvata lugens* parasitic on the rice plants was counted.

As a result, on the plants treated with any one of the present compounds (4), (5), (6), (7), (8), (9), (10), (11), (12), (15), (16), (17), (18), (19), (20), (21), (22), (23) (24) and (26), the number of the parasitic pests was 3 or smaller.

Test Example 2

A formulation of any one of the present compounds (1), (4), (5), (6), (7), (8), (9), (10), (11), (12), (15), (16), (17), (18), (19), (20), (21), (22), (23), (24) and (26) obtained in Formulation Example 5 was diluted with water to prepare a test solution having 55.6 ppm of the active ingredient.

Separately, 50 g of culture soil, Bonsol No. 2 (manufactured by Sumitomo Chemical Co., Ltd.) was put into a polyethylene cup with five holes 5 mm in diameter at the bottom, and 10 to 15 seeds of rice were planted therein. The rice plants were grown until the second foliage leaf was developed, and then treated with 45 ml of the test solution by allowing the plants to absorb the test solution from the bottom of the cup. The rice plants were placed in a greenhouse at 25° C. for 6 days and then cut into the same height of 5 cm. Thirty (30) first-instar larvae of *Nilaparvata lugens* were released into the cup, and then the cup was left in a greenhouse at 25° C. for 6 days. Then, the number of *Nilaparvata lugens* parasitic on the rice plants was counted.

As a result, on the plants treated with any one of the present compounds (1), (4), (5), (6), (7), (8), (9), (10), (11), (12), (15), (16), (17), (18), (19), (20), (21), (22), (23), (24) and (26), the number of the parasitic pests was 3 or smaller.

Test Example 3

A formulation of any one of the present compounds (4), (5), (6), (7), (8), (9), (11), (15), (16), (18) and (23) obtained in Formulation Example 5 was diluted with water to prepare a test solution having 500 ppm of the active ingredient.

Separately, cucumber was planted in a polyethylene cup and was grown until the first foliage leaf was developed, on which about 20 individuals of *Aphis gossypii* were placed. After 1 day, the test solution was sprayed on the cucumber in the amount of 20 ml/cup. After 6 days, the number of *Aphis gossypii* was counted.

As a result, on the cucumber treated with any one of the present compounds (4), (5), (6), (7), (8), (9), (11), (15), (16), (18) and (23), the number of the parasitic pests was 3 or smaller.

Test Example 4

A formulation of any one of the present compounds (1), (4), (6), (7), (9), (10), (11), (12), (13), (15), (16), (17), (18), (19), (20), (21), (22), (24), (25) and (26) obtained in Formulation Example 5 was diluted with water to prepare a test solution having 500 ppm of the active ingredient.

A filter paper having a diameter of 5.5 cm was spread on the bottom of a polyethylene cup having a diameter of 5.5 cm and 0.7 ml of the test solution was added dropwise onto the filter paper. As a bait, 30 mg of sucrose was uniformly placed on the filter paper. Into the polyethylene cup, 10 female imagoes of *Musca domestica* were released and the cup was sealed with a lid. After 24 hours, the number of surviving or dead *Musca domestica* was counted and the death rate of the pest was calculated.

As a result, the treatment with any one of the present compounds (1), (4), (6), (7), (9), (10), (11), (12), (13), (15), (16), (17), (18), (19), (20), (21), (22), (24), (25) and (26) showed a pest death rate of 90% or more.

Test Example 5

A formulation of any one of the present compounds (4), (5), (6), (8), (12), (15), (16), (18), (22), (23) and (24) obtained in Formulation Example 5 was diluted with water to prepare a test solution having 500 ppm of the active ingredient.

A filter paper having a diameter of 5.5 cm was spread on the bottom of a polyethylene cup having a diameter of 5.5 cm and 0.7 ml of the test solution was added dropwise onto the filter paper. As a bait, 30 mg of sucrose was uniformly placed on the filter paper. Into the polyethylene cup, 2 male imagoes of *Blattalla germanica* were released and the cup was sealed with a lid. After 6 days, the number of surviving or dead *Blattalla germanica* was counted and the death rate of the pest was calculated.

As a result, the treatment with any one of the present compounds (4), (5), (6), (8), (12), (15), (16), (18), (22), (23) and (24) showed a pest death rate of 100%.

Test Example 6

A formulation of any one of the present compounds (4), (5), (6), (7), (8), (9), (11), (12), (15), (16), (18), (19), (20), (21), (22), and (26) obtained in Formulation Example 5 was diluted with water to prepare a test solution having 500 ppm of the active ingredient.

To 100 mL of ion-exchanged water, 0.7 ml of the test solution was added (active ingredient concentration: 3.5 ppm). Into the solution, 20 last-instar larvae of *Culex pipiens pallens* were released. After 1 day, the number of surviving or dead *Culex pipiens pallens* was counted and the death rate of the pest was calculated.

As a result, the treatment with any one of the present compounds (4), (5), (6), (7), (8), (9), (11), (12), (15), (16), (18), (19), (20), (21), (22), and (26) showed a pest death rate of 95% or more.

INDUSTRIAL APPLICABILITY

The compound of the present invention has a controlling effect on arthropod pests, and is therefore useful as an active ingredient of an arthropod pest-controlling composition.

The invention claimed is:

1. A halogen-containing organosulfur compound represented by the following formula (I):

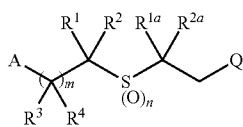

wherein
m represents 0, 1 or 2,
n represents 1 or 2,
A represents a 3- to 8-membered saturated heterocyclic group optionally substituted with a group selected from the group E1,
Q represents a fluorine atom, or a C1-C5 haloalkyl group containing at least one fluorine atom,
$R^1$, $R^{1a}$ and $R^3$ independently represent an optionally halogenated C1-C4 chain hydrocarbon group, a halogen atom, or a hydrogen atom,
$R^2$, $R^{2a}$ and $R^4$ independently represent an optionally halogenated C1-C4 chain hydrocarbon group, C(=G)$R^5$, a cyano group, a halogen atom, or a hydrogen atom,
G represents an oxygen atom or a sulfur atom,
$R^5$ represents an optionally halogenated C1-C4 alkyl group, a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally haloge- nated di(C1-C4 alkyl)amino group, a C2-C5 cyclic amino group, or a hydrogen atom,
the group E1 consists of —$OR^6$, —$SR^6$, —S(=O)$R^6$, —S(O)$_2R^6$, —C(=O)$R^7$, —OC(=O)$R^8$, a C1-C6 chain hydrocarbon group optionally substituted with a group selected from the group L, an optionally halogenated C3-C6 cycloalkyl group, a cyano group, a hydroxyl group, and a halogen atom,
$R^6$ represents a C1-C6 chain hydrocarbon group optionally substituted with a group selected from the group L, or an optionally halogenated C3-C6 cycloalkyl group,
$R^7$ represents a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl group, or a hydrogen atom,
$R^8$ represents an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, C2-C5 cyclic amino group, an optionally halogenated C1-C4 alkyl group, or a hydrogen atom,
the group L consists of a hydroxyl group, an optionally halogenated C1-C4 alkoxy group, an optionally halogenated C3-C6 alkenyloxy group, an optionally halogenated C3-C6 alkynyloxy group, —C(=O)$R^7$, —OC(=O)$R^8$, —N($R^9$)$R^{10}$, a C2-C5 cyclic amino group, and a halogen atom, and
$R^9$ and $R^{10}$ represent an optionally halogenated C1-C4 alkyl group, an optionally halogenated C3-C6 alkenyl group, an optionally halogenated C3-C6 alkynyl group, an optionally halogenated C3-C6 cycloalkyl group, an optionally halogenated phenyl group, or a hydrogen atom.

2. The halogen-containing organosulfur compound according to claim 1, wherein $R^3$ and $R^4$ are hydrogen atoms.

3. The halogen-containing organosulfur compound according to claim 1, wherein m is 0.

4. An arthropod pest-controlling composition comprising the halogen-containing organosulfur compound according to any one of claims 1 to 3 as an active ingredient.

5. A method for controlling an arthropod pest, which comprises applying an effective amount of the halogen-containing organosulfur compound according to any one of claims 1 to 3 to the arthropod pest or a habitat of the arthropod pest.

6. A halogen-containing organosulfur compound represented, the following formula (I):

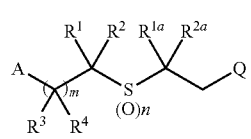

wherein
m represents 0, 1 or 2,
a represents 0, 1 or 2,
A represents a 3- to 8-membered saturated heterocyclic group optionally substituted with a group selected from the group E1, Q represents a fluorine atom, or a C1-C5 haloalkyl group containing at least one fluorine atom, $R^1$ represents a halogen atom or a hydrogen atom, $R^{1a}$ and $R^3$ independently represent an optionally halogenated C1-C4 chain hydrocarbon group, a halogen atom, or a hydrogen atom, $R^2$ represents —C(=G)$R^5$ or a cyano group, $R^{2a}$ and $R^4$ independently represent an optionally halogenated C1-C4 chain hydrocarbon group, —C(=G)$R^5$, a cyano group, a halogen atom, or a hydrogen atom, G represents an oxygen atom or a sulfur atom, $R^5$ represents an optionally halogenated C1-C4 alkyl group, a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, or a hydrogen atom, the group E1 consists of —O$R^6$, —S$R^6$, —S(=O)$R^6$, —S(=O)$_2R^6$, —C(=O)$R^7$, —OC(=O)$R^8$, a C1-C6 chain hydrocarbon group optionally substituted with a group selected from the group L, an optionally halogenated C3-C6 cycloalkyl group, a cyano group, a hydroxyl group, and a halogen atom, $R^6$ represents a C1-C6 chain hydrocarbon group Optionally substituted with a group selected from the group L, or an optionally halogenated C3-C6 cycloalkyl group, $R^7$ represents a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl group, or a hydrogen atom, $R^8$ represents an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl) group, or a hydrogen atom, the group L consists of a hydroxyl group, an optionally halogenated C1-C4 alkoxy group, an optionally halogenated C3-C6 alkenyloxy group, an optionally halogenated C3-C6 alkynyloxy group, —C(=O)$R^7$, —OC(=O)$R^8$, —N($R^9$)$R^{10}$, a C2-C5 cyclic amino group, and a halogen atom, and $R^9$ and $R^{10}$ independently represent an optionally halogenated C1-C4 alkyl group, an optionally halogenated C3-C6 alkenyl group, an optionally halogenated C3-C6 alkynyl group, an optionally halogenated C3-C6 cycloalkyl group, an optionally halogenated phenyl group, or a hydrogen atom.

7. A halogen-containing organosulfur compound represented by the following formula (I):

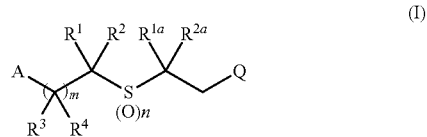

wherein m represents 0, 1 or 2, n represents 0, 1 or 2,

A represents a 3- to 8-membered saturated heterocyclic group optionally substituted with a group selected from the group E1, Q represents a fluorine atom, or a C1-C5 haloalkyl group containing at least one fluorine atom, $R^1$ and $R^3$ independently represent an optionally halogenated C1-C4 chain hydrocarbon group, a halogen atom, or a hydrogen atom, $R^{1a}$ independently represents a halogen atom or a hydrogen atom, $R^{2a}$ represents —C(=G)$R^5$ or a cyano group, $R^2$ and $R^4$ independently represent an optionally halogenated C1-C4 chain hydrocarbon group, —C(=G)$R^5$, a cyano group, a halogen atom, or a hydrogen atom, G represents an oxygen atom or a sulfur atom, $R^5$ represents an optionally halogenated C1-C4 alkyl group, a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, or a hydrogen atom, the group E1 consists of —O$R^6$, —S$R^6$, —S(=O)$R^6$, —S(=O)$_2R^6$, —C(=O)$R^7$, —OC(=O)$R^8$, a C1-C6 chain hydrocarbon group optionally substituted with a group selected from the group L, an optionally halogenated C3-C6 cycloalkyl group, a cyano group, a hydroxyl group, and a halogen atom, $R^6$ represents a C1-C6 chain hydrocarbon group optionally substituted with a group selected from the group or an optionally halogenated C3-C6 cycloalkyl group, $R^7$ represents a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl group, or a hydrogen atom, $R^8$ represents an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl group, or a hydrogen atom, the group L consists of a hydroxyl group, an optionally halogenated C1-C4 alkoxy group, an optionally halogenated C3-C6 alkenyloxy group, an optionally halogenated C3-C6 alkynyloxy group, —C(=O)R$^7$, —OC(=O)R$^8$, —N(R$^9$)R$^{10}$, a C2-C5 cyclic amino group, and a halogen atom, and R$^9$ and R$^{10}$ independently represent an optionally halogenated C1-C4/alkyl group, an optionally halogenated C3-C6 alkenyl group, an optionally halogenated C3-C6 alkynyl group, an optionally halogenated C3-C6 cycloalkyl group, an optionally halogenated phenyl group, or a hydrogen atom.

8. A method for controlling an arthropod pest, which comprises applying an effective amount of a halogen-containing organosulfur compound to the arthropod pest or a habitat of the arthropod pest, and the halogen-containing organosulfur compound is represented by the following formula (I):

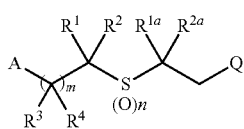

(I)

wherein m represents 0, 1 or 2, n represents 0, 1 or 2,

A represents a 3- to 8-membered saturated heterocyclic group optionally substituted with a group selected from the group E1, Q represents a fluorine atom, or a C1-C5 haloalkyl group containing at least one fluorine atom, R$^1$, R$^{1a}$ and R$^3$ independently represent an optionally halogenated C1-C4 chain hydrocarbon group, a halogen atom, or a hydrogen atom, R$^2$, R$^{2a}$ and R$^4$ independently represent an optionally halogenated C1-C4 chain hydrocarbon group, —C(=G)R$^5$, a cyano group, a halogen atom, or a hydrogen atom, G represents an oxygen atom or a sulfur atom, R$^5$ represents an optionally halogenated C1-C4 alkyl group, a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl) group, a C2-C5 cyclic amino group, or a hydrogen atom, the group E1 consists of –OR$^6$, —SR$^6$, —S(=O)R$^6$, —S(=O)$_2$R$^6$, —C(O)R$^7$, —OC(=O)R$^8$, a C1-C6 chain hydrocarbon group optionally substituted with a group selected from the group L, an optionally halogenated C3-C6 cycloalkyl group, a cyano group, a hydroxyl group, and a halogen atom, R$^6$ represents a C1-C6 chain hydrocarbon group optionally substituted with a group selected from the group L, or an optionally halogenated C3-C6 cycloalkyl group, R$^7$ represents a hydroxyl group, an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl group, or a hydrogen atom, R$^8$ represents an optionally halogenated C1-C4 alkoxy group, an optionally halogenated C3-C6 alkenyloxy group, an optionally halogenated C3-C6 alkynyloxy group, an amino group, an optionally halogenated C1-C4 alkylamino group, an optionally halogenated di(C1-C4 alkyl)amino group, a C2-C5 cyclic amino group, an optionally halogenated C1-C4 alkyl group, or a hydrogen atom, the group L consists of a hydroxyl group, an optionally halogenated C1-C4 alkoxy group, an optionally halogenated C3-C6 alkenyloxy group, an optionally halogenated C3-C6 alkynyloxy group, —C(=O)R$^7$, —OC(=O)R$^8$, —N(R$^9$)R$^{10}$, a C2-C5 cyclic amino group, and a halogen atom, and R$^9$ and R$^{10}$ independently represent an optionally halogenated C1-C4 alkyl group, an optionally halogenated C3-C6 alkenyl group, an optionally halogenated C3-C6 alkyl group, an optionally halogenated C3-C6 cycloalkyl group, an optionally halogenated phenyl group, or a hydrogen atom.

* * * * *